Figure 1:
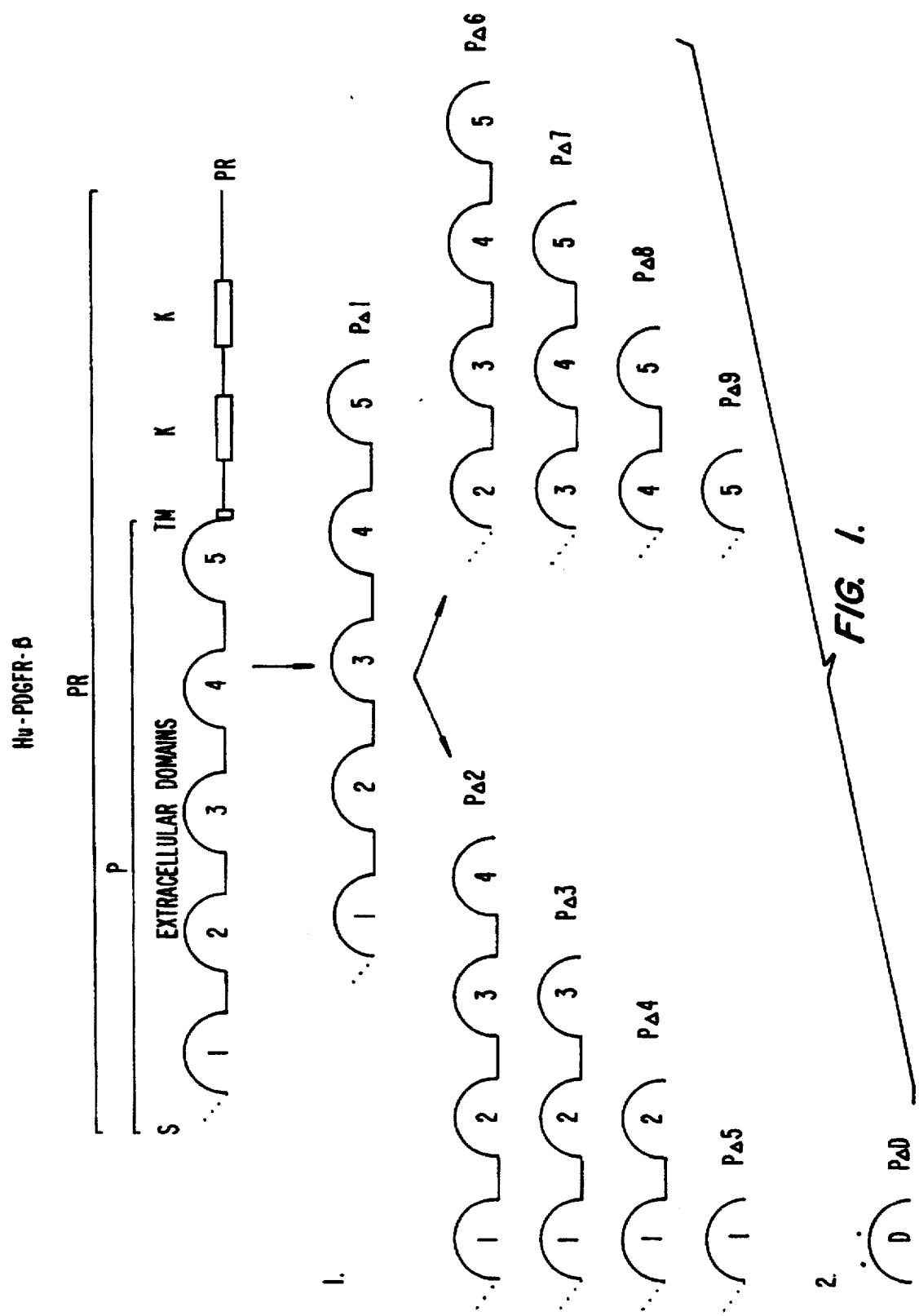
Figure 2:
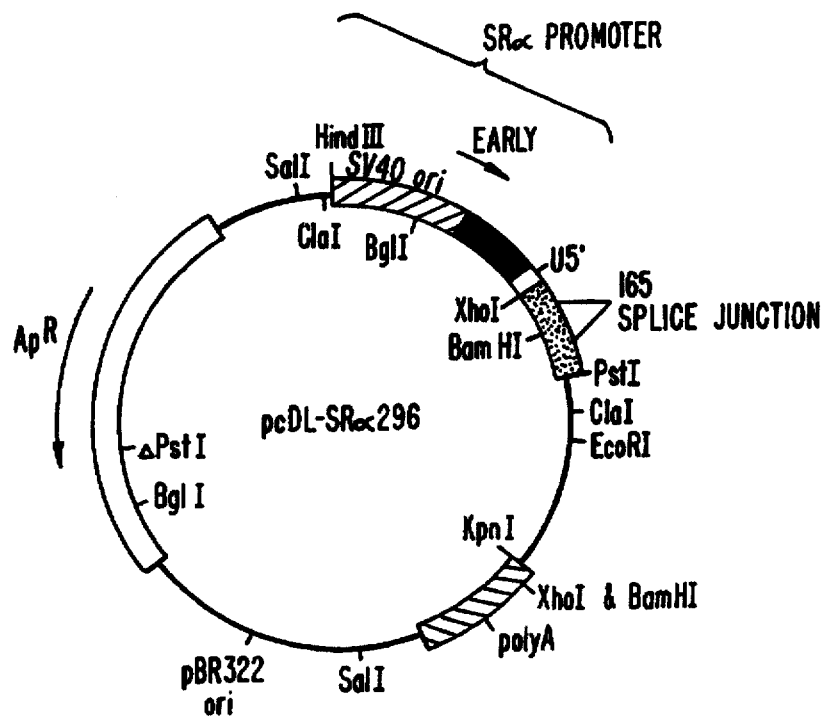
Figure 3:
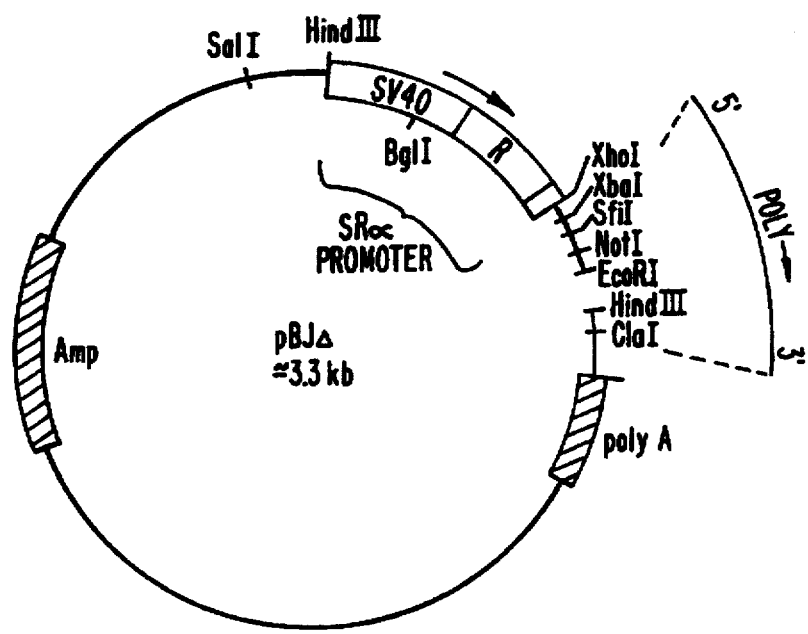

US005686572A

United States Patent [19]
Wolf et al.

[11] Patent Number: 5,686,572
[45] Date of Patent: Nov. 11, 1997

[54] DOMAINS OF EXTRACELLULAR REGION OF HUMAN PLATELET DERIVED GROWTH FACTOR RECEPTOR POLYPEPTIDES

[75] Inventors: David Wolf, Palo Alto; James E. Tomlinson, San Francisco; Larry J. Fretto, Belmont; Neill A. Giese; Jaime A. Escobedo, both of San Francisco; Lewis Thomas Williams, Tiburon, all of Calif.

[73] Assignees: Cor Therapeutics, Inc., South San Francisco; The Regents of the University of California, Oakland, both of Calif.

[21] Appl. No.: 168,917

[22] Filed: Dec. 15, 1993

Related U.S. Application Data

[63] Continuation of Ser. No. 650,793, Jan. 31, 1991, abandoned.
[51] Int. Cl.$^6$ .................. C07K 14/71; C07K 19/00
[52] U.S. Cl. ............. 530/350; 530/402; 435/69.1
[58] Field of Search ............... 435/240.2, 320.1, 435/7.21, 4, 6, 172.1, 172.3, 69.1, 240.27; 530/350, 398, 399, 387.1; 536/23.1, 23.4, 23.5, 23.53; 424/85.8

[56] References Cited

U.S. PATENT DOCUMENTS 5,155,027  10/1992  Sledziewski et al. ............... 435/69.7

FOREIGN PATENT DOCUMENTS

| 0 327 369 | 2/1989 | European Pat. Off. . |
| 0 325 224 | 7/1989 | European Pat. Off. . |
| 90/10013 | 9/1990 | WIPO . |
| WO 91/17252 | 11/1991 | WIPO . |
| WO 92/13870 | 8/1992 | WIPO . |
| WO 93/10805 | 6/1993 | WIPO . |
| WO 93/11223 | 6/1993 | WIPO . |

OTHER PUBLICATIONS

Russell Ross et al, "The Biology of Platelet–Derived Growth Factor," *Cell*, 46:155–169, Jul. 18, 1986.

Orchansky et al. (1988), "Expression and Characterization of the Extracytoplasmic Portion of the Mouse Platelet Derived Growth Factor Receptor," *Journal of Cellular Biochemistry*, 12:110.

Bazan et al. (1988), "Structural and Functional Model of the Platelet Derived Growth Factor Receptor Extracellular Domain," *Journal of Cellular Biochemistry*, 12:98.

Escobedo et al. (1988), "A Common PDGF Receptor is Activated by Homodimeric A and B Forms of PDGF" *Science* 240:1532–1534.

Kazlauskas et al. (1988) "Different effects of homo–and heterodimers of platelet–derived growth factor A and B chains on human and mouse fibroblasts" *EMBO J.* 7:3727–3735.

Hart et al. (1988) "Two Classes of PDGF Receptor Recognize Different Isoforms of PDGF" *Science* 240:1529–1531.

Escobedo et al. (1988) "Platelet–Derived Growth Factor Receptors Expressed by cDNA Transfection Couple to a Diverse Group of Cellular Responses Associated with Cell Proliferation" *J. Biol. Chem.* 263:1482–1487.

Yarden et al. (1986) "Structure of the receptor for platelet–derived growth factor helps define a family of closely related growth factor receptors" *Nature* 323:226–232.

Gronwald et al. (1988) "Cloning and expression of a cDNA coding for the human platelet–derived growth factor receptor: Evidence for more than one receptor class" *Proc. Nat'l Acad. Sci. USA* 85:3435–3439.

Glenn et al. (1982) "Platelet–Derived Growth Factor" *J. Biol. Chem.* 257:5172–5176.

Haynes et al. (1983) "Constitutive, long–term production of human interferons by hamster cells containing multiple copies of a cloned interferon gene" *Nucl. Acids Res.* 11:687–706.

Peralta et al. (1987) "Primary Structure and Biochemical Properties of an $M_2$ Muscarinic Receptor" *Science* 257:600–605.

Heldin et al. (1982) "Interaction of Platelet–Derived Growth Factor with Its Fibroblast Receptor" *J. Biol. Chem.* 257:4216–4221.

Daniel et al. (1985) "Purification of the platelet–derived growth factor receptor by using an anti–phosphotyrosine antibody" *Proc. Nat'l Acad. Sci. USA* 82:2684–2687.

Claesson–Welsh et al., (1988) "cDNA Cloning and Expression of a Human Platelet–Derived Growth Factor (PDGF) Receptor Specific for B–Chain–Containing PDGF Molecules" *Mol. Cell. Biol.* 8:3476–3486.

Williams (1989) "Signal Transduction by the Platelet–Derived Growth Factor Receptor" *Science* 243:1564–1570.

Williams et al. (1986) "PDGF receptors: Structural and Functional Studies" *Miami Winter Symposium* 1986.

Williams et al. (1988) "The Immunoglobulin Superfamily–Domains for Cell Surface Recognition" *Ann. Rev. Immunology* 6:381–405.

Williams (1988) "Stimulation of Paracrine and Autocrine Pathways of Cell Proliferation by Platelet–Derived Growth Factor" *Clinical Research* 36:5–10.

Williams et al. (1987) "The Stimulation of Paracrine and Autocrine Mitogenic Pathways by the Platelet–Derived Growth Factor Receptor" *J. Cell. Physiol. Supp.* 5:27–30.

(List continued on next page.)

*Primary Examiner*—Stephen G. Walsh
*Assistant Examiner*—Stephen Gucker
*Attorney, Agent, or Firm*—Townsend & Townsend & Crew LLP

[57] ABSTRACT

Defined constructs of modified human platelet-derived growth factor receptor polypeptides are provided. Extracellular region domain structures are identified and modifications and combinatorial rearrangements of the receptor segments are provided. Both cell bound and soluble forms of modified segments are made available, as are methods for assays using them, allowing for screening of ligand analogues.

8 Claims, 3 Drawing Sheets

OTHER PUBLICATIONS

Fantl et al. (1989) "Mutations of the Platelet–Derived Growth Factor Receptor That Cause a Loss of Ligand–Induced Conformational Change, Subtle Changes in Kinase Activity, and Impaired Ability To Stimulate DNA Synthesis" *Mol. Cell. Biol.* 9:4473–4478.

Yarden et al. (1988) "Growth Factor Receptor Tyrosine Kinases" *Ann. Rev. Biochem.* 57:443–78.

Ullrich et al. (1990) "Signal Transduction by Receptors with Tyrosine Kinase Activity" *Cell* 61:203–212.

Claesson–Welsh et al. (1989) "cDNA cloning and expression of human A–type platelet–derived growth factor (PDGF) receptor establishes structural similarity to the B–type PDGF receptor" *Proc. Nat'l Acad. Sci. USA* 86:4917–4921.

Matsui et al. (1989) "Isolation of a Novel Receptor cDNA Establishes the Existence of Two PDGF Receptor Genes" *Science* 243:800–803.

Ruta et al. (1988) "A novel protein tyrosine kinase gene whose expression is modulated during endothelial cell differentiation" *Oncogene* 3:9–15.

Reid et al. (1990) "Two forms of the basic fibroblast growth factor receptor–like mRNA are expressed in the developing mouse brain" *Proc. Nat'l Acad. Sci. USA* 87:1596–1600.

Kornbluth et al. (1988) "Novel Tyrosine Kinase Identified by Phosphotyrosine Antibody Screening of cDNA Libraries" *Mol. Cell. Biol.* 8:5541–5544.

Escobedo et al. (1988) "Role of Tyrosine Kinase and Membrane–Spanning Domains in Signal Transduction by the Platelet–Derived Growth Factor Receptor" *Mol. Cell. Biol.* 8:5126–5131.

Qiu et al. (1988) "Primary structure of c–kit: relationship with the CSF–1/PDGF receptor kinase family–oncogenic activation of v–kit involves deletion of extracellular domain and C terminus" *EMBO J.* 7:1003–1011.

Hart et al. (1989) "Expression of Secreted Human Immunoglobulin/PDGF–Receptor Fusion Proteins Which Demonstrate High Affinity Ligand Binding" *Miami Winter Cancer Symposium*.

Heldin et al. (1988) "Binding of different dimeric forms of PDGF to human fibroblast: evidence for two separate receptor types" *EMBO J.* 7:1387–1393.

Daniel et al. (1987) "Biosynthetic and Glycosylation Studies of Cell Surface Platelet–Derived Growth Factor Receptors" *J. Biol. Chem.* 262:9778–9784.

Keating et al. (1989) "Platelet–Derived Growth Factor Receptor Inducibility Is Acquired Immediately after Translation and Does Not Require Glycosylation" *J. Biol. Chem.* 264:9129–9132.

Keating et al. (1988) "Autocrine Stimulation of Intracellular PDGF Receptors in v–sis–Transformed Cells" *Science* 239:914–916.

Hart et al. (1987) "Synthesis, Phosphorylation, and Degradation of Multiple Forms of the Platelet–Derived Growth Factor Receptor Studied Using a Monoclonal Antibody" *J. Biol. Chem.* 262:10780–10785.

Bell et al. (1989) "Effect of Platelet Factors on Migration of Cultured Bovine Aortic Endothelial and Smooth Muscle Cells" *Circulation Research* 65:1057–1065.

Ronnstrand et al. (1987) "Purification of the Receptor for Platelet–Derived Growth Factor from Porcine Uterus" *J. Biol. Chem.* 262:2929–2932.

Felder et al. (1990) "Kinase Activity Controls the Sorting of the Epidermal Growth Factor Receptor within the Multivesicular Body" *Cell* 61:623–634.

Orchansky et al. (1988) "Phosphatidylinositol Linkage of a Truncated Form of the Platelet–Derived Growth Factor Receptor" *J. Biol. Chem.* 263: 15159–15165.

Kimball et al. (1984) "Epidermal Growth Factor (EGF) Binding to Membranes Immobilized in Microtiter Wells and Estimation of EGF–Related Transforming Growth Factor Activity" *Biochem. Biophys. Acta* 771:82–88.

van der Schaal et al. (1984) "An Enzyme–Linked Lectin Binding Assay for Quantitative Determination of Lectin Receptors" *Anal. Biochem.* 140:48–55.

van Driel et al. (1989) "Stoichiometric Binding of Low Density Lipoprotein (LDL) Monoclonal Antibodies to LDL Receptors in a Solid Phase Assay" *J. Biol. Chem.* 264:2533–9538.

Williams et al. (1982) "Platelet–Derived growth factor binds specifically to receptors on vascular smooth muscle cells and the binding becomes nondissociable" *Proc. Nat'l Acad. Sci. USA* 79:5867–5870.

Williams et al. (1984) "Platelet–Derived Growth Factor Receptors Form a High Affinity State in Membrane Preparations" *J. Biol. Chem.* 259:5287–5294.

Anderson et al. (1990) "Binding of SH2 Domains of Phospholipase cλ1, GAP, and Src to Activated Growth Factor Receptors" *Science* 250:979–982.

Coughlin et al. (1989) "Role of Phosphatidylinositol Kinase in PDGF Receptor Signal Transduction" *Science* 243:1191–1194.

Escobedo et al. (1988) "A PDGF receptor domain essential for mitogenesis but not for many other responses to PDGF" *Nature* 335:85–87.

Williams et al. (1988) "Signal Transduction by the Platelet–Derived Growth Factor Receptor" *CSH Symp. Quant. Biol.* 53:455–465.

Morrison et al. (1989) "Direct Activation of the Serine/Threonine Kinase Activity of Raf–1 through Tyrosine Phosphorylation by the PDGF β–Receptor" *Cell* 58:649–657.

Keating et al. (1988) "Ligand Activation Causes a Phosphorylation–dependent Change in Platelet–Derived Growth Factor Receptor Conformation" *J. Biol. Chem.* 263:12805–12808.

Morrison et al. (1990) "Platelet–Derived Growth Factor (PDGF)–Dependent Associated of Phospholipase c–Y with the PDGF Receptor Signaling Complex" *Mol. Cell. Biol.* 10:2359–2366.

Kaplan et al. (1990) "PDGF β–Receptor Stimulates Tyrosine Phosphorylation of GAP and Association of GAP with a Signaling Complex" *Cell* 61:125–133.

Roussel et al. (1987) "Transforming potential of the c–fms proto–oncogene (CSF–1 receptor)" *Nature* 325:549–552.

Moran et al. (1990) "Src homology region 2 domains direct protein–protein interactions in signal transduction" *Proc. Nat'l Acad. Sci. USA* 87:8622–8626.

Kypta et al.(1990) "Association between the PDGF Receptor and members of the *src* Family of Tyrosine Kinases" *Cell* 62:481–492.

Nishibe et al. (1990) "Increase of the Catalytic Activity of Phospholipase c–Y1 by Tyrosine Phosphorylation" *Science* 250:1253–1256.

Heidaran et al. (1990) "Chimeric α– and β–Platelet–Derived Growth Factor (PDGF) Receptors Define Three Immunoglobulin–like Domains of the α–PDGF Receptor That Determine PDGF–AA Binding Specificity" *J. Biol. Chem.* 265:18741–18744.

Marx (1990) "Oncogenes Evoke New Cancer Therapies" *Science* 249:1376–1378.

Keating et al. (1987) "Processing of the Platelet–Derived Growth Factor Receptor" *J. Biol. Chem.* 262:7932–7937.

Bishayee et al. (1989) "Ligand–induced dimerization of the Platelet–Derived Growth Factor Receptor" *J. Biol. Chem.* 264:11699–11705.

Seifert et al. (1989) "Two Different Subunits Associate to Create Isoform–specific Platelet–Derived Growth Factor Receptors" *J. Biol. Chem.* 264:8771–8778.

Nister et al. (1988) "A Glioma–Derived PDGF A Chain Homodimer Has Different Functional Activities from a PDGF AB Heterodimer Purified from Human Platelets" *Cell* 52:791–799.

Williams (1989) "Signal Transduction by the Platelet–Derived Growth Factor Receptor Involves Association of the Receptor with Cytoplasmic Molecules" *Clinical Research* 37:564–568.

Heldin et al. (1989) "Dimerization of B–type Platelet–Derived Growth Factor Receptors Occurs after Ligand Binding and Is Closely Associated with Receptor Kinase Activation" *J. Biol. Chem.* 264:8905–8912.

DOMAINS OF EXTRACELLULAR REGION OF HUMAN PLATELET DERIVED GROWTH FACTOR RECEPTOR POLYPEPTIDES

This is a Continuation of application Ser. No. 07/650,793, filed Jan. 31, 1991, now abandoned.

FIELD OF THE INVENTION

The present invention relates to receptors for growth factors, particularly to human platelet-derived growth factor receptors (hPDGF-R). More particularly, it provides various composite constructs of human platelet-derived growth factor receptors, these constructs retaining ligand binding regions found in the natural extracellular region of the receptors. It also provides recombinant nucleic acids encoding these polypeptides, typically also comprising a promoter for expression, and fusion peptides on the amino or carboxy terminus of the expressed extracellular composite structure. Antibodies are provided which recognize epitopes containing amino acids contained in different domains of the extracellular region. Cells comprising these polypeptides and nucleic acids, and diagnostic uses of these reagents are also provided.

BACKGROUND OF THE INVENTION

Polypeptide growth factors are mitogens that act on cells by specifically binding to receptors located on the cell plasma membrane. The platelet-derived growth factor (PDGF) stimulates a diverse group of biochemical responses, e.g., changes in ion fluxes, activation of various kinases, alteration of cell shape, transcription of various genes, and modulation of enzymatic activities associated with phospholipid metabolism. See, e.g., Bell et al. (1989) "Effects of Platelet Factors on Migration of Cultured Bovine Aortic Endothelial and Smooth Muscle Cells," *Circulation Research* 65:1057–1065.

Platelet-derived growth factors are found in higher animals, particularly in warm blooded animals, e.g., mammals. In vitro, PDGF is a major polypeptide mitogen in serum for cells of mesenchymal origin such as fibroblasts, smooth muscle cells, and glial cells. In vivo, PDGF does not normally circulate freely in blood, but is stored in the alpha granules of circulating blood platelets. During blood clotting and platelet adhesion the granules are released, often at sites of injured blood vessels, thereby implicating PDGF in the repair of blood vessels. PDGF may stimulate migration of arterial smooth muscle cells from the medial to the intimal layer of the artery where the muscle cells may proliferate. This is likely to be an early response to injury.

PDGF has also been implicated in wound healing, in atherosclerosis, in myeloproliferative disease, and in stimulating genes associated with cancerous transformation of cells, particularly c-myc and c-fos.

The platelet-derived growth factor is composed of two homologous polypeptide chains; it is a dimer of 16 kilodalton proteins which are disulfide connected. These polypeptides are of two types, the type B chain and the type A chain. Three forms of the growth factor dimer are found corresponding to a homodimer of two type A chains, a homodimer of two type B chains, and a heterodimer of the type A chain with the type B chain. Each of these three different combinations is referred to as a PDGF isoform. See, for a review on PDGF, Ross et al. (1986) "The Biology of Platelet-Derived Growth Factor," *Cell* 46:155–169. The growth factor sequences from mouse and human are highly homologous.

The PDGF acts by binding to the platelet-derived growth factor receptor (PDGF-R). The receptor is typically found on cells of mesenchymal origin. The functional receptor acts while in a form comprising of two transmembrane glycoproteins, each of which is about 180 kilodaltons. Two different polypeptides have been isolated, a type B receptor polypeptide and a type A receptor polypeptide.

A sequence of a type B receptor polypeptide of the mouse platelet-derived growth factor receptor polypeptide is published in Yarden et al. (1986) *Nature* 323:226–232. A sequence of an type A human platelet-derived growth factor receptor (hPDGF-R) polypeptide is disclosed in Matsui et al. (1989) *Science* 243: 800–803.

These PDGF receptors usually have three major identifiable regions. The first is a transmembrane region (TM) which spans the plasma membrane once, separating the regions of the receptor exterior to the cell from the regions interior to the cell. The second region is an extracellular region (XR) which contains the domains that bind the polypeptide growth factor (i.e., the ligand binding domains). The third is an intracellular region (IR) which possesses a tyrosine kinase activity. This tyrosine kinase domain is notable in having an insert of about 100 amino acids, as compared with most other receptor tyrosine kinase domains which are contiguous or have shorter insert segments.

The complete sequences of the human type B and human type A receptor polypeptides are reported elsewhere. e.g., application Ser. No. 07/771,829 which is a continuation of Ser. No. 07/309,332, now abandoned. However, for many purposes, a smaller or less than full length functional protein would be desired. For example, smaller molecules may be more easily targeted to areas of compromised circulation, or present fewer epitopes or extraneous domains unrelated to various activities of interest. Functional analogues with a slightly modified spectrum of activity, or different specificity would be very useful.

Thus, the use of new composite constructs exhibiting biological activity in common with platelet-derived growth factor receptor polypeptides will have substantial use as research reagents, diagnostic reagents, and therapeutic reagents. In particular, the identification of important polypeptide features in the extracellular region of the platelet-derived growth factor receptor polypeptides will allow substitutions and deletions of particular features of the domains. Moreover, use of an in vitro assay system provides the ability to test cytotoxic or membrane disruptive compounds.

SUMMARY OF THE INVENTION

In accordance with the present invention, defined constructs of modified human platelet-derived growth factor receptor polypeptides are provided. Extracellular region domain structures are identified and modifications and combinatorial rearrangements of the receptor segments are furnished. Both cell bound and soluble forms of modified segments are made available, as are methods for assays using them, thereby allowing for screening of ligand analogues.

The present invention provides a platelet-derived growth factor receptor (hPDGF-R) fragment of between about 8 and 400 amino acids comprising one or more platelet-derived growth factor (PDGF) ligand binding regions (LBR's) from extracellular domains D1, D2, or D3, wherein the fragment binds a platelet-derived growth factor ligand. Generally, the fragment will exhibit a binding affinity of about 5 nM or better and will have a sequence of at least about 6 or 8 contiguous amino acids, preferably at least about 15 or more contiguous amino acids from a domain D3 intra-cysteine region. The fragment will often lack a transmembrane region. In other embodiments, the fragment is soluble, is substantially pure, or has at least one ligand binding region derived from a domain D3. The fragment may be derived from a type B, or from a type A PDGF-R LBR fragment, e.g., from Table 1 or Table 2. In particular embodiments, the fragment is selected from the group of formulae consisting of:

a) Xa-Dm-Xc;

b) Xa-Dm-X1-Dn-Xc;

c) Xa-Dm-X1-Dn-X2-Dp-Xc; and d) Xa-Dm-X1-Dn-X2-Dp-X3-Dq-Xc;

e) Xa-Dm-X1-Dn-X2-Dp-X3-Dq-X4-Dr-Xc;

where the fragment is not D1-D2-D3-D4-D5;

each of Xa, X1, X2, X3, and Xc is, if present, a polypeptide segment lacking a D domain; and each of Dm, Dn, Dp, and Dq is, independently of one another, selected from the group consisting of D1, D2, D3, D4, and D5. Preferred fragments are selected from the group consisting of:

a) D1-D2-D3 or D3-D4-D5; and b) D1-D2-D3-D4 or D2-D3-D4-D5.

The present invention also embraces a soluble human platelet-derived growth factor receptor (hPDGF-R) fragment of between about 10 and 350 amino acids comprising at least one platelet-derived growth factor (PDGF) ligand binding region (LBR) from a domain D3, wherein the fragment specifically binds to a platelet-derived growth factor ligand. Usually the fragment comprises a sequence of at least about 15 contiguous amino acids from the intra-cysteine portion of domain D3 and has a binding affinity of better than about 5 nM. Other useful fragment embodiments will be soluble, substantially pure, or a type B or type A PDGF-R LBR, e.g., from Table 1 or Table 2.

The invention also includes nucleic acid sequences, including those encoding the above described polypeptide fragments. Often the nucleic acid sequences incorporate a promoter, generally operably linked to the sequence encoding the fragments.

Cells comprising the nucleic acids or peptides of the invention are also embraced. In particular cell embodiments, the cell will be a mammalian cell, and often will contain both a nucleic acid and a protein expression product of the nucleic acid.

The compositions described above provide antibodies which recognize an epitope of a described PDGF-R fragment, but not a natural PDGF-R epitope. The antibody will often be a monoclonal antibody.

The present invention also provides a method for measuring the PDGF receptor binding activity of a biological sample comprising the steps of:

a) contacting an aliquot of a sample to a PDGF ligand in the presence of a described PDGF-R fragment in a first analysis;

b) contacting an aliquot of the sample to a PDGF ligand in the absence of the PDGF-R fragment in a second analysis; and c) comparing the amount of binding in the two analyses. In some instances, the PDGF-R fragment is attached to a cell, or a solid substrate, e.g., a microtiter dish.

The invention also embraces a method for measuring the PDGF ligand content of a biological sample comprising the steps of:

a) contacting an aliquot of the sample to a ligand binding region (LBR) in the presence of a described PDGF-R fragment in a first analysis;

b) contacting an aliquot of the sample to a LBR in the absence of the PDGF-R fragment in a second analysis; and c) comparing the amount of binding in the two analyses. In some embodiments, the contacting steps are performed simultaneously.

BRIEF DESCRIPTION OF THE DRAWINGS

FIG. 1 illustrates a strategy for oligonucleotide directed in vitro deletion mutagenesis of soluble hPDGF-R extracellular domains. Many of these constructs will be soluble peptides, or can be modified to be such.

The abbreviations used are:

| | |
|---|---|
| PR | = PDGF-R; intact |
| P | = PDGF-R; extracellular region |
| TM | = transmembrane |
| K | = kinase |
| S | = signal sequence |

FIG. 2 illustrates the structure of a plasmid derived form pcDL-S$\alpha$296 used for expressing various deletion polypeptides.

FIG. 3 illustrates the structure of a plasmid pBJ$\Delta$ derived from pcDL$\alpha$296. See Takabe et al. (1988) *Mol. Cell. Biol.* 8:466–472.

1. The pcDL-SR$\alpha$296 is cut with XhoI.

2. A polylinker (XhoI-XbaI-SfiI-NotI-EcoRI-EcoRV-HindIII-ClaI-SalI) is inserted into the XhoI cut vector.

3. SalI is compatible with the XhoI site; and generates both a SalI and an XhoI site.

4. The SV40 16s splice junction is no longer present.

FIG. 4 illustrates the inhibition of receptor phosphorylation by a human type B PDGF receptor polypeptide. Labeling with a reagent which binds to phosphorylated tyrosine shows that phosphorylation activity is decreased in the presence of the receptor polypeptide fragment.

DETAILED DESCRIPTION OF THE PREFERRED EMBODIMENT

I. General Description
- A. PDGF-R
  - 1. structural features
    - a. extracellular domain (XR)
      - i. signal sequence
      - ii. D domains (Ig-like)
    - b. transmembrane segment (TM)
    - c. intracellular domain (IR)
      - i. tyrosine kinase
      - ii. insert
  - 2. function
    - a. bind ligands (PDGF analogues)
    - b. tyrosine kinase activity
    - c. bind to PDGF-R peptide (dimer formation)
    - d. phosphorylated segments
- B. Physiological Functions
  - 1. cellular
  - 2. tissue differentiation
  - 3. organismal II. Polypeptides A. D domains
   1. β-sheet strands
   2. cysteine residues
  B. Soluble Forms, extracellular region
  C. Truncated/Deletion Forms
  D. Fusion Proteins
  E. Genetic Variants (site-directed mutagenized)
  F. Compositions Comprising Proteins
III. Nucleic Acids
  A. Isolated Nucleic Acids
  B. Recombinant Nucleic Acids
  C. Compositions Comprising Nucleic Acids
IV. Methods for Making PDGF-R Constructs
  A. Protein Purification
   1. affinity with derivatized PDGF
   2. various ligands, same receptor
  B. Expression of Nucleic Acids
  C. Synthetic methods
V. Antibodies
VI. Methods for Use
  A. Diagnostic
  B. Therapeutic
I. General Description
  A. Platelet-derived growth factor receptor (PDGF-R)

The human platelet-derived growth factor receptor (hPDGF-R) typically comprises two polypeptides. These polypeptides, which may be identical or only slightly different, associate during the functional activities of ligand binding and transducing of the ligand binding signal into the cell.

The platelet-derived growth factor receptor was identified as having a major component of an approximately 180 kilodalton protein which is glycosylated. This glycoprotein was identified as a platelet-derived growth factor receptor polypeptide. Primary structures of two homologous forms of polypeptides have been reported. A type B receptor nucleic acid and its corresponding polypeptide sequence from mouse are reported in Yarden et al. (1986) *Nature* 323: 226-232; and a homologous genetic sequence has been isolated from humans. See application Ser. No. 07/771,829 which is a continuation of Ser. No. 07/309,332, now abandoned. A human type A receptor sequence is reported in Matsui et al. (1989) *Science* 243: 800-803. Although the two different forms of the receptor polypeptides are homologous, they are encoded by two separate genes.

The functional receptor apparently involves a dimer of these polypeptides, either homodimers of the type B receptor polypeptide or of the type A receptor polypeptide, or a heterodimer of the type B receptor polypeptide with an type A receptor polypeptide. The specificity of binding of each of these forms of the receptor is different for each of the different forms of platelet-derived growth factor (PDGF), the AA, BB, or AB forms (from either mouse or human, or presumably other mammals).

The PDGF-R is a member of a family of related receptors. See, e.g., Yarden et al. supra. Each of these receptor polypeptides has a hydrophobic membrane spanning region (TM for transmembrane), a large extracellular region (XR) with regularly spaced cystine residues, and a cytoplasmic intracellular region (IR) having intracellular tyrosine kinase activity. The XR of the PDGF-R has a predicted structure containing 5 β-strand-rich immunoglobulin (Ig)-like domains. Each of these Ig-like domains consists of about 100 amino acids, ranging more specifically from about 88 to about 114 amino acids, and, except for the fourth domain, contains regularly spaced cysteine residues. Many of the structural features of the various growth factor receptors are homologous, including the mouse and human versions of the PDGF-R. Thus, many of the structural features defined herein are shared with other related proteins. However, in most cases, the functional relationship to particular structural features is unknown.

The intracellular region (IR) is that segment of the PDGF-R which is carboxy proximal of the transmembrane (TM) segment. The intracellular region is characterized, in part, by the presence of a split tyrosine kinase structural domain. In the human type B receptor polypeptide, the tyrosine kinase domain is about 244 amino acids with an insert of about 104 amino acids. See Table 1. In the human type A receptor polypeptide, the domain is about 244 amino acids long with a kinase insert of about 103 amino acids. See Table 2. Functionally, this domain is defined, in part, by its tyrosine kinase activity, typically modulated by ligand binding to binding sites found in the extracellular region, and appears to function in a dimer state. The substrate for phosphorylation includes various tyrosine residues on the accompanying receptor polypeptide chain, and other proteins which associate with the receptor. The tyrosine kinase domain is also defined, in part, by its homology to similar domains in other tyrosine kinase activity containing proteins. See, e.g., Yarden et al. (1986) *Nature* 323:226–232. Each IR segment of the dimerized receptor complex appears to phosphorylate specific tyrosine residues on the other polypeptide chain.

Each transmembrane segment of the human receptor polypeptides is about 24 or 25 amino acids long and is characterized by hydrophobic amino acid residues. These segments have sequences characteristic of membrane spanning segments. In the human type B receptor polypeptide the transmembrane region appears about 25 amino acids long extending from about val(500) to trp(524), while in the human type A receptor polypeptide, the transmembrane segment appears to be about 24 amino acids extending from about leu(502) to trp(526). See, e.g., Claesson-Welsh et al. (1989) *Proc. Nat'l Acad. Sci. USA*, 86:4917–4921.

A polypeptide or nucleic acid is a "human" sequence if it is derived from, or originated in part from, a natural human source. For example, proteins derived from human cells, or originally encoded by a human genetic sequence, will be human proteins. A sequence is also human if it is selected on the basis of its high similarity to a sequence found in a natural human sample, or is derived therefrom.

A fusion polypeptide or nucleic acid is a molecule which results from the fusion of segments from sequences which are not naturally in continuity with one another. Thus, a chimeric protein or nucleic acid is a fusion molecule. A heterologous protein is a protein originating from a different source.

B. Physiological Functions

The PDGF-R appears to have at least four major different biological functions. The first is the binding of ligands, usually the PDGF mitogenic proteins or their analogues. These ligands and analogues may also serve as either agonists or antagonists. The ligand binding sites, made up of ligand binding regions (LBR's), are localized in the extracellular region (XR). The functional receptor transduces a signal in response to ligand binding, and the resulting response is a ligand modulated activity. As the likely ligand is a PDGF, or an analogue, the signal will ordinarily be PDGF modulated.

A second biological activity relates to the tyrosine kinase enzymatic activity. This activity is typically activated intracellularly in response to ligand binding. However, since these receptors apparently function in a dimeric state, the interchain binding interactions may be considered a third biological activity which may be mediated by blocking agents. Blocking or interference with the dimerization interactions may be mediated by receptor protein fragments, particularly in the functional ligand binding or tyrosine kinase activities. Thus, the introduction of analogues of the receptor domains to natural or other receptor polypeptides may serve as an additional means to affect PDGF mediation of ligand mediated activities.

The fourth function of the PDGF receptor is as a binding substrate for other proteins, e.g., the PI3 kinase. In particular, the PDGF receptor is phosphorylated at various positions in response to ligand binding or other events. This binding interaction activates an enzymatic activity on the part of the binding protein which activates further cellular or metabolic responses.

The term "ligand" refers to the molecules, usually members of the platelet-derived growth factor family, that are bound by the ligand binding regions (LBR's). The binding regions are typically found in the XR. Also, a ligand is a molecule that serves either as the natural ligand to which the receptor binds, or a functional analogue of a ligand. The analogue may serve as an agonist or antagonist. Typically ligands will be molecules which share structural features of natural PDGF, e.g., polypeptides having similar amino acid sequences or other molecules sharing molecular features with a ligand. The determination of whether a molecule serves as a ligand depends upon the measurement of a parameter or response which changes upon binding of that ligand, such as dimerization or tyrosine kinase activity. See, e.g., Gilman et al. (eds) (1990) *Goodman and Gilman's: The pharmacological Bases of Therapeutics*, 8th Ed., Pergamon Press, which is incorporated herein by reference.

The receptor has ligand binding regions (LBR), or regions which are important in determining both affinity and specificity of binding of ligand, e.g., PDGF and its analogues. The ligand binding regions determine the binding interactions between the receptors and ligand. Typically, these regions are those contact points between the ligand molecule and the receptor. These molecular interactions can be determined by crystallographic techniques, or by testing which regions of the receptor are important in ligand interaction. Various segments of the extracellular region of the PDGF receptor make up the ligand binding regions, while other segments form structural segments which spatially orient the LBR's in proper arrangement to properly bind the ligands.

Generally, the fragment will have a sequence of at least about 6 contiguous amino acids, usually at least about 8 contiguous amino acids, more usually at least about 10 contiguous amino acids, preferably at least about 13 contiguous amino acids, and more preferably at least about 15 or more contiguous amino acids. Usually, the LBR's will be located within the intra-cysteine (or equivalent) residues of each Ig-like domain, e.g., domains D1, D2, D3, D4, and D5. They will be preferably derived from D3 sequences, but D1 and D2 derived sequences will also be common. Occasionally, sequences from D4, D5, or other proteins will provide LBR function.

The extra-cysteine (or equivalent) regions provide structural functions, as will inter-domain spacer segments. The intra-cysteine portions, or segments, are indicated in Tables 4 and 5, and comprise the segments designated C, C', C", D, and E, along with portions of the B and F segments, as indicated. The extra-cysteine residues comprise the segments designated A and G, and portions of B and F.

The ligand binding regions as defined, in part, by the importance of their presence, or their effect on the affinity of PDGF ligand lending. The natural, native full length PDGF-R binds with a $K_d$ of about 0.2 nM. See, e.g., Duan et al. (1991) *J. Biol. Chem.* 266:413–418, which is hereby incorporated herein by reference. An LBR is a segment of polypeptide whose presence significantly affects ligand binding, generally by at least about a factor of two, usually by at least about a factor of four, more usually by at least a factor of about eight, and preferably by at least about a factor of twelve or more. A fragment of this invention which binds to the PDGF ligand will generally bind with a $K_d$ of less than about 10 μM, more generally less than about 1 μM, usually less than about 0.1 μM, more usually less than about 10 nM, preferably less than about 1 nM, and more preferably less than about 0.5 nM.

An epitope is an antigenic determinant which potentially or actually has elicited an antibody response. It may also refer to a structural feature which is defined by an antibody binding region, or its equivalent. An epitope need not necessarily be immunogenic, but will serve as a binding site for an antibody molecule or its equivalent.

II. Polypeptides

Table 1 discloses the sequence of one allele of a type B human platelet-derived growth factor receptor polypeptide. Both a nucleic acid sequence and its corresponding protein sequence are provided. The nucleic acid sequence corresponds to Seq. ID No. 1. The amino acid sequence corresponds to Seq. ID No. 2. A homologous mouse sequence was reported in Yarden et al. (1988) *Nature* 323:226–232. The sequence of a mouse PDGF receptor polypeptide also exhibits structural features in common with the regions, the domains, and the β-strand segments of the human receptor polypeptides. The mouse polypeptides, and those from other related receptors, will serve as a source of similar domains, homologous β-strand segments, and inter-segment sequences, and sequences of homology for general replacement or substitutions.

TABLE 1

| Sequence of one type B human PDGF receptor polypeptide allele and protein | |
|---|---|
| TGTTCTCCTGAGCCTTCAGGAGCCTGCACCAGTCCTGCCTGTCCTTCTACTC | 52 |
| AGCTGTTACCCACTCTGGGACCAGCAGTCTTTCTGATAACTGGGAGAGGGCAGTAAGGAGGACTTCC | 119 |
| TGGAGGGGGTGACTGTCCAGAGCCTGGAACTGTGCCCACACCAGAAGCCATCAGCAGCAAGGACACC | 186 |
| | |
| ATG CGG CTT CCG GGT GCG ATG CCA GCT CTG GCC CTC AAA GGC GAG CTG CTG | 237 |
| Met Arg Leu Pro Gly Ala Met Pro Ala Leu Ala Leu Lys Gly Glu Leu Leu | −15 |
| | |
| TTG CTG TCT CTC CTG TTA CTT CTG GAA CCA CAG ATC TCT CAG GGC CTG GTC | 288 |
| Leu Leu Ser Leu Leu Leu Leu Leu Glu Pro Gln Ile Ser Gln Gly Leu Val | 2 |

TABLE 1-continued Sequence of one type B human PDGF
receptor polypeptide allele and protein

| | |
|---|---|
| GTC ACA CCC CCG GGG CCA GAG CTT GTC CTC AAT GTC TCC AGC ACC TTC GTT<br>Val Thr Pro Pro Gly Pro Glu Leu Val Leu Asn Val Ser Ser Thr Phe Val | 339<br>19 |
| CTG ACC TGC TCG GGT TCA GCT CCG GTG GTG TGG GAA CGG ATG TCC CAG GAG<br>Leu Thr Cys Ser Gly Ser Ala Pro Val Val Trp Glu Arg Met Ser Gln Glu | 390<br>36 |
| CCC CCA CAG GAA ATG GCC AAG GCC CAG GAT GGC ACC TTC TCC AGC GTG CTC<br>Pro Pro Gln Glu Met Ala Lys Ala Gln Asp Gly Thr Phe Ser Ser Val Leu | 441<br>53 |
| ACA CTG ACC AAC CTC ACT GGG CTA GAC ACG GGA GAA TAC TTT TGC ACC CAC<br>Thr Leu Thr Asn Leu Thr Gly Leu Asp Thr Gly Glu Tyr Phe Cys Thr His | 492<br>70 |
| AAT GAC TCC CGT GGA CTG GAG ACC GAT GAG CGG AAA CGG CTC TAC ATC TTT<br>Asn Asp Ser Arg Gly Leu Glu Thr Asp Glu Arg Lys Arg Leu Tyr Ile Phe | 543<br>87 |
| GTG CCA GAT CCC ACC GTG GGC TTC CTC CCT AAT GAT GCC GAG GAA CTA TTC<br>Val Pro Asp Pro Thr Val Gly Phe Leu Pro Asn Asp Ala Glu Glu Leu Phe | 594<br>104 |
| ATC TTT CTC ACG GAA ATA ACT GAG ATC ACC ATT CCA TGC CGA GTA ACA GAC<br>Ile Phe Leu Thr Glu Ile Thr Glu Ile Thr Ile Pro Cys Arg Val Thr Asp | 645<br>121 |
| CCA CAG CTG GTG GTG ACA CTG CAC GAG AAG AAA GGG GAC GTT GCA CTG CCT<br>Pro Gln Leu Val Val Thr Leu His Glu Lys Lys Gly Asp Val Ala Leu Pro | 696<br>138 |
| GTC CCC TAT GAT CAC CAA CGT GGC TTT TCT GGT ATC TTT GAG GAC AGA AGC<br>Val Pro Tyr Asp His Gln Arg Gly Phe Ser Gly Ile Phe Glu Asp Arg Ser | 747<br>155 |
| TAC ATC TGC AAA ACC ACC ATT GGG GAC AGG GAG GTG GAT TCT GAT GCC TAC<br>Tyr Ile Cys Lys Thr Thr Ile Gly Asp Arg Glu Val Asp Ser Asp Ala Tyr | 798<br>172 |
| TAT GTC TAC AGA CTC CAG GTG TCA TCC ATC AAC GTC TCT GTG AAC GCA GTG<br>Tyr Val Tyr Arg Leu Gln Val Ser Ser Ile Asn Val Ser Val Asn Ala Val | 849<br>189 |
| CAG ACT GTG GTC CGC CAG GGT GAG AAC ATC ACC CTC ATG TGC ATT GTG ATC<br>Gln Thr Val Val Arg Gln Gly Glu Asn Ile Thr Leu Met Cys Ile Val Ile | 900<br>206 |
| GGG AAT GAT GTG GTC AAC TTC GAG TGG ACA TAC CCC CGC AAA GAA AGT GGG<br>Gly Asn Asp Val Val Asn Phe Glu Trp Thr Tyr Pro Arg Lys Glu Ser Gly | 951<br>223 |
| CGG CTG GTG GAG CCG GTG ACT GAC TTC CTC TTG GAT ATG CCT TAC CAC ATC<br>Arg Leu Val Glu Pro Val Thr Asp Phe Leu Leu Asp Met Pro Tyr His Ile | 1002<br>240 |
| CGC TCC ATC CTG CAC ATC CCC AGT GCC GAG TTA GAA GAC TCG GGG ACC TAC<br>Arg Ser Ile Leu His Ile Pro Ser Ala Glu Leu Glu Asp Ser Gly Thr Tyr | 1053<br>257 |
| ACC TGC AAT GTG ACG GAG AGT GTG AAT GAC CAT CAG GAT GAA AAG GCC ATC<br>Thr Cys Asn Val Thr Glu Ser Val Asn Asp His Gln Asp Glu Lys Ala Ile | 1104<br>274 |
| AAC ATC ACC GTG GTT GAG AGC GGC TAC GTG CGG CTC CTG GGA GAG GTG GGC<br>Asn Ile Thr Val Val Glu Ser Gly Tyr Val Arg Leu Leu Gly Glu Val Gly | 1155<br>291 |
| ACA CTA CAA TTT GCT GAG CTG CAT CGG AGC CGG ACA CTG CAG GTA GTG TTC<br>Thr Leu Gln Phe Ala Glu Leu His Arg Ser Arg Thr Leu Gln Val Val Phe | 1206<br>308 |
| GAG GCC TAC CCA CCG CCC ACT GTC CTG TGG TTC AAA GAC AAC CGC ACC CTG<br>Glu Ala Tyr Pro Pro Pro Thr Val Leu Trp Phe Lys Asp Asn Arg Thr Leu | 1257<br>325 |
| GGC GAC TCC AGC GCT GGC GAA ATC GCC CTG TCC ACG CGC AAC GTG TCG GAG<br>Gly Asp Ser Ser Ala Gly Glu Ile Ala Leu Ser Thr Arg Asn Val Ser Glu | 1308<br>342 |
| ACC CGG TAT GTG TCA GAG CTG ACA CTG GTT CGC GTG AAG GTG GCA GAG GCT<br>Thr Arg Tyr Val Ser Glu Leu Thr Leu Val Arg Val Lys Val Ala Glu Ala | 1359<br>359 |
| GGC CAC TAC ACC ATG CGG GCC TTC CAT GAG GAT GCT GAG GTC CAG CTC TCC<br>Gly His Tyr Thr Met Arg Ala Phe His Glu Asp Ala Glu Val Gln Leu Ser | 1410<br>376 |
| TTC CAG CTA CAG ATC AAT GTC CCT GTC CGA GTG CTG GAG CTA AGT GAG AGC<br>Phe Gln Leu Gln Ile Asn Val Pro Val Arg Val Leu Glu Leu Ser Glu Ser | 1461<br>393 |
| CAC CCT GAC AGT GGG GAA CAG ACA GTC CGC TGT CGT GGC CGG GGC ATG CCG<br>His Pro Asp Ser Gly Glu Gln Thr Val Arg Cys Arg Gly Arg Gly Met Pro | 1512<br>410 |
| CAG CCG AAC ATC ATC TGG TCT GCC TGC AGA GAC CTC AAA AGG TGT CCA CGT<br>Gln Pro Asn Ile Ile Trp Ser Ala Cys Arg Asp Leu Lys Arg Cys Pro Arg | 1563<br>427 |
| GAG CTG CCG CCC ACG CTG CTG GGG AAC AGT TCC GAA GAG GAG AGC CAG CTG | 1614 |

TABLE 1-continued

| Sequence of one type B human PDGF receptor polypeptide allele and protein | |
|---|---|
| Glu Leu Pro Pro Thr Leu Leu Gly Asn Ser Ser Glu Glu Glu Ser Gln Leu | 444 |
| GAG ACT AAC GTG ACG TAC TGG GAG GAG GAG CAG GAG TTT GAG GTG GTG AGC<br>Glu Thr Asn Val Thr Tyr Trp Glu Glu Glu Gln Glu Phe Glu Val Val Ser | 1665<br>461 |
| ACA CTG CGT CTG CAG CAC GTG GAT CGG CCA CTG TCG GTG CGC TGC ACG CTG<br>Thr Leu Arg Leu Gln His Val Asp Arg Pro Leu Ser Val Arg Cys Thr Leu | 1716<br>478 |
| CGC AAC GCT GTG GGC CAG GAC ACG CAG GAG GTC ATC GTG GTG CCA CAC TCC<br>Arg Asn Ala Val Gly Gln Asp Thr Gln Glu Val Ile Val Val Pro His Ser | 1767<br>495 |
| TTG CCC TTT AAG GTG GTG GTG ATC TCA GCC ATC CTG GCC CTG GTG GTG CTC<br>Leu Pro Phe Lys Val Val Val Ile Ser Ala Ile Leu Ala Leu Val Val Leu | 1818<br>512 |
| ACC ATC ATC TCC CTT ATC ATC CTC ATC ATG CTT TGG CAG AAG AAG CCA CGT<br>Thr Ile Ile Ser Leu Ile Ile Leu Ile Met Leu Trp Gln Lys Lys Pro Arg | 1869<br>529 |
| TAC GAG ATC CGA TGG AAG GTG ATT GAG TCT GTG AGC TCT GAC GGC CAT GAG<br>Tyr Glu Ile Arg Trp Lys Val Ile Glu Ser Val Ser Ser Asp Gly His Glu | 1920<br>546 |
| TAC ATC TAC GTG GAC CCC ATG CAG CTG CCC TAT GAC TCC ACG TGG GAG CTG<br>Tyr Ile Tyr Val Asp Pro Met Gln Leu Pro Tyr Asp Ser Thr Trp Glu Leu | 1971<br>563 |
| CCG CGG GAC CAG CTT GTG CTG GGA CGC ACC CTC GGC TCT GGG GCC TTT GGG<br>Pro Arg Asp Gln Leu Val Leu Gly Arg Thr Leu Gly Ser Gly Ala Phe Gly | 2022<br>580 |
| CAG GTG GTG GAG GCC ACA GCT CAT GGT CTG AGC CAT TCT CAG GCC ACG ATG<br>Gln Val Val Glu Ala Thr Ala His Gly Leu Ser His Ser Gln Ala Thr Met | 2073<br>597 |
| AAA GTG GCC GTC AAG ATG CTT AAA TCC ACA GCC CGC AGC AGT GAG AAG CAA<br>Lys Val Ala Val Lys Met Leu Lys Ser Thr Ala Arg Ser Ser Glu Lys Gln | 2124<br>614 |
| GCC CTT ATG TCG GAG CTG AAG ATC ATG AGT CAC CTT GGG CCC CAC CTG AAC<br>Ala Leu Met Ser Glu Leu Lys Ile Met Ser His Leu Gly Pro His Leu Asn | 2175<br>631 |
| GTG GTC AAC CTG TTG GGG GCC TGC ACC AAA GGA GGA CCC ATC TAT ATC ATC<br>Val Val Asn Leu Leu Gly Ala Cys Thr Lys Gly Gly Pro Ile Tyr Ile Ile | 2226<br>648 |
| ACT GAG TAC TGC CGC TAC GGA GAC CTG GTG GAC TAC CTG CAC CGC AAC AAA<br>Thr Glu Tyr Cys Arg Tyr Gly Asp Leu Val Asp Tyr Leu His Arg Asn Lys | 2277<br>665 |
| CAC ACC TTC CTG CAG CAC CAC TCC GAC AAG CGC CGC CCG CCC AGC GCG GAG<br>His Thr Phe Leu Gln His His Ser Asp Lys Arg Arg Pro Pro Ser Ala Glu | 2328<br>682 |
| CTC TAC AGC AAT GCT CTG CCC GTT GGG CTC CCC CTG CCC AGC CAT GTG TCC<br>Leu Tyr Ser Asn Ala Leu Pro Val Gly Leu Pro Leu Pro Ser His Val Ser | 2379<br>699 |
| TTG ACC GGG GAG AGC GAC GGT GGC TAC ATG GAC ATG AGC AAG GAC GAG TCG<br>Leu Thr Gly Glu Ser Asp Gly Gly Tyr Met Asp Met Ser Lys Asp Glu Ser | 2430<br>716 |
| GTG GAC TAT GTG CCC ATG CTG GAC ATG AAA GGA GAC GTC AAA TAT GCA GAC<br>Val Asp Tyr Val Pro Met Leu Asp Met Lys Gly Asp Val Lys Tyr Ala Asp | 2481<br>733 |
| ATC GAG TCC TCC AAC TAC ATG GCC CCT TAC GAT AAC TAC GTT CCC TCT GCC<br>Ile Glu Ser Ser Asn Tyr Met Ala Pro Tyr Asp Asn Tyr Val Pro Ser Ala | 2532<br>750 |
| CCT GAG AGG ACC TGC CGA GCA ACT TTG ATC AAC GAG TCT CCA GTG CTA AGC<br>Pro Glu Arg Thr Cys Arg Ala Thr Leu Ile Asn Glu Ser Pro Val Leu Ser | 2583<br>767 |
| TAC ATG GAC CTC GTG GGC TTC AGC TAC CAG GTG GCC AAT GGC ATG GAG TTT<br>Tyr Met Asp Leu Val Gly Phe Ser Tyr Gln Val Ala Asn Gly Met Glu Phe | 2634<br>784 |
| CTG GCC TCC AAG AAC TGC GTC CAC AGA GAC CTG GCG GCT AGG AAC GTG CTC<br>Leu Ala Ser Lys Asn Cys Val His Arg Asp Leu Ala Ala Arg Asn Val Leu | 2685<br>801 |
| ATC TGT GAA GGC AAG CTG GTC AAG ATC TGT GAC TTT GGC CTG GCT CGA GAC<br>Ile Cys Glu Gly Lys Leu Val Lys Ile Cys Asp Phe Gly Leu Ala Arg Asp | 2736<br>818 |
| ATC ATG CGG GAC TCG AAT TAC ATC TCC AAA GGC AGC ACC TTT TTG CCT TTA<br>Ile Met Arg Asp Ser Asn Tyr Ile Ser Lys Gly Ser Thr Phe Leu Pro Leu | 2787<br>835 |
| AAG TGG ATG GCT CCG GAG AGC ATC TTC AAC AGC CTC TAC ACC ACC CTG AGC<br>Lys Trp Met Ala Pro Glu Ser Ile Phe Asn Ser Leu Tyr Thr Thr Leu Ser | 2838<br>852 |
| GAC GTG TGG TCC TTC GGG ATC CTG CTC TGG GAG ATC TTC ACC TTG GGT GGC<br>Asp Val Trp Ser Phe Gly Ile Leu Leu Trp Glu Ile Phe Thr Leu Gly Gly | 2889<br>869 |

TABLE 1-continued

Sequence of one type B human PDGF receptor polypeptide allele and protein

| | |
|---|---|
| ACC CCT TAC CCA GAG CTG CCC ATG AAC GAG CAG TTC TAC AAT GCC ATC AAA<br>Thr Pro Tyr Pro Glu Leu Pro Met Asn Glu Gln Phe Tyr Asn Ala Ile Lys | 2940<br>886 |
| CGG GGT TAC CGC ATG GCC CAG CCT GCC CAT GCC TCC GAC GAG ATC TAT GAG<br>Arg Gly Tyr Arg Met Ala Gln Pro Ala His Ala Ser Asp Glu Ile Tyr Glu | 2991<br>903 |
| ATC ATG CAG AAG TGC TGG GAA GAG AAG TTT GAG ATT CGG CCC CCC TTC TCC<br>Ile Met Gln Lys Cys Trp Glu Glu Lys Phe Glu Ile Arg Pro Pro Phe Ser | 3042<br>920 |
| CAG CTG GTG CTG CTT CTC GAG AGA CTG TTG GGC GAA GGT TAC AAA AAG AAG<br>Gln Leu Val Leu Leu Leu Glu Arg Leu Leu Gly Glu Gly Tyr Lys Lys Lys | 3093<br>937 |
| TAC CAG CAG GTG GAT GAG GAG TTT CTG AGG AGT GAC CAC CCA GCC ATC CTT<br>Tyr Gln Gln Val Asp Glu Glu Phe Leu Arg Ser Asp His Pro Ala Ile Leu | 3144<br>954 |
| CGG TCC CAG GCC CGC TTG CCT GGG TTC CAT GGC CTC CGA TCT CCC CTG GAC<br>Arg Ser Gln Ala Arg Leu Pro Gly Phe His Gly Leu Arg Ser Pro Leu Asp | 3195<br>971 |
| ACC AGC TCC GTC CTC TAT ACT GCC GTG CAG CCC AAT GAG GGT GAC AAC GAC<br>Thr Ser Ser Val Leu Tyr Thr Ala Val Gln Pro Asn Glu Gly Asp Asn Asp | 3246<br>989 |
| TAT ATC ATC CCC CTG CCT GAC CCC AAA CCT GAG GTT GCT GAC GAG GGC CCA<br>Tyr Ile Ile Pro Leu Pro Asp Pro Lys Pro Glu Val Ala Asp Glu Gly Pro | 3297<br>1005 |
| CTG GAG GGT TCC CCC AGC CTA GCC AGC TCC ACC CTG AAT GAA GTC AAC ACC<br>Leu Glu Gly Ser Pro Ser Leu Ala Ser Ser Thr Leu Asn Glu Val Asn Thr | 3348<br>1022 |
| TCC TCA ACC ATC TCC TGT GAC AGC CCC CTG GAG CCC CAG GAC GAA CCA GAG<br>Ser Ser Thr Ile Ser Cys Asp Ser Pro Leu Glu Pro Gln Asp Glu Pro Glu | 3399<br>1039 |
| CCA GAG CCC CAG CTT GAG CTC CAG GTG GAG CCG GAG CCG GAG CTG GAA CAG<br>Pro Glu Pro Gln Leu Glu Leu Gln Val Glu Pro Glu Pro Glu Leu Glu Gln | 3450<br>1056 |
| TTG CCG GAT TCG GGG TGC CCT GCC CCT CGG GCG GAA GCA GAG GAT AGC TTC<br>Leu Pro Asp Ser Gly Cys Pro Ala Pro Arg Ala Glu Ala Glu Asp Ser Phe | 3501<br>1073 |
| CTG TAGGGGGCTGGCCCCTACCCTGCCCTGCCTGAAGCTCCCCCGCTGCCAGCACCCAGCATCTCC<br>Leu | 3567<br>1074 |
| TGGCCTGGCCTGGCCGGGCTTCCTGTCAGCCAGGCTGCCCTTATCAGCTGTCCCCTTCTGGAAGCTT | 3634 |
| TCTGCTCCTGACGTGTTGTGCCCCAAACCCTGGGGCTGGCTTAGGAGGCAAGAAAACTGCAGGGGCC | 3701 |
| GTGACCAGCCCTCTGCCTCCAGGGAGGCCAACTGACTCTGAGCCAGGGTTCCCCCAGGGAACTCAGT | 3768 |
| TTTCCCATATGTAAGATGGGAAAGTTAGGCTTGATGACCCAGAATCTAGGATTCTCTCCCTGGCTGA | 3835 |
| CAGGTGGGGAGACCGAATCCCTCCCTGGGAAGATTCTTGGAGTTACTGAGGTGGTAAATTAACTTTT | 3902 |
| TTCTGTTCAGCCAGCTACCCCTCAAGGAATCATAGCTCTCTCCTCGCCACTTTTATCCACCCAGGAGC | 3969 |
| TAGGGAAGAGACCCTAGCCTCCCTGGCTGCTGGCTGAGCTAGGGCCTAGCCTTGAGCAGTGTTGCCT | 4036 |
| CATCCAGAAGAAAGCCAGTCTCCTCCCTATGATGCCAGTCCCTGCGTTCCCTGGCCCGAGCTGGTCT | 4103 |
| GGGGCCATTAGGCAGCCTAATTAATGCTGGAGGCTGAGCCAAGTACAGGACACCCCCAGCCTGCAGC | 4170 |
| CCTTGCCCAGGGCACTTGGAGCACACGCAGCCATAGCAAGTGCCTGTGTCCCTGTCCTTCAGGCCCA | 4237 |
| TCAGTCCTGGGGCTTTTTCTTTATCACCCTCAGTCTTAATCCATCCACCAGAGTCTAGAAGGCCAGA | 4304 |
| CGGGCCCCGCATCTGTGATGAGAATGTAAATGTGCCAGTGTGGAGTGGCCACGTGTGTGTGCCAGAT | 4371 |
| ATGGCCCTGGCTCTGCATTGGACCTGCTATGAGGCTTTGGAGGAATCCCTCACCCTCTCTGGGCCTC | 4438 |
| AGTTTCCCCTTCAAAAAATGAATAAGTCGGACTTATTAACTCTGAGTGCCTTGCCAGCACTAACATT | 4505 |
| CTAGAGTATCCAGGTGGTTGCACATTTGTCCAGATGAAGCAAGGCCATATACCCTAAACTTCCATCC | 4572 |
| TGGGGGTCAGCTGGGCTCCTGGGAGATTCCAGATCACACATCACACTCTGGGGACTCAGGAACCATG | 4639 |
| CCCCTTCCCCAGGCCCCCAGCAAGTCTCAAGAACACAGCTGCACAGGCCTTGACTTAGAGTGACAGC | 4706 |
| CGGTGTCCTGGAAAGCCCCCAGCAGCTGCCCCAGGGACATGGGAAGACCACGGGACCTCTTTCACTA | 4773 |
| CCCACGATGACCTCCGGGGGTATCCTGGGCAAAAGGGACAAAGAGGGCAAATGAGATCACCTCCTGC | 4840 |
| AGCCCACCACTCCAGCACCTGTGCCGAGGTCTGCGTCGAAGACAGAATGGACAGTGAGGACAGTTAT | 4907 |
| GTCTTGTAAAAGACAAGAAGCTTCAGATGGGTACCCCAAGAAGGATGTGAGAGGTGGGCGCTTTGGA | 4974 |
| GGTTTGCCCCTCACCCACCAGCTGCCCCATCCCTGAGGCAGCGCTCCATGGGGGTATGGTTTTGTCA | 5041 |
| CTGCCCAGACCTAGCAGTGACATCTCATTGTCCCCAGCCCAGTGGGCATTGGAGGTGCCAGGGGAGT | 5108 |
| CAGGGTTGTAGCCAAGACGCCCCCGCACGGGGAGGGTTGGGAAGGGGGTGCAGGAAGCTCAACCCCT | 5175 |
| CTGGGCACCAACCCTGCATTGCAGGTTGGCACCTTACTTCCCTGGGATCCCAGAGTTGGTCCAAGGA | 5242 |
| GGGAGAGTGGGTTCTCAATACGGTACCAAAGATATAATCACCTAGGTTTACAAATATTTTTAGGACT | 5309 |
| CACGTTAACTCACATTTATACAGCAGAAATGCTATTTTGTATGCTGTTAAGTTTTTCTATCTGTGTA | 5376 |
| CTTTTTTTTAAGGGAAAGATTTTAATATTAAACCTGGTGCTTCTCACTCAC | 5427 |

Table 2 discloses the sequence of an allele of an type A human platelet-derived growth factor receptor polypeptide. Both a nucleic acid sequence and its corresponding protein sequence are provided. The nucleic acid sequence corresponds to Seq. ID No. 5. The amino acid sequence corresponds to Seq. ID No. 4. Another human type A allele sequence is reported in Matsui et al. (1989) *Science* 243:800–803.

TABLE 2

Sequence of a human type A PDGF receptor polypetide allele and protein

| | | | | | | | | | | | | |
|---|---|---|---|---|---|---|---|---|---|---|---|---|
| TTGGAGCTACAGGGAGAGAAACAGAGGAGGAGACTGCAAGAGATCATTGGAGGCCGTGGGC | | | | | | | | | | | | 61 |
| ACGCTCTTTACTCCATGTGTGGGACATTCATTGCGGAATAACATCGGAGGAGAAGTTTCCCAGAGCT | | | | | | | | | | | | 128 |
| AGT | GGG | ACT | TCC | CAT | CCG | GCG | TTC | CTG | GTC | TTA | GGC | TGT | CTT | CTC | ACA | GGG | 179 |
| Met | Gly | Thr | Ser | His | Pro | Ala | Phe | Leu | Val | Leu | Gly | Cys | Leu | Leu | Thr | Gly | −7 |
| CTG | AGC | CTA | AGT | ATC | CTC | TGC | CAG | CTT | TCA | TTA | CCC | TCT | ATC | CTT | CCA | AAT | GAA | 230 |
| Leu | Ser | Leu | Ile | Leu | Cys | Gln | Leu | Ser | Leu | Pro | Ser | Ile | Leu | Pro | Asn | Glu | 11 |
| AAT | GAA | AAG | GTT | GTG | CAG | CTG | AAT | TCA | TCC | TTT | TCT | CTG | AGA | TGC | TTT | GGG | 281 |
| Asn | Glu | Lys | Val | Val | Gln | Leu | Asn | Ser | Ser | Phe | Ser | Leu | Arg | Cys | Phe | Gly | 28 |
| GAG | AGT | GAA | GTG | AGC | TGG | CAG | TAC | CCC | ATG | TCT | GAA | GAA | GAG | AGC | TCC | GAT | 332 |
| Glu | Ser | Glu | Val | Ser | Trp | Gln | Tyr | Pro | Met | Ser | Glu | Glu | Glu | Ser | Ser | Asp | 45 |
| GTG | GAA | ATC | AGA | AAT | GAA | GAA | AAC | AAC | AGC | GGC | CTT | TTT | GTG | ACG | GTC | TTG | 383 |
| Val | Glu | Ile | Arg | Asn | Glu | Glu | Asn | Asn | Ser | Gly | Leu | Phe | Val | Thr | Val | Leu | 62 |
| GAA | GTG | AGC | AGT | GCC | TCG | GCG | GCC | CAC | ACA | GGG | TTG | TAC | ACT | TGC | TAT | TAC | 434 |
| Glu | Val | Ser | Ser | Ala | Ser | Ala | Ala | His | Thr | Gly | Leu | Tyr | Thr | Cys | Tyr | Tyr | 79 |
| AAC | CAC | ACT | CAG | ACA | GAA | GAG | AAT | GAG | CTT | GAA | GGC | AGG | CAC | ATT | TAC | ATC | 485 |
| Asn | His | Thr | Gln | Thr | Glu | Glu | Asn | Glu | Leu | Glu | Gly | Arg | His | Ile | Tyr | Ile | 96 |
| TAT | GTG | CCA | GAC | CCA | GAT | GTA | GCC | TTT | GTA | CCT | CTA | GGA | ATG | ACG | GAT | TAT | 536 |
| Tyr | Val | Pro | Asp | Pro | Asp | Val | Ala | Phe | Val | Pro | Leu | Gly | Met | Thr | Asp | Tyr | 113 |
| TTA | GTC | ATC | GTG | GAG | GAT | GAT | GAT | TCT | GCC | ATT | ATA | CCT | TGT | CGC | ACA | ACT | 587 |
| Leu | Val | Ile | Val | Glu | Asp | Asp | Asp | Ser | Ala | Ile | Ile | Pro | Cys | Arg | Thr | Thr | 130 |
| GAT | CCC | GAG | ACT | CCT | GTA | ACC | TTA | CAC | AAC | AGT | GAG | GGG | GTG | GTA | CCT | GCC | 638 |
| Asp | Pro | Glu | Thr | Pro | Val | Thr | Leu | His | Asn | Ser | Glu | Gly | Val | Val | Pro | Ala | 147 |
| TCC | TAC | GAC | AGC | AGA | CAG | GGC | TTT | AAT | GGG | ACC | TTC | ACT | GTA | GGG | CCC | TAT | 689 |
| Ser | Tyr | Asp | Ser | Arg | Gln | Gly | Phe | Asn | Gly | Thr | Phe | Thr | Val | Gly | Pro | Tyr | 164 |
| ATC | TGT | GAG | GCC | ACC | GTC | AAA | GGA | AAG | AAG | TTC | CAG | ACC | ATC | CCA | TTT | AAT | 740 |
| Ile | Cys | Glu | Ala | Thr | Val | Lys | Gly | Lys | Lys | Phe | Gln | Thr | Ile | Pro | Phe | Asn | 181 |
| GTT | TAT | GCT | TTA | AAA | GCA | ACA | TCA | GAG | CTG | GAT | CTA | GAA | ATG | GAA | GCT | CTT | 791 |
| Val | Tyr | Ala | Leu | Lys | Ala | Thr | Ser | Glu | Leu | Asp | Leu | Glu | Met | Glu | Ala | Leu | 198 |
| AAA | ACC | GTG | TAT | AAG | TCA | GGG | GAA | ACG | ATT | GTG | GTC | ACC | TGT | GCT | GTT | TTT | 842 |
| Lys | Thr | Val | Tyr | Lys | Ser | Gly | Glu | Thr | Ile | Val | Val | Thr | Cys | Ala | Val | Phe | 215 |
| AAC | AAT | GAG | GTG | GTT | GAC | CTT | CAA | TGG | ACT | TAC | CCT | GGA | GAA | GTG | AAA | GGC | 893 |
| Asn | Asn | Glu | Val | Val | Asp | Leu | Gln | Trp | Thr | Tyr | Pro | Gly | Glu | Val | Lys | Gly | 232 |
| AAA | GGC | ATC | ACA | ATG | CTG | GAA | GAA | ATC | AAA | GTC | CCA | TCC | ATC | AAA | TTG | GTG | 944 |
| Lys | Gly | Ile | Thr | Met | Leu | Glu | Glu | Ile | Lys | Val | Pro | Ser | Ile | Lys | Leu | Val | 249 |
| TAC | ACT | TTG | ACG | GTC | CCC | GAG | GCC | ACG | GTG | AAA | GAC | AGT | GGA | GAT | TAC | GAA | 995 |
| Tyr | Thr | Leu | Thr | Val | Pro | Glu | Ala | Thr | Val | Lys | Asp | Ser | Gly | Asp | Tyr | Glu | 266 |
| TGT | GCT | GCC | CGC | CAG | GCT | ACC | AGG | GAG | GTC | AAA | GAA | ATG | AAG | AAA | GTC | ACT | 1046 |
| Cys | Ala | Ala | Arg | Gln | Ala | Thr | Arg | Glu | Val | Lys | Glu | Met | Lys | Lys | Val | Thr | 283 |
| ATT | TCT | GTC | CAT | GAG | AAA | GGT | TTC | ATT | GAA | ATC | AAA | CCC | ACC | TTC | AGC | CAG | 1097 |
| Ile | Ser | Val | His | Glu | Lys | Gly | Phe | Ile | Glu | Ile | Lys | Pro | Thr | Phe | Ser | Gln | 300 |
| TTG | GAA | GCT | GTC | AAC | CTG | CAT | GAA | GTC | AAA | CAT | TTT | GTT | GTA | GAG | GTG | CGG | 1148 |
| Leu | Glu | Ala | Val | Asn | Leu | His | Glu | Val | Lys | His | Phe | Val | Val | Glu | Val | Arg | 317 |
| GCC | TAC | CCA | CCT | CCC | AGG | ATA | TCC | TGG | CTG | AAA | AAC | AAT | CTG | ACT | CTG | ATT | 1199 |
| Ala | Tyr | Pro | Pro | Pro | Arg | Ile | Ser | Trp | Leu | Lys | Asn | Asn | Leu | Thr | Leu | Ile | 334 |
| GAA | AAT | CTC | ACT | GAG | ATC | ACC | ACT | GAT | GTG | GAA | AAG | ATT | CAG | GAA | ATA | AGG | 1250 |
| Glu | Asn | Leu | Thr | Glu | Ile | Thr | Thr | Asp | Val | Glu | Lys | Ile | Gln | Glu | Ile | Arg | 351 |
| TAT | CGA | AGC | AAA | TTA | AAG | CTG | ATC | CGT | GCT | AAG | GAA | GAA | GAC | AGT | GGC | CAT | 1301 |
| Tyr | Arg | Ser | Lys | Leu | Lys | Leu | Ile | Arg | Ala | Lys | Glu | Glu | Asp | Ser | Gly | His | 368 |
| TAT | ACT | ATT | GTA | GCT | CAA | AAT | GAA | GAT | GCT | GTG | AAG | AGC | TAT | ACT | TTT | GAA | 1352 |
| Tyr | Thr | Ile | Val | Ala | Gln | Asn | Glu | Asp | Ala | Val | Lys | Ser | Tyr | Thr | Phe | Glu | 385 |
| CTG | TTA | ACT | CAA | GTT | CCT | TCA | TCC | ATT | CTG | GAC | TTG | GTC | GAT | GAT | CAC | CAT | 1403 |
| Leu | Leu | Thr | Gln | Val | Pro | Ser | Ser | Ile | Leu | Asp | Leu | Val | Asp | Asp | His | His | 402 |
| GGC | TCA | ACT | GGG | GGA | CAG | ACG | GTG | AGG | TGC | ACA | GCT | GAA | GGC | ACG | CCG | CTT | 1454 |
| Gly | Ser | Thr | Gly | Gly | Gln | Thr | Val | Arg | Cys | Thr | Ala | Glu | Gly | Thr | Pro | Leu | 419 |
| CCT | GAT | ATT | GAG | TGG | ATG | ATA | TGC | AAA | GAT | ATT | AAG | AAA | TGT | AAT | AAT | GAA | 1505 |
| Pro | Asp | Ile | Glu | Trp | Met | Ile | Cys | Lys | Asp | Ile | Lys | Lys | Cys | Asn | Asn | Glu | 436 |
| ACT | TCC | TGG | ACT | ATT | TTG | GCC | AAC | AAT | GTC | TCA | AAC | ATC | ATC | ACG | GAG | ATC | 1556 |
| Thr | Ser | Trp | Thr | Ile | Leu | Ala | Asn | Asn | Val | Ser | Asn | Ile | Ile | Thr | Glu | Ile | 453 |
| CAC | TCC | CGA | GAC | AGG | AGT | ACC | GTG | GAG | GGC | CGT | GTG | ACT | TTC | GCC | AAA | GTG | 1607 |
| His | Ser | Arg | Asp | Arg | Ser | Thr | Val | Glu | Gly | Arg | Val | Thr | Phe | Ala | Lys | Val | 470 |
| GAG | GAG | ACC | ATC | GCC | GTG | CGA | TGC | CTG | GCT | AAG | AAT | CTC | CTT | GGA | GCT | GAG | 1658 |
| Glu | Glu | Thr | Ile | Ala | Val | Arg | Cys | Leu | Ala | Lys | Asn | Leu | Leu | Gly | Ala | Glu | 487 |
| AAC | CGA | GAG | CTG | AAG | CTG | GTG | GCT | CCC | ACC | CTG | CGT | TCT | GAA | CTC | ACG | GTG | 1709 |
| Asn | Arg | Glu | Leu | Lys | Leu | Val | Ala | Pro | Thr | Leu | Arg | Ser | Glu | Leu | Thr | Val | 504 |
| GCT | GCT | GCA | GTC | CTG | GTG | CTG | TTG | GTG | ATT | GTG | ATC | ATC | TCA | CTT | ATT | GTC | 1760 |
| Ala | Ala | Ala | Val | Leu | Val | Leu | Leu | Val | Ile | Val | Ile | Ile | Ser | Leu | Ile | Val | 521 |
| CTG | GTT | GTC | ATT | TGG | AAA | CAG | AAA | CCG | AGG | TAT | GAA | ATT | CGC | TGG | AGG | GTC | 1811 |
| Leu | Val | Val | Ile | Trp | Lys | Gln | Lys | Pro | Arg | Tyr | Glu | Ile | Arg | Trp | Arg | Val | 538 |
| ATT | GAA | TCA | ATC | AGC | CCA | GAT | GGA | CAT | GAA | TAT | ATT | TAT | GTG | GAC | CCG | ATG | 1862 |
| Ile | Glu | Ser | Ile | Ser | Pro | Asp | Gly | His | Glu | Tyr | Ile | Tyr | Val | Asp | Pro | Met | 555 |
| CAG | CTG | CCT | TAT | GAC | TCA | AGA | TGG | GAG | TTT | CCA | AGA | GAT | GGA | CTA | GTG | CTT | 1913 |
| Gln | Leu | Pro | Tyr | Asp | Ser | Arg | Trp | Glu | Phe | Pro | Arg | Asp | Gly | Leu | Val | Leu | 572 |
| GGT | CGG | GTC | TTG | GGG | TCT | GGA | GCG | TTT | GGG | AAG | GTG | GTT | GAA | GGA | ACA | GCC | 1964 |
| Gly | Arg | Val | Leu | Gly | Ser | Gly | Ala | Phe | Gly | Lys | Val | Val | Glu | Gly | Thr | Ala | 589 |
| TAT | GGA | TTA | AGC | CGG | TCC | CAA | CCT | GTC | ATG | AAA | GTT | GCA | GTG | AAG | ATG | CTA | 2015 |
| Tyr | Gly | Leu | Ser | Arg | Ser | Gln | Pro | Val | Met | Lys | Val | Ala | Val | Lys | Met | Leu | 606 |

TABLE 2-continued

Sequence of a human type A
PDGF receptor polypeptide allele and protein

| AAA | CCC | ACG | GCC | AGA | TCC | AGT | GAA | AAA | CAA | GCT | CTC | ATG | TCT | GAA | CTG | AAG | 2066 |
|---|---|---|---|---|---|---|---|---|---|---|---|---|---|---|---|---|---|
| Lys | Pro | Thr | Ala | Arg | Ser | Ser | Glu | Lys | Gln | Ala | Leu | Met | Ser | Glu | Leu | Lys | 623 |
| ATA | ATG | ACT | CAC | CTG | GGG | CCA | CAT | TTG | AAC | ATT | GTA | AAC | TTG | CTG | GGA | GCC | 2117 |
| Ile | Met | Thr | His | Leu | Gly | Pro | His | Leu | Asn | Ile | Val | Asn | Leu | Leu | Gly | Ala | 640 |
| TGC | ACC | AAG | TCA | GGC | CCC | ATT | TAC | ATC | ACA | GAG | TAT | TGC | TTC | TAT | GGA | | 2168 |
| Cys | Thr | Lys | Ser | Gly | Pro | Ile | Tyr | Ile | Ile | Thr | Glu | Tyr | Cys | Phe | Tyr | Gly | 657 |
| GAT | TTG | GTC | AAC | TAT | TTG | CAT | AAG | AAT | AGG | GAT | AGC | TTC | CTG | AGC | CAC | CAC | 2219 |
| Asp | Leu | Val | Asn | Tyr | Leu | His | Lys | Asn | Arg | Asp | Ser | Phe | Leu | Ser | His | His | 674 |
| CCA | GAG | AAG | CCA | AAG | AAA | GAG | CTG | GAT | ATC | TTT | GGA | TTG | AAC | CCT | GCT | GAT | 2270 |
| Pro | Glu | Lys | Pro | Lys | Lys | Glu | Leu | Asp | Ile | Phe | Gly | Leu | Asn | Pro | Ala | Asp | 691 |
| GAA | AGC | ACA | CGG | AGC | TAT | GTT | ATT | TTA | TCT | TTT | GAA | AAC | AAT | GGT | GAC | TAC | 2321 |
| Glu | Ser | Thr | Arg | Ser | Tyr | Val | Ile | Leu | Ser | Phe | Glu | Asn | Asn | Gly | Asp | Tyr | 708 |
| ATG | GAC | ATG | AAG | CAG | GCT | GAT | ACT | ACA | CAG | TAT | GTC | CCC | ATG | CTA | GAA | AGG | 2372 |
| Met | Asp | Met | Lys | Gln | Ala | Asp | Thr | Thr | Gln | Tyr | Val | Pro | Met | Leu | Glu | Arg | 725 |
| AAA | GAG | GTT | TCT | AAA | TAT | TCC | GAC | ATC | CAG | AGA | TCA | CTC | TAT | GAT | CGT | CCA | 2423 |
| Lys | Glu | Val | Ser | Lys | Tyr | Ser | Asp | Ile | Gln | Arg | Ser | Leu | Tyr | Asp | Arg | Pro | 742 |
| GCC | TCA | TAT | AAG | AAG | AAA | TCT | ATG | TTA | GAC | TCA | GAA | GTC | AAA | AAC | CTC | CTT | 2474 |
| Ala | Ser | Tyr | Lys | Lys | Lys | Ser | Met | Leu | Asp | Ser | Glu | Val | Lys | Asn | Leu | Leu | 759 |
| TCA | GAT | GAT | AAC | TCA | GAA | GGC | CTT | ACT | TTA | TTG | GAT | TTG | TTG | AGC | TTC | ACC | 2525 |
| Ser | Asp | Asp | Asn | Ser | Glu | Gly | Leu | Thr | Leu | Leu | Asp | Leu | Leu | Ser | Phe | Thr | 776 |
| TAT | CAA | GTT | GCC | CGA | GGA | ATG | GAG | TTT | CTG | GCT | TCA | AAA | AAT | TGT | GTC | CAC | 2576 |
| Tyr | Gln | Val | Ala | Arg | Gly | Met | Glu | Phe | Leu | Ala | Ser | Lys | Asn | Cys | Val | His | 793 |
| CGT | GAT | CTG | GCT | GCT | CGC | AAC | GTT | CTC | CTG | GCA | CAA | GGA | AAA | ATT | GTG | AAG | 2627 |
| Arg | Asp | Leu | Ala | Ala | Arg | Asn | Val | Leu | Leu | Ala | Gln | Gly | Lys | Ile | Val | Lys | 810 |
| ATC | TGT | GAC | TTT | GGC | CTG | GCC | AGA | GAC | ATC | ATG | CAT | GAT | TCG | AAC | TAT | GTG | 2628 |
| Ile | Cys | Asp | Phe | Gly | Leu | Ala | Arg | Asp | Ile | Met | His | Asp | Ser | Asn | Tyr | Val | 827 |
| TCG | AAA | GGC | AGT | ACC | TTT | CTG | CCC | GTG | AAG | TGG | ATG | GCT | CCT | GAG | AGC | ATC | 2729 |
| Ser | Lys | Gly | Ser | Thr | Phe | Leu | Pro | Val | Lys | Trp | Met | Ala | Pro | Glu | Ser | Ile | 844 |
| TTT | GAC | AAC | CTC | TAC | ACC | ACA | CTG | AGT | GAT | GTC | TGG | TCT | TAT | GGC | ATT | CTG | 2780 |
| Phe | Asp | Asn | Leu | Tyr | Thr | Thr | Leu | Ser | Asp | Val | Trp | Ser | Tyr | Gly | Ile | Leu | 861 |
| CTC | TGG | GAG | ATC | TTT | TCC | CTT | GGT | GGC | ACC | CCT | TAC | CCC | GGC | ATG | ATG | GTG | 2831 |
| Leu | Trp | Glu | Ile | Phe | Ser | Leu | Gly | Gly | Thr | Pro | Tyr | Pro | Gly | Met | Met | Val | 878 |
| GAT | TCT | ACT | TTC | TAC | AAT | AAG | ATC | AAG | AGT | GGG | TAC | CGG | ATG | GCC | AAG | CCT | 2882 |
| Asp | Ser | Thr | Phe | Tyr | Asn | Lys | Ile | Lys | Ser | Gly | Tyr | Arg | Met | Ala | Lys | Pro | 895 |
| GAC | CAC | GCT | ACC | AGT | GAA | GTC | TAC | GAG | ATC | ATG | GTG | AAA | TGC | TGG | AAC | AGT | 2933 |
| Asp | His | Ala | Thr | Ser | Glu | Val | Tyr | Glu | Ile | Met | Val | Lys | Cys | Trp | Asn | Ser | 912 |
| GAG | CCG | GAG | AAG | AGA | CCC | TCC | TTT | TAC | CAC | CTG | AGT | GAG | ATT | GTG | GAG | AAT | 2984 |
| Glu | Pro | Glu | Lys | Arg | Pro | Ser | Phe | Tyr | His | Leu | Ser | Glu | Ile | Val | Glu | Asn | 929 |
| CTG | CTG | CCT | GGA | CAA | TAT | AAA | AAG | AGT | TAT | GAA | AAA | ATT | CAC | CTG | GAC | TTC | 3035 |
| Leu | Leu | Pro | Gly | Gln | Tyr | Lys | Lys | Ser | Tyr | Glu | Lys | Ile | His | Leu | Asp | Phe | 946 |
| CTG | AAG | AGT | GAC | CAT | CCT | GCT | GTG | GCA | CGC | ATG | CGT | GTG | GAC | TCA | GAC | AAT | 3086 |
| Leu | Lys | Ser | Asp | His | Pro | Ala | Val | Ala | Arg | Met | Arg | Val | Asp | Ser | Asp | Asn | 963 |
| GCA | TAC | ATT | GGT | GTC | ACC | TAC | AAA | AAC | GAG | GAA | GAC | AAG | CTG | AAG | GAC | TGG | 3137 |
| Ala | Tyr | Ile | Gly | Val | Thr | Tyr | Lys | Asn | Glu | Glu | Asp | Lys | Leu | Lys | Asp | Trp | 980 |
| GAG | GGT | GGT | CTG | GAT | GAG | CAG | AGA | CTG | AGC | GCT | GAC | AGT | GGC | TAC | ATC | ATT | 3188 |
| Glu | Gly | Gly | Leu | Asp | Glu | Gln | Arg | Leu | Ser | Ala | Asp | Ser | Gly | Tyr | Ile | Ile | 997 |
| CCT | CTG | CCT | GAC | ATT | GAC | CCT | GTC | CCT | GAG | GAG | GAG | GAC | CTG | GGC | AAG | AGG | 3239 |
| Pro | Leu | Pro | Asp | Ile | Asp | Pro | Val | Pro | Glu | Glu | Glu | Asp | Leu | Gly | Lys | Arg | 1014 |
| AAC | AGA | CAC | AGC | TCG | CAG | ACC | TCT | GAA | GAG | AGT | GCC | ATT | GAG | ACG | GGT | TCC | 3290 |
| Asn | Arg | His | Ser | Ser | Gln | Thr | Ser | Glu | Glu | Ser | Ala | Ile | Glu | Thr | Gly | Ser | 1031 |
| AGC | AGT | TCC | ACC | TTC | ATC | AAG | AGA | GAG | GAC | GAG | ACC | ATT | GAA | GAC | ATC | GAC | 3341 |
| Ser | Ser | Ser | Thr | Phe | Ile | Lys | Arg | Glu | Asp | Glu | Thr | Ile | Glu | Asp | Ile | Asp | 1048 |
| ATG | ATG | GAC | GAC | ATC | GGC | ATA | GAC | TCT | TCA | GAC | CTG | GTG | GAA | GAC | AGC | TTC | 3392 |
| Met | Met | Asp | Asp | Ile | Gly | Ile | Asp | Ser | Ser | Asp | Leu | Val | Glu | Asp | Ser | Phe | 1065 |
| CTG | TAACTGGCGGATTCGAGGGGTTCCTTCCACTTCTGGGGCCACCTCTGGATCCCGTTCAGAAAA | | | | | | | | | | | | | | | | 3458 |
| Leu | 1066 | | | | | | | | | | | | | | | | |

| | | |
|---|---|---|
| CCACTTTATTGCAATGCGGAGGTTGAGAGGAGGACTTGGTTGATGTTTAAAGAGAAGTTCCCAGCCA | | 3525 |
| AGGGCCTCGGGGAGCCTTTCTAAATATGAATGAATGGGGATATTTTGAAAATGAACTTTGTCAGTGTTG | | 3592 |
| CCTCTTGCAATGCCTCAGTAGCATCTCAGTGGTGTGTGAAGTTTGGAGATAGATGGATAAGGGAATA | | 3659 |
| ATAGGCCACAGAAGGTGAACTTTCTGCTTCAAGGACATTGGTGAGAGTCCAACAGACACAATTTATA | | 3726 |
| CTGCGACAGAACTTCAGCATTGTAATTATGTAAATAACTCTAACCACGGCTGTGTTTAGATTGTATT | | 3793 |
| AACTATCTTCTTTGGACTTCTGAAGAGACCACTCAATCCATCCATTGCTACTTCCCTCTTGAAACCTGA | | 3860 |
| TGTCAGCTGCTGTTGAACTTTTTAAAGAAGTGCATGAAAAACCATTTTTTGACCTTAAAAGGTACTGG | | 3927 |
| TACTATAGCATTTTGCTATCTTTTTTAGTGTTAAAGAGATAAAGAATAATAATTAACCAACCTTGTT | | 3994 |
| TAATAGATTTGGGTCATTTAGAAGCCTGACAACTCATTTTCATATTGTAATCTATGTTTATAATACT | | 4061 |
| ACTACTGTTATCAGTAATGCTAAATGTGTAATAATGTAACATGATTTCCCTCCACACAAAGCACAAT | | 4128 |
| TTAAAAACAATCCTTACTAAGTAGGTGATGAGTTTGACAGTTTTTGACATTTATATTAAATAACATG | | 4195 |
| TTTCTCTATAAAGTATGGTAATAGCTTTAGTGAATTAAATTTAGTTGAGCATAGAGAACAAAGTAAA | | 4262 |
| AGTAGTGTTGTCCAGGAAGTCAGAATTTTTAACTGTACTGAATAGGTTCCCCAATCCATCGTATTAA | | 4329 |
| AAAACAATTAACTGCCCTCTGAAATAATGGGATTAGAAACAAAAATCTTAAGTCCTAAAAGTT | | 4396 |
| CTCAATGTAGAGGCATAAACCTGTGCTGAACATAACTTCTCATGTATATTACCCAATGGAAAATATA | | 4463 |
| ATGATCAGCGCANAAAGACTGGATTTGCAGAAGTTNTTTTTTTTTTCTTCTTGCCTGATGAAAGC | | 4530 |
| TTTGGCGACCCCAATATATGTATTTTTTGAATCTATGAACCTGAAAAGGGTCACAAAGGATGCCCAG | | 4597 |
| ACATCAGCCTCCTTCTTTCACCCCTTACCCCAAAGAGAAAGAGTTTGAAACTCGAGACCATAAAGAT | | 4664 |
| ATTCTTTAGTGGAGGCTGGAAGTGCATTAGCCTGATCCTCAGTTCTCAAATGTGTGTGGCAGCCAGG | | 4731 |
| TAGACTAGTACCTGGGTTTCCATCCTTGAGATTCTGAAGTATGAAGTCTGAGGGAAACCAGAGTCTG | | 4798 |

TABLE 2-continued

Sequence of a human type A
PDGF receptor polypeptide allele and protein

| | |
|---|---|
| TATTTTTCTAAACTCCCTGGCTGTTCTGATCGGCCAGGTTTCGGAAACACTGACTTAGGTTTCAGGA | 4865 |
| AGTTGCCATGGGAAACAAATAATTTGAACTTTGGAACAGGGTTCTTAAGTTGGTGCGTCCTTCGGAT | 4932 |
| GATAAATTTAGGAACCGAAGTCCAATCACTGTAAATTACGGTAGATCGATCGTTAACGCTGGAATTA | 4999 |
| AATTGAAAGGTCAGAATCGACTCCGACTCTTTCGATTTCAAACCAAAACTGTCCAAAAGGTTTTCAT | 5066 |
| TTCTACGATGAAGGGTGACATACCCCCTCTAACTTGAAAGGGGCAGAGGGCAGAAGAGCGGAGGGTG | 5133 |
| AGGTATGGGGCGGTTCCTTTCCGTACATGTTTTTAATACGTTAAGTCACAAGGTTCAGAGACACATT | 5200 |
| GGTCGAGTCACAAAACCACCTTTTTTTGTAAAATTCAAAATGACTATTAAAACTCCAATCTACCCTCCT | 5267 |
| ACTTAACAGTGTAGATAGGTGTGACAGTTTGTCCAACCACACCCAAGTAACCGTAAGAAACGTTATG | 5334 |
| ACGAATTAACGACTATGGTATACTTACTTTGTACCCGACACTAATGACGTTAGTGACACGATAGCCG | 5401 |
| TCTACTACGAAACCTTCTACGTCTTCGTTATTATTTCATGAACTGATGGATGACCACATTAGAGTTA | 5468 |
| CGTTCGGGGTTGAAAGAATAGGTTGAAAAAGTATCATTCACGCTTCTGACTCGGTCTAACCGGTTAA | 5535 |
| TTTTTCTTTTGGACTGATCCAAGACATCTCGGTTAATCTGAACTTTATGCAAACACAAAGATCTTAG | 5602 |
| TGTCGAGTTCGTAAGACAAATAGCGAGTGAGAGGGAACATGTCGGAATAAAACAACCACGAAACGTA | 5669 |
| AAACTATAACGACACTCGGAACGTACTGTAGTACTCCGGCCTACTTTGAAGAGTCAGGTCGTCAAAG | 5736 |
| GTCAGGATTGTTTACGAGGGTGGACTTAAACATATACTGACGTAAACACCCACACACACACAAAAGT | 5803 |
| CGTTTAAGGTCTAAACAAAGGAAAACCGGAGGACGTTTCAGAGGTCTTCTTTTAAACGGTTAGAAAG | 5870 |
| GATGAAAGATAAAAATACTACTGTTAGTTTCGCCGGACTCTTTGTGATAAACACTGAAAAATTTGC | 5937 |
| TAATCACTACAGGAATTTTACACCAGACGGTTAGACATGTTTTACCAGGATAAAAACACTTCTCCCT | 6004 |
| GTATTCTATTTTACTACAAATATGTAGTTATACATATATACATAAAGATATATCTGAACCTCTTATGA | 6071 |
| CGGTTTTGTAAATACTGTTCGACATAGTGACGGAAGCAAATATAAAAAAATTGACACTATTAGGGGT | 6138 |
| GTCCGTGTAATTGACAACGTGAAAACTTACAGGTTTTAAATATAAAATCTTTATTATTTTCTTTCT | 6205 |
| ATGAATGTACAAGGGTTTTGTTACCACACCACTTACACACACTCTTTTTGATTGAACTATCCCAGATGG | 6272 |
| TTATGTTTTACATAATGCTTACGGGGACAAGTACAAAAACAAAATTTTGCACATTTACTTCTAGAAA | 6339 |
| TATAAAGTTATTTACTATATATTAAATTTCCTTAAG | 6375 |
| Z | |

A polypeptide or nucleic acid is substantially pure, or substantially purified, when it comprises at least about 30% of the respective polymer in a composition, typically at least about 50%, more typically at least about 70%, usually at least about 80%, more usually at least about 90%, preferably at least about 95%, and more preferably about 98% or more.

The soluble fragments of the extracellular region will generally be less than about 400 amino acids, usually less than about 350 amino acids, more usually less than about 300 amino acids, typically less than about 200 amino acids, and preferably less than about 150 amino acids.

A. D Domains

Based on a number of observations, the extracellular region (XR) of these PDGF receptor polypeptides comprises 5 immunoglobulin-like domains. First, the amino acid sequence contains 5 segments characteristic of Ig-like domain structures, each of the segments having an appropriate size for an immunoglobulin domain. Each segment, except for the fourth, has characteristically spaced cysteine residues that are a diagnostic feature of an immunoglobulin-like domain. The receptor polypeptide sequence displays other features of immunoglobulin-like domain structure, e.g., the presence of characteristically positioned tryptophan and tyrosine residues. Direct sequence comparisons of segments of the receptor polypeptides with corresponding segments of true immunoglobulin domains shows a statistically significant similarity between PDGF receptor polypeptide domains and immunoglobulin domains. See, e.g., Williams (1989) Science 243: 1564–1570. The argument that the receptor polypeptide domains assume the folding pattern of immunoglobulin domains can be strengthened by examining the predicted secondary structure of the receptor polypeptides.

When a homology mapping analysis is performed, the PDGF receptor polypeptide shows five Ig-like domains in the extracellular region, each domain showing statistically significant homology to defined Ig-like domains. See, e.g., Williams and Barclay (1988) Ann. Rev. Immunol. Biochem. 6: 381– 405. Regions of homology will show significant sequence homology to particular Ig-like domains, and exhibit particular secondary and tertiary structural motifs characteristic of Ig-like domains. The domain structures will preferably be those segments with boundaries which approximately match the boundaries of the domain structures. The boundaries will preferably match within about 9 amino acids, typically within about 7 amino acids, more typically within about 5 amino acids, usually within about 3 amino acids, and more usually within 1 amino acid. See, e.g., Cantor and Schimmel (1980) Biophysical Chemistry, Vols I–III, Freeman and Co., San Francisco; Creighton (1984) Proteins: Structure and Molecular Properties, Freeman and Co., New York; and Watson et al. (1987) The Molecular Biology of the Gene, Vols 1 and 2, Benjamin, Menlo Park, Calif.; each of which is hereby incorporated herein by reference.

The sequences of the human type B and the human type A receptor polypeptides can be analyzed to predict their beta strand topology. Combining a Fourier analysis of hydrophobic sequence pattern and a Garnier-Robson algorithm, see, e.g., Garnier et al. (1978) J. Mol. Biol. 120: 97, with a turn predictor program, as reported in Cohen et al. (1986) Biochemistry 25: 266, produces a characteristic structural pattern. This pattern exhibits consensus β-strand segments in each domain when analysed as described.

The first two Ig-like domains of the PDGF receptor polypeptides, D1 and D2, have about seven β-strand segments, designated the A, B, C, D, E, F, and G segments, as listed from amino proximal to carboxy proximal direction. The third, fourth and fifth Ig-like domains, D3, D4 and D5, are long enough to include an extra β-strand segment, designated C'. The fifth domain, D5, most closely resembles a variable heavy chain domain in length. The type B receptor polypeptide D5 further comprises an additional β-strand segment designated C". These features and designations are based partly on the homology of segments between domains and segments in the type B and type A hPDGF-R polypeptides, and with the mouse type B PDGF receptor polypeptide, and also based upon homology to other Ig-like segments found on other proteins, particularly other growth factor receptor proteins. The csf-1 receptor and c-kit protooncogene have similar Ig-like domain organizations. See, e.g., Williams (1989) Science 243:1564–1570.

The domain structure is based, in part, upon features common to Ig-like domains found in other proteins, including related receptors. See, e.g., Ullrich and Schlessinger (1990) Cell 61:203–212; and Yarden and Ullrich (1988) Ann. Rev. Biochem. 57:443–78. The domain boundaries for the two alleles disclosed herein are identified below, but different alleles may have slightly different positions for the boundaries. See Table 14.

The Ig-like domains (D domains) are characterized by the regularity of spacing of cysteine residues in the extracellular region. These five D domains, each about 100 amino acids in length, have β-sheet rich structures, resembling immunoglobulin variable or constant regions. See, Williams (1989) Science 243:1964–1570. The natural XR domains are numbered from the amino proximal domain D1, in order, through D5, at the carboxy proximal end of the XR.

The exon structure of the mouse type B PDGF receptor polypeptide gene also matches this domain structure with reasonable fidelity. The correlation between the intron-exon structure and functional units further supports the hypothesis that the boundaries define functional units of the polypeptide. See, e.g., Williams and Barclay (1988) Ann. Rev. Immunol. Biochem. 6:381–405. The boundaries for each of these segments are indicated below for the two alleles disclosed herein, and similar boundaries will be found in other alleles at locations of sequence and functional homology.

The amino-proximal Ig-like domain of the human platelet-derived growth factor receptor polypeptides is designated D1. The D1 domain extends from about leu(1) to pro(91) in the type B receptor polypeptide, and from about gln(1) to pro(101) in the type A receptor polypeptide. See Table 14. The D1 domain apparently has about seven β-sheet segments.

The next Ig-like domain, in the carboxy proximal direction of natural human platelet-derived growth factor receptor polypeptides, is designated D2. The D2 domain extends from about thr(92) to ser(181) in the type B receptor polypeptide, and from about asp(102) to ser(189) in the type A receptor polypeptide. The D2 domain apparently also has about seven β-sheet strands designated A, B, C, D, E, F, and G.

The third Ig-like domain found on natural human PDGF receptor polypeptides is designated D3. The D3 domain extends from about ile(182) to gly(282) in the type B receptor polypeptide, and from about glu(190) to gly(290) in the type A receptor polypeptide. The D3 domain apparently has about eight β-sheet strands designated A, B, C, C', D, E, F, and G.

The fourth Ig-like domain found in the natural human PDGF receptor polypeptides is designated D4. The D4 domain extends from about tyr(283) to pro(384) in the type B receptor polypeptide, and from about phe(291) to pro(391) in the type A receptor polypeptide. The D4 domain apparently has about eight β-sheet strands. Note that the D4 domains lack the characteristic cysteine residues, which correspond to val(306) and met(364) in the type B sequence shown, and to val(313) and ile(371) in the type A sequence shown.

The fifth Ig-like domain is designated D5. The D5 domain extends from about val(385) to lys(499) in the type B receptor polypeptide, and from about ser(392) to glu(501) in the type A receptor polypeptide. The D5 of the type B receptor polypeptide has about nine putative β-sheet strand segments designated A, B, C, C', C", D, E, F, and G, while the type A receptor polypeptide has only about eight β-strand segments, lacking a C" segment.

The approximate boundaries of the domains and β-strand segments are listed in Table 14. The apparent alignments of the segments are illustrated in Tables 4 and 5. Other alleles of the receptor polypeptides may also be analyzed by either homology or the structural analysis as described above.

TABLE 14

|  | D1 | D2 | D3 | D4 | D5 |
|---|---|---|---|---|---|
| Human B-Type Receptor Polypeptide β-strand Segment Approximate Boundaries ||||||
| whole | leu (1) - pro (91) | thr (92) - ser (181) | ile (182) - gly (282) | tyr (283) - pro (384) | val (385) - lys (499) |
| A | val (2) - leu (10) | pro (97) - ile (105) | ser (185) - val (192) | leu (286) - gln (294) | val (385) - glu (392) |
| B | phe (18) - ser (25) | ile (110) - thr (120) | ile (199) - ile (206) | arg (300) - glu (309) | gln (400) - arg (407) |
| C | val (29) - met (33) | val (125) - lys (131) | asn (212) - pro (218) | thr (315) - asp (321) | asn (413) - cys (419) |
| C' | — | — | arg (224) - pro (228) | asp (327) - gly (331) | arg (424) - leu (429) |
| C" | — | — | — | — | glu (439) - glu (441) |
| D | glu (40) - asp (46) | ala (136) - pro (140) | asp (231) - pro (237) | ser (336) - glu (342) | val (448) - glu (454) |
| E | ser (51) - asn (57) | arg (145) - ser (148) | ser (242) - ser (248) | ser (347) - arg (353) | val (459) - leu (465) |
| F | gly (64) - asp (72) | arg (154) - ile (162) | gly (255) - glu (263) | gly (360) - his (368) | leu (472) - asn (480) |
| G | glu (80) - val (88) | asp (170) - gln (178) | glu (271) - val (278) | ser (376) - pro (384) | glu (488) - his (494) |
| Human A-Type Receptor Polypeptide β-strand Segment Approximate Boundaries ||||||
| whole | gln (1) - pro (101) | asp (102) - ser (189) | glu (190) - gly (290) | phe (291) - pro (391) | ser (392) - glu (501) |
| A | ser (6) - lys (14) | pro (107) - val (115) | glu (194) - val (201) | ile (294) - glu (302) | ser (392) - asp (399) |
| B | phe (22) - glu (29) | ala (123) - thr (130) | ile (208) - phe (215) | lys (310) - arg (317) | gln (408) - glu (415) |
| C | val (32) - met (38) | pro (135) - ser (141) | asp (221) - pro (227) | arg (323) - asn (329) | asp (421) - cys (427) |
| C' | — | — | lys (233) - met (237) | glu (335) - thr (338) | lys (432) - thr (437) |
| C" | — | — | — | — | — |
| D | asp (45) - ser (55) | val (144) - ser (148) | glu (240) - ser (245) | asp (343) - glu (349) | ile (453) - arg (456) |
| E | thr (60) - ser (66) | gln (153) - asn (156) | tyr (250) - glu (256) | ser (354) - arg (360) | val (461) - phe (467) |
| F | gly (73) - his (81) | gly (162) - val (170) | gly (263) - gln (271) | gly (367) - asn (375) | ile (474) - asn (482) |
| G | glu (90) - val (98) | ile (178) - lys (186) | met (279) - his (287) | thr (383) - pro (391) | glu (490) - pro (496) |

TABLE 4 a B-type receptor polypeptide amino acid sequence, with β-strand segment alignment

Domain 1

L VVIPPGPEL VLNVSST FVLT C SGS AP VVWERM SQEP ...

Domain 2

TVGFL PNDAEELFI FLTEITE ITIP C RVT DPQL VVTLHEK KGDV ...

Domain 3

INV SVNAVQT.V VR.QGEN ITLM C IVI GND...VV NFEWTYP RKESG RLVEP ...

Domain 4

YVR LLGEVGTLQ FAELHRS RTLQ V VFE AYPP...P TVLWFKD NRTLG DSSAG ...

Domain 5

.VRVLELSE SHPDSGE QTVR C RGR GMPQ...P NIIWSAC RD.LK RCPREL PPTLLGNSS EEE bbbbbbbb bbbb b bbb bbbbbbb bbbbbb bbb
A B C C' C"

Domain 1

PQ EMAKAQD GTFS SVLTLTN LTGLDT GEYF C THND SRGLETD ERKRLYIFV PDP

Domain 2

ALPVP YDHQ RGFS GIFED RSYI C KTTI GDREVDS DAYYVYRLQ VSS

Domain 3

VT DFLLDMP YHIR SILHIPS AELEDS GTYT C NVTE SVNDHQD EKAINITVV ESG

Domain 4

EIAL STRNVSE TRYV SELTLVR VKVAEA GHYT M RAFH EDAEVQL SFQLQINVP

Domain 5

SQLETN VTYWEEE QEFE VVSTLRL QHVDRP LSVR C TLRN AVGQDTQ EVIVVP HSLPFK bbbbbb bbbbbbb bbbb b bbbb bbbbbb
D E F G

TABLE 5 an A-type receptor polypeptide amino acid sequence, with β-strand segment alignment

Domain 1

QLSLPS IL.PNENEK VVQLNSS FSLR C FGE SE VSWQYPM SEEE ...

Domain 2

VAFV PLGMTDYLV IVEDDDS AIIP C RTT DPET PVTLHNS EG ...

Domain 3

ELDL EMEALKT.V YK.SGET IVVT C AVF NNE...VV DLQWTYP GEVKG KGITM ...

Domain 4

FIE IKPTFSQLE AVNLHEV KHF V VEV RAYPP...P RISWLKN NLTLI E...NLT ...

Domain 5

.SSILDLVD DHHGSTGG QTVR C TAE GTPL...P DIEWMIC KD.IK KCNNETS WTILANNV ...

bbbbbbbb bbbb b bbb bbbbbbb bbbbbb bbb
A B C C' C"

Domain 1

SS DVEIRNEENNS GLFV TVLEVSS ASAAHT GLYT C YYNH TQTEENEL EGRHTYTYV PDP

Domain 2

... VVPAS YDSR QGFN GTFTV GPYI C EATV KGKKFQT IPFNVYALK ATS

Domain 3

LE EIRVPS IKLV YTLTVPE ATVKDS GDYE C AARQ ATREVKE MKKVTISVH EKG

Domain 4

EITT DVE KIQE IRYR SKLKLIR AKEEDS GHYT I VAQN EDAVKSY TFELLTQVP

Domain 5

TABLE 5-continued an A-type receptor polypeptide amino acid sequence, with β-strand segment alignment

| SNITTE | I . . . HSR | DRST | VEGRVTF | AKVEET | IAVR | C | LAKN | LLGAENR | ELKLVA . . . P | TLRSE |
|--------|-------------|------|---------|--------|------|---|------|---------|----------------|-------|
|        | bbbbbbbbbbb |      | bbbbbbb |        | bbbb | b | bbbb |         | bbbbbbbbb      |       |
|        | D           |      | E       |        |      | F |      |         | G              |       |

The prototypical D1 domains are those sequences of the human type B receptor polypeptide and the human type A receptor polypeptide, as described. However, compatible amino acid substitutions, insertions, and deletions which preserve the desired ligand binding functions can be made. The function will usually be preserved by retaining the LBR segments in the correct orientation by use of appropriate structured segments. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Substitution or exchange of β-sheet segments or sequences intermediate the segments from different domains may be performed, including between type B and A receptor polypeptides, or between different domains of another related receptor polypeptide. Segments outside the prototypical cysteines within β-segments B and F (but val(306) and met(364) in the type B D4, and val(313) and ile(371) in the type A D4) will be usually less critical than the sequences between those residues, e.g., the C, C', C", D; and E β-strand segments. Also, segments homologous to these disclosed segments may be substituted, including those with compatible amino acid substitutions, insertions, and deletions. Sources of similar domains and segments include related receptor polypeptides from human or other mammalian species. Non-mammalian receptor polypeptides may also exhibit significant homology and serve as sources for similar segments. Other Ig-like domains and segments may also be substituted.

The present invention embraces polypeptides which exhibit homology to the disclosed and described segments and domains. It embraces segments comprising contiguous amino acids of the sequences disclosed, typically at least about 8 contiguous amino acids, more typically at least about 11 contiguous amino acids, usually at least about 14 contiguous amino acids, more usually at least about 17 contiguous amino acids, and preferably at least about 21 or more contiguous amino acids. Constructs retaining the LBR segments are most valuable. The invention also includes modifications of those sequences, including insertions, deletions, and substitutions with other amino acids. Glycosylation modifications, either changed, increased amounts, or decreased amounts, as well as other sequence modifications are envisioned. Thus, the modified proteins comprising these amino acid sequences, e.g., analogues, will usually be substantially equivalent to these proteins in either function or structure.

The β-sheet strands may be slightly enlarged or shortened by respective insertions or deletions in the polypeptide sequence. Thus, certain embodiments will have a slightly enlarged or shortened particular domain by adding or deleting particular sequences of β-sheet strands or their interstrand sequences. Segments may be inserted or deleted which conform to the structural requirements of retaining the proper intra- and inter-domain interactions. In particular, changes which interrupt the secondary and tertiary structure of the protein will be disfavored. See, e.g., Cantor and Schimmel (1990) and Creighton (1984). In addition, amino acids or segments may be inserted or deleted in the regions outside of the β-sheet strands and between domains. Typically the substitutions will be of amino acids having similar properties, and additions or deletions would preferably be selected among those which retain receptor biological functions, e.g., ligand binding.

The sequence of a β-sheet segment will typically not differ from a sequence from a human type B polypeptide or a human type A polypeptide by greater than about 50%, more typically less than about 39%, usually less than about 29%, and more usually less than about 20%. Comparable similarities over each of the non-β-sheet strands of each domain will be preferred.

The boundaries between domains are defined, in part, by the definitions for domains in the Ig-like domains. Examples of similar domains are found in immunoglobulin and growth factor receptor polypeptides. The domain boundaries between D1 and D2; D2 and D3; D3 and D4; and D4 and D5 correspond approximately to exon locations, further supporting the proposal that the domain structures correspond to evolutionary and functional units. See, e.g., Watson et al. (1987) *The Molecular Biology of the Gene*, vols. 1 and 2, Benjamin, Menlo Park, Calif.

The D2 domains have similar characteristics to the D1 domains, as shown by the alignments illustrated in Tables 4 and 5. Both domains have β-sheet segments designated A, B, C, D, E, F, and G. The domain 3 segments, or D3, also exhibit homology, but have an additional β-strand segment designated C'. The D4 segments, or D4, have non-cysteine residues at the positions which typically correspond to cysteines in the other domains. In the type B allele shown, the residues are val(306) and met(364), while in the type A allele shown, the residues are val(313) and ile(371). The D4 domains also have β-strand segments designated C'. The domain 5, or D5, have the consensus cysteine residues and the additional C' β-strand segments, and the type B receptor polypeptide has an additional C" β-strand segment.

The present invention provides for various constructs comprising ligand binding constructs, typically comprising substantially intact domains. These constructs will have various uses, e.g., for binding ligands, or substituting for intact receptor polypeptides. For example, each of the separate domains may comprise a separate polypeptide alone, or may be fused to another peptide, such as the TM and IR regions of a receptor polypeptide, e.g., hPDGF-R. See, e.g., Table 6. These individual single domain polypeptides will exhibit specific activity associated with these specific domains, preferably as an agonist or antagonist for ligand binding, preferably with characteristics shared with the intact receptor polypeptide or XR. The domains may also preferably serve as competitive inhibitors of PDGF-R polypeptides, competing with natural PDGF-receptors to bind ligands. The present invention also provides repetitive sequences of a single domain. For example, a D1 domain by itself is provided, a D1-D1 dimer in a single polypeptide is provided, a D1-D1-D1 triplet repeat is also provided. Likewise up to a large number of D1 domains which will exhibit many functions, e.g., immunological properties, characteristic of various natural PDGF-R sequences. Similar constructs of each of D2, D3, D4, and D5 are provided, along with combinations. See Tables 6, 7, 8, 9 and 10. These will often be soluble fragments of the XR, or may be fused to other polypeptides, including a PDGF-R TM segment, preferably with an IR segment also.

TABLE 6

| XR domain structure of single domain forms | | | | |
|---|---|---|---|---|
| D1 | D2 | D3 | D4 | D5 |

TABLE 7

| XR domain structure of two domain forms | | | | |
|---|---|---|---|---|
| D1–D1 | D2–D1 | D3–D1 | D4–D1 | D5–D1 |
| D1–D2 | D2–D2 | D3–D2 | D4–D2 | D5–D2 |
| D1–D3 | D2–D3 | D3–D3 | D4–D3 | D5–D3 |
| D1–D4 | D2–D4 | D3–D4 | D4–D4 | D5–D4 |
| D1–D5 | D2–D5 | D3–D5 | D4–D5 | D5–D5 |

TABLE 8

| XR domain structure of three domain forms | | | | |
|---|---|---|---|---|
| D1-W | D2-W | D3-W | D4-W | D5-W | where W is each of the 25 possible combinations listed in TABLE 2, giving a total of 125 elements in this table

TABLE 9

| XR domain structure of four domain forms | | | | |
|---|---|---|---|---|
| D1-X | D2-X | D3-X | D4-X | D5-X | where X is each of the 125 possible combinations listed in TABLE 5, giving a total of 625 elements in this table

TABLE 10

| XR domain structure of five domain forms | | | | |
|---|---|---|---|---|
| D1-Y | D2-Y | D3-Y | D4-Y | D5-Y | where Y is each of the 625 possible combinations listed in TABLE 6, but not including the combination D1-D2-D3-D4-D5, giving a total of 3124 elements in this table In addition, the present invention provides similar structures with spacer regions between the domain structures. In particular, the regions corresponding to the intra-cysteine residues of the domains shown in Tables 4 and 5 are useful. For example, a spacer polypeptide may be inserted between adjacent domains or do spaces between the important ligand binding segments, typically found within the intra-cysteine segments described, e.g., the B, C, C', C", D, E, and F β-strand segments. Thus, for example, a polypeptide of the structure D1-X1-D2 is provided where X1 is a spacer segment which is not a D domain. The order of the domains may be reversed, and the invention also provides polypeptides such as D2-D1, or D2-X1-D1. In particular, the non-D domain character of X1 is provided to avoid the peptide D1-X1-D3 from describing, or encompassing, D1-D2-D3.

Another particularly preferred embodiment of the invention is a polypeptide having the described extracellular region domain structure combined with other segments of a human platelet-derived growth factor receptor, particularly the transmembrane segment (TM) and the intracellular region (IR). Thus, the present invention provides for a receptor polypeptide which either has a modified order of the extracellular region domains in the amino to carboxy direction, e.g., a D5-D4-D3-D2-D1-TM-IR polypeptide, or, in some cases reversal of various domains. It also provides for a receptor polypeptide with a deleted intact domain and for a receptor polypeptide having an additional domain added to it. Examples include D1-D2-D3-TM-IR, or D1-D2-D3-D4-TM-IR. In particular, fusions with the XR segments described in Tables 6, 7, 8, 9, and 10 are preferred embodiments.

The modified combinations of the D domains are expected to both simulate and differ from the natural receptor.

The modified polypeptide would be expected, in some embodiments, to exhibit a modified binding affinity, e.g., higher or lower affinity, or to exhibit a different spectrum of binding to different ligands or ligand analogues. They may also have an altered ligand binding transducing efficiency, or a modified inter-chain association affinity.

The present invention provides the means for determining the minimal structural features necessary to perform various functions of the extracellular region of platelet-derived growth factor receptors, preferably human receptors. Although similar determinations may be performed in mouse or other mammalian species, the human receptor will typically be preferred for diagnostic or therapeutic purposes.

To determine the minimal region necessary for a functional activity, e.g., ligand binding, an assay for that activity is developed. The main receptor functions, as indicated above, include ligand binding, tyrosine kinase activity, and receptor dimerization. Simple and quick assays for each of these molecular functions may be developed. Ligand binding assays are described, e.g., in Gronwald et al. (1988) Proc. Nat'l Acad. Sci. USA 85:3435–3439; Heldin et al. (1988) EMBO J. 7:1387–1393; and Escobedo et al. (1988) Science 240:1532–1534. Receptor dimerization assays are described, e.g., in Yarden and Schlessinger (1987) Biochemistry 26:1434–1442 and 1443–1451.

As an alternative means for determining sites which interact with specific other proteins, physical structure determination, e.g., x-ray crystallography or 2 dimensional NMR techniques, will provide guidance as to which amino acid residues form the molecular contact regions. For a detailed description of protein structural determination, see, e.g., Blundell and Johnson (1976) Protein Crystallography, Academic Press, New York, which is hereby incorporated herein by reference.

Ligand binding assays may include binding of labeled ligand or competition assays for binding. Signal transduction may be indirectly assayed by measuring an activity modulated by ligand binding, e.g., tyrosine kinase activity, or some measure of a conformational or other change in receptor structure. For example, an antibody or other binding protein which specifically binds or dissociates from the receptor polypeptide upon ligand binding may be used. Receptor dimerization may be measured by a proximity assay, including a fluorescence quenching or other spectroscopic measurement. Various proximity assays are known, see, e.g., Ullrich and Schlessinger (1990) Cell 61:203–212; Yarden and Schlessinger (1987) Biochemistry 26:1434–1942 and 1443–1451; each of which is hereby incorporated herein by reference.

Once an assay has been developed, various combinations of domain or other segments, e.g., LBR's, can be tested for affecting that activity. A competitive inhibition assay will detect those constructs which can bind the ligand. The first domain structures to try will ordinarily be the individual domains, either alone or linked to chimeric proteins or the TM-IR segment of the receptor. Various alleles, modifications to the individual domains, or related chimeric domains would be tested. Both deletion and chimeric proteins will be constructed.

Various combinations of each domain will be constructed and tested to select those which affect the measured activity. Repeats of those domains should be tested, e.g., D1-D1. If no single domain does affect the function, then various 2 domain constructs, in order, would be tried, e.g., D1-D2-TM-IR, D2-D3-TM-IR, D3-D4-TM-IR, and D4-D5-TM-IR. Selected combinations listed in Tables 6, 7, 8, 9, and 10 will be constructed and tested.

In order to produce soluble forms, it will often be desireable to attach appropriate amino terminal segments, some of which would be expected to be present in the D1 domain or in the precursor form. Correct secretion and processing may be dependent upon various amino proximal features, such as signal sequences, and other features essential for correct targeting and processing. See, e.g., Watson et al. (1987) *The Molecular Biology of the Gene*, vols. 1 and 2, Benjamin, Menlo Park, Calif.

When correct domains have been selected which are especially effective in modulating or competing defined functions, a more detailed analysis, to the level of the β-strand segments might be addressed. Various chimeric, deletion, insertion, or substitution constructs of each β-strand or inter-strand segment may be generated and tested, as described above. Each construct could be produced using methods of standard genetic engineering, especially using synthetic primers. Procedures for using such reagents are described, e.g., in Sambrook, et al. (1989) *Molecular Cloning: A Laboratory Manual*, vols. 1–3, Cold Spring Harbor Press, and Ausubel et al. (eds.) (1989) *Current Protocols in Molecular Biology*, Wiley, each of which is hereby incorporated herein by reference.

B. Soluble Forms

In some embodiments, only the extracellular region is provided. Thus, the extracellular region alone, without the transmembrane segment, will often be a soluble polypeptide. It has been demonstrated that the entire extracellular region, separated from, and which lacks a transmembrane region and an intracellular region, still serves as a ligand binding polypeptide. In particular, the soluble polypeptide D1-D2-D3-D4-D5 has been demonstrated to bind various PDGF forms. Although the binding specificity for the PDGF form is dependent, to some extent, on the specific domains included, modifications to the specificity of the ligand binding may be effected by either substituting various different domains or rearranging the domains. Substitution with other homologous segments may also be performed, e.g., substituting an Ig-like domain from an antibody molecule, such as an antibody which binds a platelet-derived growth factor. Alternatively, a domain from a different related growth factor or ligand receptor may be substituted, e.g., from an FGF receptor or another PDGF receptor. The order of the domains may also be modified, e.g., D5-D4-D3-D2-D1.

In particular, the activities which will usually be of greatest importance with the extracellular constructs relate to the binding of the ligand. For example, it has been discovered that domains D4 and D5 are not essential for ligand binding of a soluble extracellular region PDGF-R polypeptide. Of the remaining domains, if domain D3 is separated from domains D1 and D2, the construct D1-D2 binds the ligand only at low affinity, but a D1-D2-D3 construct binds ligand at high affinity.

A typical hPDGF-R nucleic acid sequence encodes a transitory amino terminal hydrophobic sequence, which is usually cleaved during the membrane translocation process. The classical function of a signal sequence is to direct the nascent polypeptide chain to membrane bound ribosomes, thereby leading to membrane translocation or cellular targeting. However, since the signal sequence is typically removed in the translocation process, the signal sequence is usually absent in a mature polypeptide. Often a signal sequence will be attached upstream of a desired soluble peptide of this invention.

Solubility of a polypeptide depends upon the environment and the polypeptide. Many parameters affect polypeptide solubility, including the temperature, the electrolyte environment, the size and molecular characteristics of the polypeptide, and the nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified to conform to standard buffers used in physiological or analytical contexts.

The size and structure of the polypeptide should be in a substantially stable and globular state, and usually not in a denatured state. The polypeptide may be associated with other polypeptides in a quaternary structure, e.g., to confer solubility.

The solvent will usually be a biologically compatible buffer, of a type used for preservation of biological activities, and will usually approximate a physiological solvent. On some occasions, a detergent will be added, typically a mild non-denaturing one.

Solubility is usually measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman, and Cantor and Schimmel (1980) *Biophysical Chemistry*, parts 1–3, W. H. Freeman & Co., San Francisco, each of which is hereby incorporated herein by reference. As a crude determination, a sample containing a "soluble" polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

This invention provides platelet-derived growth factor polypeptides and proteins having platelet-derived growth factor receptor ligand binding activity. The receptors of the present invention include PDGF receptor amino acid sequences such as those shown in Tables 6, 7, 8, 9, and 10. Also provided are homologous sequences, allelic variations, induced mutants, alternatively expressed variants, and proteins encoded by DNA which hybridize under high stringency conditions to PDGF receptor encoding nucleic acids retrieved from naturally occurring material.

The platelet-derived growth factor receptor peptides of the present invention will exhibit at least about 80% homology with naturally occurring domains of hPDGF receptor sequences in the domains D1, D2, D3, D4, and D5, typically at least about 85% homology with a natural form of a receptor sequence, more typically at least about 90% homology, usually at least about 95% homology, and more usually at least about 97% homology.

Homology, for polypeptides, is typically measured using sequence analysis software, see, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications. Similar, or homologous, substitutions for LBR segments will be made in known sequences, thereby producing new binding molecules having modified affinity or specificity of ligand binding.

Various other software analysis programs can analyze the conformational structure of a polypeptide. Homologous conformation may also be achieved by appropriate insertion, deletion, substitution, or modification of amino acid sequences. Since the conformational structure of the domains and β-strand segments is only partially understood, the present invention also encompasses various modifications to the sequences disclosed and retaining these structural features.

In particular, ligand binding function is believed to be localized to the extracellular domain, particularly the LBR's, and the soluble forms will preferably retain this particular function. Soluble fragments of PDGF receptors will be useful in substituting for or for interfering with, e.g., blocking, by competing for PDGF binding, the functions of the natural receptor both in vitro and in vivo. Alternatively, soluble forms may interfere with the dimerization of PDGF receptor polypeptides, since the proteins may normally be in, or function in, a dimer form. Receptor dimerization may be essential for proper physiological signal transduction, and introduction of fragments may function to interrupt these processes by blocking their dimerization.

PDGF receptor polypeptides may be purified using techniques of classical protein chemistry, see, e.g., Deutscher (ed.) (1990) *Guide to Purification*; Methods in Enzymology, Vol. 182, which is hereby incorporated herein by reference. Alternatively, a lectin affinity chromatography step may be used, or a highly specific ligand affinity chromatography procedure, e.g., one that utilizes a PDGF conjugated to biotin through cysteine residues of the protein mitogen. Purified PDGF receptor polypeptides may also be obtained by a method such as PDGF affinity chromatography using activated CH-Sepharose coupled to PDGF through primary amino groups as described in Imamura et al. (1988) *Biochem. Biophys. Res. Commun.* 155:583–590.

Depending on the availability of specific antibodies, specific PDGF receptor peptide constructs may also be purified using immuno-affinity chromatography. Antibodies prepared, as described below, may be immobilized to an inert substance to generate a highly specific immuno-affinity column. See, e.g., Harlow and Lane (1990) *Monoclonal Antibodies: A Laboratory Manual*, Cold Spring Harbor Laboratory, which is hereby incorporated herein by reference.

Various cells or tissues may be selected as starting materials, usually selected on the basis of abundant expression of the desired receptor construct or polypeptide. High expression promoter sequences may be operably linked to a recombinant sequence, preferably an inducible promoter. The promoter is operably linked when it operates to promote the sequence. Appropriate cells that contain relatively large amounts of the receptor protein, as determined by high affinity binding of PDGF, can be transformed with variants of the PDGF receptor polypeptides. These may be used to replace the natural form of PDGF receptor by a construct with a deletion or insertion.

The ligand binding regions (LBR's) or other segments may be "swapped" between different new fusion constructs or fragments. Thus, new chimeric polypeptides exhibiting new combinations of segments can result from the structural linkage of different functional domains. Ligand binding regions which confer desired or modified specificities may be combined with other domains which have another function, e.g., each Ig-like domain could be substituted by a similar domain from other related polypeptides, or LBR's between different alleles or similar receptors may be combined.

The present invention also provides for fusion polypeptides between the receptor polypeptide domains and other homologous or heterologous proteins. Homologous proteins may be fusions between similar but different growth factor receptors resulting in, e.g., a hybrid protein exhibiting ligand specificity of one receptor with an intracellular domain of another, or a receptor which may have altered affinity or a broadened or narrowed specificity of binding. Likewise, heterologous fusions may be constructed which exhibit a combination of properties or activities of the derivative proteins. Typical examples are fusions of a reporter polypeptide, e.g., luciferase, with a domain of a receptor, e.g., a ligand binding domain from the extracellular region of a human platelet-derived growth factor receptor, so that the presence or location of a desired ligand may be easily determined. See, e.g., Dull et al., U.S. Pat. No. 4,859,609, which is hereby incorporated herein by reference. Other gene fusion partners include bacterial β-galactosidase, trpE, protein A, β-lactamase, α-amylase, alcohol dehydrogenase, and yeast α-mating factor. See, e.g., Godowski et al., (1988) *Science* 241: 812–816. Additional sequences with various defined functions may be found by searching through the GenBank™ (National Institutes of Health) sequence data bank. A heterologous fusion protein is one which includes sequences not naturally found in conjunction with one another. Thus, a heterologous fusion protein may be a fusion of two similar, and homologous, sequences.

Fusion proteins would typically be made by either recombinant nucleic acid methods with expression, or by synthetic polypeptide methods. Techniques for nucleic acid manipulation are described generally, for example, in Sambrook et al. (1989) *Molecular Cloning: A Laboratory Manual* (2nd ed.) volumes 1–3, Cold Spring Harbor Laboratory, which is hereby incorporated herein by reference. Techniques for synthesis of polypeptides are described, for example in Merrifield (1963) *J. Amer. Chem. Soc.* 85:2149–2456; Atherton et al. (1989) *Solid Phase Peptide Synthesis: A Practical Approach*, IRL Press, Oxford; and Merrifield (1986) *Science* 232:341–347; each of which is hereby incorporated herein by reference.

The recombinant nucleic acid sequences used to produce fusion proteins of the present invention may be derived from natural or synthetic sequences. Many natural gene sequences are available from various cDNA or from genomic libraries using appropriate probes, see, e.g., GenBank™, National Institutes of Health.

Typical probes for isolating platelet-derived growth factor receptor genes may be selected from sequences of Tables 1 and 2, in accordance with standard procedures. Suitable synthetic DNA fragments may be prepared, e.g., by the phosphoramidite method described by Beaucage and Carruthers (1981) *Tetra. Letts.* 22:1859-1862. A double stranded fragment may then be obtained by either synthesizing the complementary strand and hybridizing the strands together under appropriate conditions or by adding the complementary strand using DNA polymerase with an appropriate primer sequence.

III. Nucleic Acids

The present invention provides nucleic acid sequences encoding various PDGF receptor sequences described above. Tables 1 and 2, respectively set forth the corresponding cDNA sequences encoding human type B and type A PDGF receptor polypeptides.

Substantial homology in the nucleic acid context means either that the segments, or their complementary strands, when compared, are the same when properly aligned, with appropriate nucleotide insertions or deletions, in at least about 60% of the residues, typically at least about 70%, more typically at least about 80%, usually at least about 90%, and more usually at least about 95 to 98% of the nucleotides. Appropriate nucleotide insertions or deletions include interdomain sequences, or those external to the cysteines within a domain, but the sequences within the paired cysteines (or their equivalents in the D4 domains) will often be very important to retain. Structural homology will exist when there is at least about 55% homology over a stretch of at least about 14 nucleotides, typically at least about 65%, more typically at least about 75%, usually at least about 90%, and more usually at least about 95% or more.

Alternatively, substantial homology exists when the segments will hybridize under selective hybridization conditions, to a strand, or its complement, typically using a sequence of at least about 20 contiguous nucleotides derived from Table 1 or 2. However, larger segments would usually be preferred, e.g., at least about 30 contiguous nucleotides, more usually at least about 40, and preferably more than about 50. Selectivity of hybridization exists when hybridization occurs which is more selective than total lack of specificity. See, Kanehisa (1984) *Nucleic Acids Res.* 12:203-213, which is incorporated herein by reference.

Stringent hybridization conditions will normally include salt concentrations of less than about 1M, typically less than about 700 mM, more typically less than about 500 mM, usually less than about 400 mM, more usually less than about 300 mM, and preferably less than about 200 mM. Temperature conditions will typically be greater than about 20° C., more typically greater than about 25° C., usually greater than about 30° C., more usually greater than about 37° C., and preferably in excess of about 40° C., depending upon the particular application. As other factors may significantly affect the stringency of hybridization, including, among others, base composition and size of the complementary strands, presence of organic solvents, and extent of base mismatching, the combination of parameters is more important than the absolute measure of any one.

Probes may be prepared based on the sequence of the PDGF receptor encoding sequences provided in Tables 1 and 2. The probes may be used to isolate other PDGF receptor nucleic acid sequences by standard methods. See, e.g., Sambrook et al. (1989) *Molecular Cloning: A Laboratory Manual*, vols. 1-3, CSH Press, New York, which is hereby incorporated herein by reference. Other similar nucleic acids may be selected for by using homologous nucleic acids. Alternatively, nucleic acids encoding these same or similar receptor polypeptides may be synthesized or selected by making use of the redundancy in the genetic code. Various codon substitutions may be introduced, e.g., silent changes thereby providing various convenient restriction sites, or to optimize expression for a particular system, e.g., to match the optimum codon usage. Mutations may be introduced to modify the properties of the receptors, perhaps to change the ligand binding affinities, the interchain affinities, or the polypeptide degradation or turnover rate.

The DNA compositions of this invention may be derived from genomic DNA or cDNA, prepared by synthesis or may be a hybrid of the various combinations. Recombinant nucleic acids comprising sequences otherwise not naturally occurring in continuity are also provided by this invention. An isolated DNA sequence includes any sequence that has been obtained by primer or hybridization reactions or subjected to treatment with restriction enzymes or the like.

Synthetic oligonucleotides can be formulated by the triester method according to Matteucci et al. (1981) *J. Am. Chem. Soc.* 103:3185 or by other methods such as commercial automated oligonucleotide synthesizers. Oligonucleotides can be labeled by excess polynucleotide kinase (e.g., about 10 units to 0.1 nanomole substrate is used in connection with 50 mM Tris, pH 7.6, 5 mM dithiothreitol, 10 mM $MgCl_2$, 1-2 mM ATP, 1.7 pmoles $^{32}$P-ATP (2.9 mCi/mmole) 0.1 mM spermidine, 0.1 mM EDTA). Probes may also be prepared by nick translation, Klenow fill-in reaction, or other methods known in the art. See, e.g., Sambrook et al.

cDNA or genomic libraries of various types may be screened for new alleles or related sequences. The choice of cDNA libraries normally corresponds to a tissue source which is abundant in mRNA for the desired receptors. Phage libraries are normally preferred, but plasmid libraries may also be used. Clones of a library are spread onto plates, transferred to a substrate for screening, denatured, and probed for the presence of desired sequences.

For example, with a plaque hybridization procedure, each plate containing bacteriophage plaques is replicated onto duplicate nitrocellulose filter papers (Millipore-HATF). The phage DNA is denatured with a buffer such as 500 mM NaOH, 1.5M NaCl for about 1 minute, and neutralized with, e.g., 0.5M Tris-HCl, pH 7.5, 1.5M NaCl (3 times for 10 minutes each). The filters are then washed. After drying, the filters are typically baked, e.g., for 2 hours at 80° C. in a vacuum oven. The duplicate filters are prehybridized at 42° C. for 4-24 hours with 10 ml per filter of DNA hybridization buffer (20-50% formamide, 5× SSC, pH 7.0, 5× Denhardt's solution (polyvinylpyrrolidone, plus Ficoll and bovine serum albumin; 1×=0.02% of each), 50 mM sodium phosphate buffer at pH 7.0, 0.2% SDS, and 50 µg/ml denatured salmon sperm DNA). Hybridization with an appropriate probe may be performed at 42° C. for 16 hrs with 10 ml/filter of 1×10$^6$ cpm/ml of DNA hybridization buffer containing radioactively labeled probe. The final concentration of formamide is varied according to the length of the probe and the degree of stringency desired. See, e.g., Wetmur and Davidson (1968) *J. Mol. Biol.* 31:349-370; and M. Kanehisa (1984) *Nuc. Acids Res.* 12:203-213, each of which is incorporated herein by reference, for a discussion of hybridization conditions and sequence homology.

An oligonucleotide probe based on the disclosed amino acid sequences may be used to site specifically mutate or generate recombinant fusion or deletion constructs. See, e.g., Tables 11 and 12 for preferred oligonucleotide reagents. Procedures such as those described by Kimbel et al. (1987) *Methods in Enzymology* 154:367, may be used. The sequences PΔ1 through PΔ9 correspond to Seq. ID No. 6 through 14, respectively, and sequences PΔ101 through PΔ109 correspond to seq. ID No. 15 through 23, respectively.

TABLE 11

HUMAN B-type PDGF-R MUTAGENESIS OLIGOMERS

```
              Domain 5                 /    3'NonCoding
PΔ1  5' CCA CAC TCC TTG CCC TTT AAG/ TAGCTTCCTGTAGGGGGCTG 3'
         P   H   S   L   P   F   K /   * *********

Domain 4                 /    3'NonCoding
PΔ2  5' TCC TTC GAC CTA CAG ATC AAT/ TAGCTTCCTGTAGGGGGCTG 3'
         S   F   Q   L   Q   I   N /   * *********

Domain 3                 /    3'NonCoding
PΔ3  5' ATC ACC GTG GTT GAG AGC GGC/ TAGCTTCCTGTAGGGGGCTG 3'
         I   T   V   V   E   S   G /   * *********

Domain 2                 /    3'NonCoding
PΔ4  5' TAC AGA CTC CAG GTG TCA TCC/ TAGCTTCCTGTAGGGGGCTG 3'
         Y   R   L   Q   V   S   S /   * *********

Domain 1                 /    3'NonCoding
PΔ5  5' CTC TAC ATC TTT GTG CCA GAT CCC/ TAGCTTCCTGTAGGGGGCTG 3'
         L   Y   I   F   V   P   D   P /   * ********

Signal Sequence     :   Domain 1  /       Domain 2
PΔ6  5' CAG ATC TCT CAG GGC:CTG GTC/ACC GTG GGC TTC CTC CCT AAT CAT 3'
         Q   I   S   Q   G : L   V / T   V   G   F   L   P   N   D Signal Sequence     :   Domain 1  /       Domain 3
PΔ7  5' CAG ATC TCT CAG GGC:CTG GTC/ATC AAC GTC TCT GTG AAC GCA GTG CAG3'
         Q   I   S   Q   G : L   V / I   N   V   S   V   N   A   V   Q Signal Sequence     :   Domain 1  /       Domain 4
PΔ8  5' CAG ATC TCT CAG GGC:CTG GTC/ TAC GTG CGG CTC CTG GGA GAG CTG 3'
         Q   I   S   Q   G : L   V / Y   V   R   L   L   G   E   V Signal Sequence     :   Domain 1  /       Domain 5
PΔ9  5' CAG ATC TCT CAG GGC : CTG GTC / GTC CGA GTG CTG GAG CTA AGT 3'
         Q   I   S   Q   G   : L   V / V   R   V   L   W   L   A
```

TABLE 12

PROPOSED HUMAN A-type PDGF-R MUTAGENESIS OLIGOMERS

```
              Domain 5                 /    3'NonCoding
PΔ101  5' GCT CCC ACC CTG CGT TCT GAA/ TAACTGGCGGATTCGAGGGG 3'
           A   P   T   L   R   S   E /   * *********

Domain 4                 /    3'NonCoding
PΔ102  5' GAA CTG TTA ACT CAA GTT CCT/ TAACTGGCGGATTCGAGGGG 3'
           E   L   L   T   Q   V   P /   * *********

Domain 3                 /    3'NonCoding
PΔ103  5' ATT TCT GTC CAT GAG AAA GGT/ TAACTGGCGGATTCGAGGGG 3'
           I   S   V   H   E   K   G /   * *********

Domain 2                 /    3'NonCoding
PΔ104  5' TAT GCT TTA AAA GCA ACA TCA/ TAACTGGCGGATTCGAGGGG 3'
           Y   A   L   K   A   T   S /   * *********

Domain 1                 /    3'NonCoding
PΔ105  5' ATT TAC ATC TAT GTG CCA GAC CCA/ TAACTGGCGGATTCGAGGGG 3'
           I   Y   I   Y   V   P   D   P /   * *********

Signal Sequence     :  Domain 1  /       Domain 2
PΔ106  5' AGC CTA ATC CTC TGC CAG CTT/ GAT GTA GCC TTT GTA CCT CTA GGA 3'
           S   L   I   L   C : Q   L / D   V   A   F   V   P   L   G Signal Sequence     :  Domain 1  /       Domain 3
PΔ107  5' AGC CTA ATC CTC TGC CAG CTT/ GAG CTG GAT CTA GAA ATG GAA GCT CTT 3'
           S   L   I   L   C : Q   L / E   L   D   L   E   M   E   A   L
```

TABLE 12-continued

PROPOSED HUMAN A-type PDGF-R MUTAGENESIS OLIGOMERS

```
        Signal Sequence   :  Domain 1    /       Domain 4
PA108  5' AGC CTA ATC CTC TGC CAG CTT/ TTC ATT GAA ATC AAA CCC ACC TTC 3'
          S   L   I   L   C  : Q   L /  F   I   E   I   K   P   T   F Signal Sequence   :  Domain 1    /       Domain 5
PA109  5' AGC CTA ATC CTC TGC CAG CTT/ TCA TCC ATT CTG GAC TTG GTC 3'
          S   L   I   L   C  : Q   L /  S   S   I   L   D   L   V
```

In accordance with this invention any isolated DNA sequence which encodes substantially a PDGF-R complete structural sequence can be used as a probe. Alternatively, any DNA sequence that encodes a PDGF-R hydrophobic signal sequence and its translational start site may be used. An isolated partial DNA sequence which substantially encodes intact domains exhibiting PDGF-R activity (e.g., ligand or PDGF-R binding) is also part of this invention. Preferred probes are cDNA clones of PDGF receptor polypeptides.

The DNA sequences used in this invention will usually comprise intact domain structures, typically at least about 5 codons (15 nucleotides), more typically at least about 9 codons, usually at least about 13 codons, more usually at least about 18 codons, preferably at least about 25 codons and more preferably at least about 35 codons. One or more introns may also be present. This number of nucleotides is usually about the minimal length required for a successful probe that would hybridize specifically with a PDGF receptor sequence. For example, epitopes characteristic of a PDGF-R may be encoded in short peptides. Usually the wild-type sequence will be employed, in some instances one or more mutations may be introduced, such as deletions, substitutions, insertions, or inversions. These modifications may result in changes in the amino acid sequence, provide silent mutations, modify a restriction site, or provide specific mutations. The genomic sequence will usually not exceed about 200 kb, more usually not exceed about 100 kb, preferably not greater than about 0.5 kb.

Portions of the DNA sequence having at least about 10 nucleotides from a DNA sequence encoding an PDGF receptor peptide will typically be used, more typically at least about 15 nucleotides, usually at least about 20 nucleotides, more usually at least about 25 nucleotides, and preferably at least about 30 nucleotides. The probes will typically be less than about 6 kb, usually fewer than about 3.0 kb, and preferably less than about 1 kb. The probes may also be used to determine whether mRNA encoding a specific PDGF-R is present in a cell or different tissues.

The natural or synthetic DNA fragments coding for a desired platelet-derived growth factor receptor fragment will usually be incorporated into DNA constructs capable of introduction to and expression in an in vitro cell culture. Often the DNA constructs will be suitable for replication in a unicellular host, such as yeast or bacteria, but may also be intended for introduction to, with and without integration within the genome, cultured mammalian, or plant or other eukaryotic cell lines. Human cells may be preferred hosts. Higher eukaryote host cells will often be preferred because their glycosylation and protein processing patterns more likely simulate human processing. DNA constructs prepared for introduction into bacteria or yeast will typically include a replication system recognized by the host, the intended DNA fragment encoding the desired receptor polypeptide construct, transcriptional and translational initiation regulatory sequences operably linked to the polypeptide encoding segment, and transcriptional and translational termination regulatory sequences operably linked to the polypeptide encoding segment. The transcriptional regulatory sequences will typically include a heterologous enhancer or promoter which is recognized by the host. The selection of an appropriate promoter will depend upon the host, but promoters such as the trp, lac, and phage promoters, tRNA promoters, and glycolytic enzyme promoters are known and available. See, e.g., Sambrook et al. (1989). Conveniently available expression vectors which include the replication system and transcriptional and translational regulatory sequences together with the insertion site for the platelet-derived growth factor receptor DNA sequence may be employed. Examples of workable combinations of cell lines and expression vectors are described, e.g., in Sambrook et al. (1989); see also, Metzger et al. (1988) Nature 334:31–36.

Expression vectors for these cells can include expression control sequences, such as an origin of replication, a promoter, an enhancer and necessary processing information sites, e.g., ribosome-binding sites, RNA splice sites, polyadenylation sites, and transcriptional terminator sequences. Preferably, the enhancers or promoters will be those naturally associated with genes encoding the PDGF receptor polypeptides, although it will be understood that in many cases others will be equally or more appropriate. Other preferred expression control sequences are enhancers or promoters derived from viruses, such as SV40, Adenovirus, Bovine Papilloma Virus, and the like.

Similarly, preferred promoters are those found naturally in immunoglobulin-producing cells, see, e.g., U.S. Pat. No. 4,663,281, which is incorporated herein by reference, but SV40, polyoma virus, cytomegalovirus (human or murine) and the LTR from various retroviruses, e.g., murine leukemia virus, murine or Rous sarcoma virus and HIV, may be utilized, as well as promoters endogenous to PDGF-R genes. See, Enhancers and Eukaryotic Gene Expression, (1983) Cold Spring Harbor Press, New York, which is incorporated herein by reference.

The vectors containing the DNA segments of interest, e.g., a PDGF receptor polypeptide gene or cDNA sequence, can be transferred into the host cell by well-known methods, which vary depending on the type of cellular host. For example, calcium chloride transfection is commonly utilized for prokaryotic cells, whereas calcium phosphate treatment may be used for other cellular hosts. See generally, Sambrook et al. (1989) Molecular Cloning: A Laboratory Manual (2d ed.) CSH Press, which is incorporated herein by reference. The term "transformed cell" is meant to also include the progeny of a transformed cell.

As with the purified polypeptides, the nucleic acid segments associated with the ligand-binding segment, the extracellular domain and the intracellular domain are particularly useful. These gene segments will be used as probes for screening for new genes exhibiting similar biological activities, though the controlling elements of these genes may also be of importance.

IV. Methods for Making PDGF Receptor Polypeptide Constructs

DNA sequences may also be used to express PDGF-R polypeptides. For example, a DNA sequence of from about 21 nucleotides (encoding about 7 amino acids) to about 2.1 kb (about 700 amino acids) may be used to express a polypeptide having a PDGF receptor specific activity, typically ligand-binding. In particular, constructs retaining the ligand binding regions will be useful, as these constructs will possess binding activity.

In particular, various synthetic linkers and probes may be constructed to facilitate genetic engineering of the PDGF-R nucleic acid sequences. Polymerase chain reaction (PCR) techniques can be applied to producing large quantities of fragments or segments useful in the proper manipulation of the sequences encoding the constructs. See, e.g., Innis et al. (1990) PCR Protocols, Academic Press. Alternatively, nucleic acid synthesizers can produce sufficiently large quantities of fragments for hybridizing to any preselected sequence, e.g., from Table 1 or 2, or for manipulating the sequence to add or delete specific domains or segments. Particularly important segments will be the LBR's.

Large quantities of the receptor proteins may be prepared by expressing the whole receptor or parts of the receptor contained in the expression vehicles in compatible hosts such as E. coli, yeast, mammalian cells, insect cells, or frog oocytes. The expression vehicles may be introduced into the cells using methods well known in the art such as calcium phosphate precipitation (discussed below), lipofectin electroporation, or DEAE dextran transformation.

Usually the mammalian cell hosts will be immortalized cell lines. To study the characteristics of a PDGF-R and its corresponding ligand, it will be useful to transfect, or transform mammalian cells which lack or have low levels of a PDGF receptor. Preferably, a signal sequence can serve to direct the peptide to the cell membrane or for secretion. Cells lacking significant amounts of PDGF receptors include Chinese hamster ovary (CHO) cells, most epithelial cell lines, and various human tumor cell lines.

Transformed or transfected cells can be selected which incorporate a DNA sequence which encodes a receptor that is functionally equivalent to a wild-type receptor thereby conferring a PDGF-sensitive mitogenic response. Such cells will enable the analysis of the binding properties of various added PDGF receptor polypeptides. Transfected cells may also be used to evaluate the effectiveness of a composition or drug as a PDGF antagonist or agonist. The level of receptor tyrosine kinase activity or the rate of nucleic acid synthesis can be determined by contacting transfected cells with drugs or ligands and comparing the effects of various ligand analogues against the controls. Although the most common procaryote cells used as hosts are strains of E. coli, other prokaryotes such as Bacillus subtilis or Pseudomonas may also be used. The DNA sequences of the present invention, including fragments or portions of the sequence encoding for receptor polypeptides comprising intact structural domains, a portion of the receptor, or a polypeptide having an PDGF-R activity, can be used to prepare an expression vehicle or construct for a PDGF-R polypeptide or polypeptide having a PDGF-R activity. Usually the control sequence will be a eukaryotic promoter for expression in a mammalian cell. In some vehicles the receptor's own control sequences may also be used. A common prokaryotic plasmid vector for transforming E. coli is pBR322 or its derivatives, e.g. the plasmid pkt279 (Clontech), see Bolavar et al. (1977) Gene, 2:95. The prokaryotic vectors may also contain prokaryotic promoters for transcription initiation, optionally with an operator. Examples of most commonly used prokaryotic promoters include the beta-lactamase (penicillinase); lactose (lac) promoter, see Cheng et al. (1977) Nature, 198:1056; tryptophan promoter (trp), see Goeddell et al. (1980) Nucleic Acid Res., 8: 457); $P_L$ promoter; and the N-gene ribosome binding site, see Shimatake et al. (1981) Nature, 292:128-; each of which is hereby incorporated herein by reference.

Promoters used in conjunction with yeast can be promoters derived from the enolase gene, see Holland et al. (1981) J. Biol. Chem., 256:1385; or the promoter for the synthesis of glycolytic enzymes such as 3-phosphoglycerate kinase, see Hitzeman et al. (1980) J. Biol. Chem., 255:.

Appropriate non-native mammalian promoters will include the early and late promoters from SV40, see Fiers et al. (1978) Nature, 273:113; or promoters derived from murine muloney leukemia virus, mouse mammary tumor virus, avian sarcoma viruses, adenovirus II, bovine papilloma virus, or polyoma. In addition, the construct may be joined to an amplifiable gene, e.g. dihydrofolate reductase (DHFR) so that multiple copies of the PDGF receptor gene may be made. See, e.g., Kaufman et al. (1985) Mol. and Cell. Biol. 5:1750–1759; and Levinson et al. EPO publication nos. 0117059 and 0117060, each of which is incorporated hereby by reference.

Prokaryotes may be transformed by various methods, including using $CaCl_2$, see Cohen (1972) Proc. Nat'l Acad. Sci. USA, 69:2110; or the RbCl method, see Maniatis et al. (1982) Molecular Cloning: A Laboratory Manual, Cold Spring Harbor Press. Yeast may be transformed, e.g., using a method described by Van Solingen et al. (1977) J. Bacteriol. 130:946; or Hsiao et al. (1979) Proc. Nat'l Acad. Sci. USA 76:3829. With respect to eukaryotes, mammalian cells may be transfected using a calcium phosphate precipitation method, see, e.g., Graham and van der Eb (1978) Virology, 52:546; or by lipofectin (BRL) or retroviral infection, see, e.g., Gilboa (1983) Experimental Manipulation of Gene Expression, Chap. 9, Academic Press P. 175. The actual expression vectors containing appropriate sequences may be prepared according to standard techniques involving ligation and restriction enzymes. See e.g., Maniatis supra. Commercially available restriction enzymes for cleaving specific sites of DNA may be obtained from New England BioLabs, Beverly, Mass.

Particular cotransformations with other genes may be particularly useful. For example, it may be desired to coexpress the nucleic acid with another processing enzyme. Such enzymes include signal peptidase, tertiary conformation conferring enzymes, or glycosylating enzymes. This expression method may provide processing functions which otherwise might be lacking in the expression host, e.g., mammalian-like glycosylation in a prokaryote expression system. Alternatively, the host cell selected for expression may be chosen on the basis of the natural expression of those processing enzymes.

Cell clones are selected by using markers depending on the mode of the vector construction. The marker may be on the same or a different DNA molecule preferably the same DNA molecule. With mammalian cells the receptor gene itself may be the best marker. In prokaryotic hosts the transformant may be selected by resistance to ampicillin, tetracycline, or other antibiotics. Production of a particular product based on temperature sensitivity or compensation may serve as appropriate markers. Various methods may be used to harvest and purify the PDGF-R receptor protein or peptide fragment. The peptide may be isolated from a lysate of the host. The peptide may be isolated from the cell supernatant if the peptide is secreted. The PDGF-R peptide is then further purified as discussed above using HPLC, electrophoresis, or affinity chromatography, e.g., immuno-affinity or ligand affinity.

Another method which can be used to isolate cDNA clones of PDGF-R related species involves the use of the polymerase chain reaction (PCR). See, e.g., Saiki et al. (1985) *Science* 230:1350. In this approach two oligonucleotides corresponding to distinct regions of the PDGF-R sequence are synthesized and then used in the PCR reaction, typically to amplify receptor-related mRNA transcripts from an mRNA source. Annealing of the oligonucleotides and PCR reactions are performed under conditions of reduced stringency. The resulting amplified fragments are subcloned, and the resulting recombinant colonies are probed with $^{32}$P-labeled full-length PDGF-R cDNA. Clones which hybridize under low but not high stringency conditions represent PDGF-R related mRNA transcripts. This approach can also be used to isolate variant PDGF-R cDNA species which arise as a result of alternative splicing, see Frohman et al. (1988) *Proc. Nat'l Acad. Sci. USA*, 85:8998.

V. Antibodies

Polyclonal and/or monoclonal antibodies to the various PDGF receptor constructs, receptor peptides, and peptide fragments may also be prepared. Peptide fragments may be prepared synthetically in a peptide synthesizer and coupled to a carrier molecule (i.e., keyhole limpet hemocyanin) and injected into rabbits over several months. The rabbit sera is tested for immunoreactivity to the PDGF receptor protein or fragment. Monoclonal antibodies may be made by injecting mice with PDGF-R protein, PDGF-R polypeptides, or mouse cells expressing high levels of the cloned PDGF receptor on its cell surface. Monoclonal antibodies will be screened by ELISA and tested for specific immunoreactivity with the PDGF receptor protein or polypeptides thereof. See, Harlow and Lane (1988) *Antibodies: A Laboratory Manual*, CSHarbor Press, which is hereby incorporated herein by reference. These antibodies will be useful in assays as well as pharmaceuticals.

Once a sufficient quantity of the desired PDGF receptor polypeptide construct has been obtained, the protein may be used for various purposes. A typical use is the production of antibodies specific for binding to epitopes characteristic of these receptors. These antibodies may be either polyclonal or monoclonal and may be produced by in vitro or in vivo techniques.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species may be substituted for a mouse or rabbit, typically a mammal, but possibly a bird or other animal.

An immunological response is usually assayed with an immunoassay. Normally such immunoassays involve some purification of a source of antigen, for example, produced by the same cells and in the same fashion as the antigen was produced. The immunoassay may be a radioimmunoassay, an enzyme-linked assay (ELISA), a fluorescent assay, or any of many other choices, most of which are functionally equivalent but may exhibit particular advantages under specific conditions.

Monoclonal antibodies with affinities of at least about $10^6 M^{-1}$ preferably $10^8$, $10^{10}$, or higher will be made by standard procedures as described, e.g., in Harlow and Lane, (1988) *Antibodies: A Laboratory Manual*, CSH Press; or Goding, (1986) *Monoclonal Antibodies: Principles and Practice* (2d ed) Academic Press, New York, which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al. "Generation of a Large Combinatorial Library of the Immunoglobulin Repertoire in Phage Lambda," *Science* 246:1275–1281 (1989), hereby incorporated herein by reference. The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescens, chemiluminescers, magnetic particles and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

Antibodies of particular interest are those raised against the ligand binding regions. These will include some antibodies which function as ligands. Or, antibodies may be used to select for compounds which could serve as ligands for modified receptors. See, e.g., Meyer (1990) *Nature* 347:424–425; and Pain et al. (1990) *Nature* 347:444–447; each of which is hereby incorporated herein by reference.

VIII. Methods for Use

The present invention provides platelet-derived growth factor receptor (PDGF-R) polypeptide purification methods as well as methods for synthesizing PDGF receptors within cells. Also provided are homogeneous receptors produced by these methods, nucleic acid sequences encoding the receptors or portions of the receptors, as well as expression vehicles containing these sequences, cells comprising the PDGF-receptors, and antibodies to the receptors. In particular, the present invention provides methods for assaying binding and other activities of receptor-like proteins having rearranged combinations of the domains.

The extracellular region of the human type B PDGF receptor protein has been used to successfully bind PDGF BB ligand in a receptor activation assay. PDGF BB ligand binding to NIH3T3 cell-associated PDGF receptors is measured. Ligand binding causes phosphorylation (activation) of the cell associated receptors. Receptor phosphorylation is followed in a multi-step process which first involves solubilization of NIH3T3 cells and separation of cell proteins by electrophoresis of cell extracts on sodium dodecyl sulfate polyacrylamide gels. Gels are blotted onto nitrocellulose and treated with antiphosphotyrosine monoclonal antibodies to aid in the detection of phosphorylated PDGF receptor.

Monoclonal antibodies are visualized through autoradiography of antibody-associated 125-I protein A which has been introduced at the terminal stage of the assay.

If human type B receptor protein (at about a 60 fold molar excess to PDGF BB ligand) is preincubated with ligand for 1 hour prior to incubation with NIH3T3 cells, there is no cell-associated PDGF receptor phosphorylation. This indicates that the human type B PDGF receptor protein binds PDGF BB ligand in solution and prevents the ligand from activating cell-associated PDGF receptors. Thus, polypeptides which contain LBR's may be used to block normal PDGF responses.

The domain containing structures of the present invention will find use both as diagnostic and therapeutic reagents. The receptor polypeptides may be used as affinity reagents for detecting or binding ligand, as well as for interacting with receptor-like proteins, e.g., affecting receptor protein dimerization. The polypeptides will also be useful as reagents for detecting or purifying other proteins which associate with the receptors or fragments thereof.

The receptor polypeptides will also find use in generating other reagents, e.g., antibodies specific for binding epitopes peculiar to the modified receptors. In particular, antibodies raised against newly formed ligand binding determining segments may serve as ligands for the modified receptors. These techniques may provide for separating various functionalities of the receptors, thereby isolating each of the different effector functions from others, in response to PDGF binding.

The modified receptors of the present invention also provide methods for assaying ligands for them. For example, soluble ligand binding fragments will be useful as competing sites for ligand binding, a useful property in a ligand binding assay. In particular, the present invention provides an assay to screen for PDGF binding inhibition, allowing screening of large numbers of compounds. These compounds may be assayed in vitro, which allows testing of cytotoxic or membrane disruptive compounds. The present solid phase system allows reproducible, sensitive, specific, and readily automated assay procedures. Polystyrene 96-well plates may be coated with the appropriate construct with LBR's to assay for ligand binding activity.

Moreover, modifications to the ligand binding domains will lead to binding region combinations with different ligand binding affinities. Thus, modulation of ligand effected response may be easily achieved by inclusion of the appropriate affinity modified analogue.

Solid phase assays using these modified receptors may also be developed, providing greater sensitivity or improved capacity over unmodified binding regions.

Diagnostic kits comprising these reagents are also provided. The kit typically comprise a compartmentalized enclosure, e.g., a plastic substrate having diagnostic reagents of the invention attached thereto. The package will typically also include various buffers, labeling reagents, and other reagents as appropriate for the diagnostic test to be performed. Instructions for use of the related reagents and interpretation of the results will be provided.

In particular, the important functional segment of the extracellular domain will usually be attached to a plastic or other solid phase substrate. The binding regions will usually be selected for a combination of the affinity and ligand binding spectrum of the modified binding segments. Appropriate ligands will often be introduced to determine the ligand binding activity and affinity. Different LBR combinations will be used, and can be used to test for differently modified, e.g., labeled, ligands.

In addition, the peptides will be useful for therapeutic administration. The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), (1990) *Goodman and Gilman's: The Pharmacological Basis of Therapeutics*, 8th ed., Pergamon Press; and *Remington's Pharmaceutical Sciences*, (1985) 7th ed., Mack Publishing Co., Easton, Pa.; each of which is hereby incorporated by reference. Methods for administration are discussed therein, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck & Co., Rahway, N.J. Because of the high affinity binding between PDGF and its receptors, low dosages of these reagents would be initially expected to be effective. Thus, dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier.

The pharmaceutical compositions will be administered by parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

Preferably, the pharmaceutical compositions are administered intravenously. Thus, this invention provides compositions for intravenous administration which comprise a solution of the compound dissolved or suspended in an acceptable carrier, preferably an aqueous carrier. A variety of aqueous carriers may be used, e.g., water, buffered water, 0.4% saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, preferably about 20% (see, *Remington's*, supra).

For aerosol administration, the compounds are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

The invention will better be understood by reference to the following illustrative examples. The following examples are offered by way of illustration and not by way of limitation.

EXPERIMENTAL

In general, standard techniques of recombinant DNA technology are described in various publications, e.g., Sambrook et al. (1989) *Molecular Cloning: A Laboratory Manual*, Cold Spring Harbor Laboratory; Ausubel et al. (1987) *Current Protocols in Molecular Biology*, vols. 1 and 2 and supplements; and Wu and Grossman (eds.) (1987) *Methods in Enzymology*, Vol. 53 (Recombinant DNA Part D); each of which is incorporated herein by reference.

I. Human Extracellular Region

Equivalent techniques for construction, expression, and determination of the physiological effect of truncation or deletion analogues of the soluble extracellular receptor fragments from the human receptor may be performed using the nucleic acid, polypeptide, and other reagents provided herein.

A. Type B Segments

Constructs of type B receptor polypeptides were made as follows:

The 3.9 kb EcoRI-Hind III cDNA fragment of the human type B hPDGF-R was subcloned into the EcoRI-Hind III site of M13 Mp18 to produce a vector Mp18PR. For techniques, see Maniatis et al. (1982) *Molecular Cloning: A Laboratory Manual*, Cold Spring Harbor, N.Y., which is incorporated herein by reference. Verification of subcloning was performed by restriction enzyme digestion analysis and dideoxy chain termination sequencing, as described by Sanger et al. (1977) *Proc. Nat'l Acad. Sic. USA* 74:5463. Oligonucleotide directed in vitro mutagenesis was performed according to the method described by Kunkel et al. (1987) *Methods in Enzymol.*, 154:367. The strategy for oligonucleotide directed in vitro deletion mutagenesis of Mp18PR is outlined in FIG. 1.

In brief, a series of oligonucleotides were designed to create a nested set of soluble type B hPDGF receptor extracellular regions by deletion mutagenesis. These domains are designated Domain 1 through Domain 5 (D1–D5), suitable for expression in an appropriate eukaryotic expression system. A description of the mutagenic oligonucleotides aligned with the corresponding regions of the human PDGF receptor are listed in Table 10. The resulting constructs are labeled as indicated in Table 13. The antisense strand was used for mutagenesis throughout. Mutagenesis of PΔ1, PΔ2, PΔ3, PΔ4, and PΔ5, utilized Mp18PR as the template and mutagenesis of PΔ6, PΔ7, PΔ8, and PΔ9, utilized MP 18 PΔ1 as the template. PΔ1, a 41 bp oligomer, introduced a TAG stop codon after $Lysine_{499}$ ($K_{499}$) of D5 and removed the transmembrane (TM) as well as entire intracellular kinase domain (K), producing an Mp18 PΔ1 (see FIG. 1). PΔ1 codes for $530_{aa}$ $148_{aa}$ precursor proteins.

TABLE 13

HUMAN TYPE B PDGF-R EXPRESSION CONSTRUCTS

| Soluble | Membrane Bound |
|---|---|
| pBJPΔ1 | pBJPR |
| pBJPΔ2 | |
| pBJPΔ3 | |
| pBJPΔ4 | |
| pBJPΔ5 | |
| pBJPΔ6 | |
| pBJPΔ7 | |
| pBJPΔ8 | |
| pBJPΔ9 | |

The human PDGF receptor constructs were subsequently subcloned into the EcoRI-Hind III site of pBJ1 a derivation of pCDL-SRα296, as described in Takabe et al. (1988) *Molec. Cell Biol.* 8:466, and co-transfected with pSV2NEO, as described by Southern and Berg (1982) *J. Mol. Appl. Gen.*, 1: 327, into Chinese hamster ovary cells (CHO). See FIGS. 2 and 3.

Function of the constructs was demonstrated as follows:

A sample of 0.33 nM PDGF BB ligand is preincubated for 1 hr at 4° C. under the following conditions:

1. a polyclonal antibody to human PDGF (this antibody recognizes human PDGF AA, PDGF BB and PDGF AB);
2. 18 nM (60 fold molar excess to PDGF BB) human type B PDGF receptor;
3. phosphate buffered saline solution that the receptor and antibody are in; or
4. no additions but the ligand itself.

In a duplicate set of experiments, 0.33 nM PDGF AA is incubated with three of the above preincubation conditions, e.g., 2, 3, and 4 above. The human type B PDGF receptor does not appreciably recognize PDGF AA but this ligand will still activate cell-associated human type A PDGF receptor from NIH3T3 cells and so is a control for human type B PDGF receptor specificity and PDGF BB-dependent activation versus nonspecific general cellular effect, e.g., cytotoxicity.

The preincubated materials were in a final volume of 0.5 ml. They were placed in one well each of a six well tissue culture dish containing a confluent layer of serum starved (quiescent) NIH3T3 cells which were chilled to 4° C. The cells and incubation mixtures were agitated, e.g., rocked, at 4° C. for 2 h. They were then washed twice with 4° C. phosphate buffered saline. Forty μl of 125 mM Tris (hydroxymethyl)amino methane (Tris), pH 6.8, 20% (v/v) glycerol, 2% (w/v) sodium dodecyl sulfate (SDS), 2% (v/v) 2-mercaptoethanol, and 0.001% bromphenol blue, (known as SDS sample buffer), was added per microtiter well followed by 40 μl of 100 mM Tris, pH 8.0, 30 mM sodium pyrosphoshate, 50 mM sodium fluoride, 5 mM ethylenediaminetetraacetic acid (EDTA), 5 mM ethylenebis (oxyethylenenitrilio)tetraacetic acid, 1% (w/v) SDS, 100 mM dithiothreitol, 2 mM phenylmethylsulfonylfluoride (PMSF), and 200 μM sodium vanadate was added to the cells. The cells were solubilized and 40 μl additional SDS sample buffer was added to the solubilizate. This material was boiled 5 minutes and loaded onto a single gel sample well of a 7.5% sodium dodecyl sulfate polyacrylamide gel. Cellular proteins were separated by electrophoresis.

The separated proteins were transferred to nitrocellulose by electrotransfer and the resulting "Western blot" was incubated with 3 changes of 0.5% (w/v) sodium chloride, 5 mg/ml bovine serum albumin, 50 mM Tris, pH 7.5, (designated blocking buffer) for 20 minutes each at room temperature. A 1/1000 dilution of PY20 (a commercially available monoclonal antibody to phosphotyrosine [ICN]) in blocking buffer was incubated with the blot overnight at 4° C. The blot was washed 3 times for 20 minutes each at room temperature in blocking buffer. The blot was incubated with 4 μCi/40 ml of $^{125}$I-Protein A [Amersham] in blocking buffer for 1 hour at room temperature and washed 3 times for 20 minutes each at room temperature in blocking buffer. The blot was exposed to X-ray film for 48 h with one intensifying screen at −70° C. and developed with standard reagents.

Figure 4:
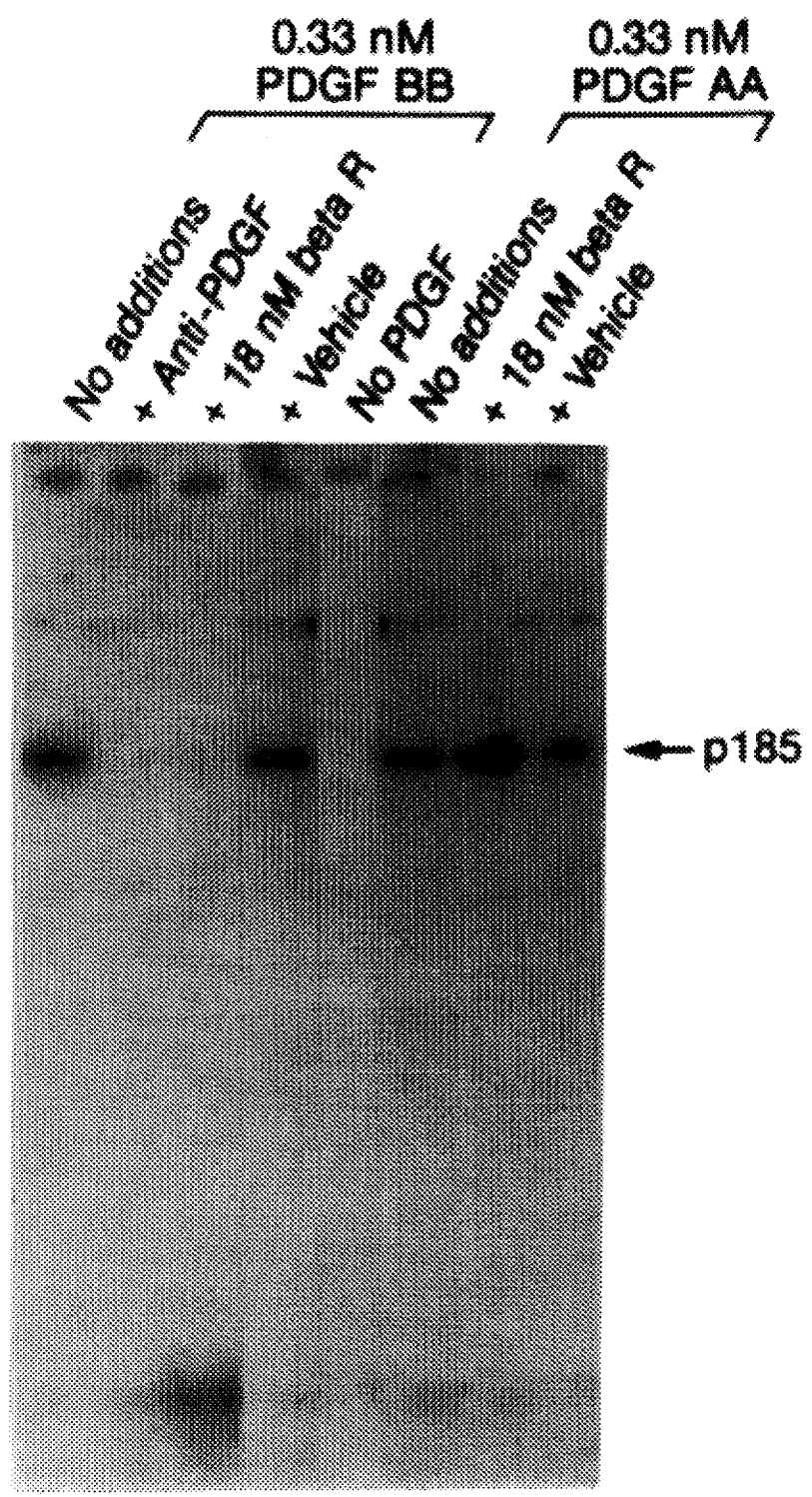

FIG. 4 shows the results of the autoradiogram with the conditions mentioned above plus the additional condition of no added ligand (no PDGF). This added condition defines the level of cell-associated receptor activation (e.g., phosphorylation) in the absence of any added ligand. Both the antibody and the human type B PDGF receptor neutralized the activation of cell-associated PDGF receptor by PDGF BB. This is apparently due to direct binding and sequestration of the ligand making it unavailable for PDGF receptor activation. p185 shows the receptor position.

B. Type A Sequence

Similar manipulations using the mutagenic oligonucleotides of Table 12 are used to construct the type A constructs listed in Table 15. Note that the type A constructs have not actually been produced, but would readily be produced by these methods. Similar assays are used to test the function of the constructs.

TABLE 15

SUGGESTED HUMAN TYPE A PDGF-R EXPRESSION CONSTRUCTS
type A

| Soluble | Membrane Bound |
|---------|----------------|
| pARSΔ1  | pARSR          |
| pARSΔ2  |                |
| pARSΔ3  |                |
| pARSΔ4  |                |
| pARSΔ5  |                |
| pARSΔ6  |                |
| pARSΔ7  |                |
| pARSΔ8  |                |
| pARSΔ9  |                |

C. PDGF Plate Assay

Polystyrene microtiter plates (Immulon, Dynatech Laboratories) were coated with the extracellular region fragment of the type B human PDGF receptor (described above) by incubating approximately 10–100 ng of this protein per well in 100 μl of 25 mM Tris, 75 mM NaCl, pH 7.75 for 12 to 18 h at 4° C. The protein was expressed in transfected CHO cells and collected in serum-free media (Gibco MEMα) at a concentration of 0.2–1 μg/ml, with a total protein concentration of 150–300 μg/ml.

The human PDGF type B receptor extracellular region fragment was concentrated and partially purified by passing the media over wheat germ-agglutinin-sepharose at 4° C. (at 48 ml/h) in the presence of 1 mM PMSF. After extensive washing, the protein was eluted in 0.3M N-acetylglucosamine, 25 mM Hepes, 100 mM NaCl, 1 mM PMSF, pH 7.4. This fraction was then applied to Sephacryl S-200 HR (Pharmacia) equilibrated in 0.15M ammonium bicarbonate pH 7.9. The fractions containing receptor (3–10 ng/μl) were detected by SDS-PAGE and Western blotting with a polyclonal rabbit antibody, made by standard methods, against a Domain 1 (D1) segment from the receptor external region. These fractions (3–10 ng/μl) were used to coat the microtiter wells as described above. The wells were then drained, rinsed once with 200 μl each of 0.5% gelatin (BioRad, EIA grade), 25 mM Hepes, 100 mM NaCl, pH 7.4, and incubated for 1–2 h at 24° C. with 150 μl of this same solution. The wells were drained and rinsed twice with 0.3% gelatin, 25 mM Hepes, 100 mM NaCl, pH 7.4 (150 μl each). 90 μl of the 0.3% gelatin solution was put in each well (wells used to test nonspecific binding received just 80 μl and then 10 μl of 0.01 mg/ml non-labeled PDGF in the 0.3% gelatin solution). PDGF BB (Amgen) was iodinated at 4° C. to 52,000 CPM/ng with di-iodo Bolton-Hunter reagent (Amersham) and approximately 40,000 CPM was added per well in 10 μl, containing 0.024% BSA, 0.4% gelatin, 20 mM Hepes, 80 mM NaCl, 70 mM acetic acid, pH 7.4. The plate was incubated for 2–3 h at 24° C., after which wells were washed three times with 150 μl each with 0.3% gelatin, 25 mM Hepes, 100 mM NaCl, pH 7.4. The bound radioactivity remaining was solubilized from the wells in 200 μl 1% SDS, 0.5% BSA, and counted in a gamma-counter. The nonspecific binding was determined in the presence of a 150-fold excess of unlabeled PDGF BB (Amgen) and was about 7% of the total bound $^{125}$I-PDGF.

Similar assays will be possible using type A receptor fragments. However, the type A receptor fragments are more sensitive to the presence of other proteins than the type B fragments, and appear to require a different well coating reagent from the gelatin. Hemoglobin is substituted for gelatin in the buffers at about the same concentrations. Other blocking proteins will be useful selected from, e.g., the Sigma Chemical Company. Titrations to optimize the protein type and concentration will be performed to find proteins which do not affect the receptor protein binding.

The present assays require less than 5 ng/well of receptor soluble form, which was expressed in transfected CHO cells, and partially purified by affinity and gel chromatography. Using iodinated PDGF-BB, the specific binding of less than 10 pg of ligand can be detected in an assay volume of 100 µg/well. At 4° C., the binding of $^{125}$I-PDGF BB to immobilized receptor is saturable and of high affinity. The Kd by Scatchard analysis was about 1 nM with $1.8 \times 10^{10}$ sites per well. The nonspecific binding, determined in the presence of a 100-fold excess of cold PDGF BB, was usually only about 5–10% of the total binding. The binding was also specific for the isoform of the ligand, insofar as excess cold PDGF AA did not inhibit $^{125}$I-PDGF BB binding. Furthermore, the external region of the type B PDGF receptor in solution competes with its immobilized form for binding iodinated PDGF BB ($IC_{50}$=5 nM). The $^{125}$I-PDGF BB bound after 4 h at 4° C. is only slowly dissociable in binding buffer ($t_{1/2}$>6 h), but is completely displaced by the addition of a 150-fold excess of unlabeled PDGF BB ($t_{1/2}$<1 h).

These studies were made possible by the availability of growth factor preparations devoid of contamination with other growth factors and by the use of a receptor expression system in which all of the measured PDGF responses could be attributed to this single transfected receptor cDNA.

All publications and patent applications herein are incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A type B or a type A human platelet-derived growth factor receptor (hPDGF-R) fragment consisting of one or two extracellular domains, said domains selected from the group consisting of one or two of only D1, D2, and D3, said fragment having platelet-derived growth factor receptor ligand binding activity, wherein said fragment binds a platelet-derived growth factor ligand with a $K_D$ of less than about 10 µM.

2. A hPDGF-R fragment of claim 1, wherein said fragment is soluble.

3. A hPDGF-R fragment of claim 1, wherein said fragment consists of domain D3.

4. A hPDGF-R fragment of claim 1, wherein said fragment is a contiguous sequence consisting of one or two extracellular domains, said domains selected from the group consisting of one or two of only D1, D2, and D3, and wherein said fragment is a contiguous peptide within a sequence selected from the group consisting of SEQ ID NO:2 and SEQ ID NO:4.

5. A hPDGF-R fragment consisting of the intra-cysteine portion of domain D3.

6. A hPDGF-R fragment of claim 3, wherein said fragment is soluble.

7. A fusion polypeptide consisting of the human platelet-derived growth factor receptor (hPDGF-R) fragment of claim 1 fused to a homologous or heterologous protein.

8. A type B or a type A hPDGF-R fragment wherein said fragment consists of extracellular domains D1 and D2, and wherein said fragment has platelet-derived growth factor receptor ligand binding activity, and binds a platelet-derived growth factor ligand with a $K_D$ of less than about 10 µM.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 5427 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo Sapiens
        ( B ) STRAIN: lambda gt10

( i x ) FEATURE:
        ( A ) NAME/KEY: CDS
        ( B ) LOCATION: 187..3504

( x i ) SEQUENCE DESCRIPTION: SEQ ID NO:1:

```
TGTTCTCCTG  AGCCTTCAGG  AGCCTGCACC  AGTCCTGCCT  GTCCTTCTAC  TCAGCTGTTA         60

CCCACTCTGG  GACCAGCAGT  CTTTCTGATA  ACTGGGAGAG  GGCAGTAAGG  AGGACTTCCT        120

GGAGGGGGTG  ACTGTCCAGA  GCCTGGAACT  GTGCCCACAC  CAGAAGCCAT  CAGCAGCAAG        180

GACACC ATG CGG CTT CCG GGT GCG ATG CCA GCT CTG GCC CTC AAA GGC              228
       Met Arg Leu Pro Gly Ala Met Pro Ala Leu Ala Leu Lys Gly
         1               5                  10

GAG CTG CTG TTG CTG TCT CTC CTG TTA CTT CTG GAA CCA CAG ATC TCT              276
Glu Leu Leu Leu Leu Ser Leu Leu Leu Leu Glu Pro Gln Ile Ser
 15                  20                  25                  30

CAG GGC CTG GTC GTC ACA CCC CCG GGG CCA GAG CTT GTC CTC AAT GTC              324
Gln Gly Leu Val Val Thr Pro Pro Gly Pro Glu Leu Val Leu Asn Val
                     35                  40                  45

TCC AGC ACC TTC GTT CTG ACC TGC TCG GGT TCA GCT CCG GTG GTG TGG              372
Ser Ser Thr Phe Val Leu Thr Cys Ser Gly Ser Ala Pro Val Val Trp
                 50                  55                  60
```

```
GAA CGG ATG TCC CAG GAG CCC CCA CAG GAA ATG GCC AAG GCC CAG GAT          420
Glu Arg Met Ser Gln Glu Pro Pro Gln Glu Met Ala Lys Ala Gln Asp
        65              70                  75

GGC ACC TTC TCC AGC GTG CTC ACA CTG ACC AAC CTC ACT GGG CTA GAC          468
Gly Thr Phe Ser Ser Val Leu Thr Leu Thr Asn Leu Thr Gly Leu Asp
    80              85                  90

ACG GGA GAA TAC TTT TGC ACC CAC AAT GAC TCC CGT GGA CTG GAG ACC          516
Thr Gly Glu Tyr Phe Cys Thr His Asn Asp Ser Arg Gly Leu Glu Thr
95                  100                 105                 110

GAT GAG CGG AAA CGG CTC TAC ATC TTT GTG CCA GAT CCC ACC GTG GGC          564
Asp Glu Arg Lys Arg Leu Tyr Ile Phe Val Pro Asp Pro Thr Val Gly
                115                 120                 125

TTC CTC CCT AAT GAT GCC GAG GAA CTA TTC ATC TTT CTC ACG GAA ATA          612
Phe Leu Pro Asn Asp Ala Glu Glu Leu Phe Ile Phe Leu Thr Glu Ile
            130                 135                 140

ACT GAG ATC ACC ATT CCA TGC CGA GTA ACA GAC CCA CAG CTG GTG GTG          660
Thr Glu Ile Thr Ile Pro Cys Arg Val Thr Asp Pro Gln Leu Val Val
        145                 150                 155

ACA CTG CAC GAG AAG AAA GGG GAC GTT GCA CTG CCT GTC CCC TAT GAT          708
Thr Leu His Glu Lys Lys Gly Asp Val Ala Leu Pro Val Pro Tyr Asp
160                 165                 170

CAC CAA CGT GGC TTT TCT GGT ATC TTT GAG GAC AGA AGC TAC ATC TGC          756
His Gln Arg Gly Phe Ser Gly Ile Phe Glu Asp Arg Ser Tyr Ile Cys
175                 180                 185                 190

AAA ACC ACC ATT GGG GAC AGG GAG GTG GAT TCT GAT GCC TAC TAT GTC          804
Lys Thr Thr Ile Gly Asp Arg Glu Val Asp Ser Asp Ala Tyr Tyr Val
                195                 200                 205

TAC AGA CTC CAG GTG TCA TCC ATC AAC GTC TCT GTG AAC GCA GTG CAG          852
Tyr Arg Leu Gln Val Ser Ser Ile Asn Val Ser Val Asn Ala Val Gln
            210                 215                 220

ACT GTG GTC CGC CAG GGT GAG AAC ATC ACC CTC ATG TGC ATT GTG ATC          900
Thr Val Val Arg Gln Gly Glu Asn Ile Thr Leu Met Cys Ile Val Ile
        225                 230                 235

GGG AAT GAT GTG GTC AAC TTC GAG TGG ACA TAC CCC CGC AAA GAA AGT          948
Gly Asn Asp Val Val Asn Phe Glu Trp Thr Tyr Pro Arg Lys Glu Ser
240                 245                 250

GGG CGG CTG GTG GAG CCG GTG ACT GAC TTC CTC TTG GAT ATG CCT TAC          996
Gly Arg Leu Val Glu Pro Val Thr Asp Phe Leu Leu Asp Met Pro Tyr
255                 260                 265                 270

CAC ATC CGC TCC ATC CTG CAC ATC CCC AGT GCC GAG TTA GAA GAC TCG         1044
His Ile Arg Ser Ile Leu His Ile Pro Ser Ala Glu Leu Glu Asp Ser
                275                 280                 285

GGG ACC TAC ACC TGC AAT GTG ACG GAG AGT GTG AAT GAC CAT CAG GAT         1092
Gly Thr Tyr Thr Cys Asn Val Thr Glu Ser Val Asn Asp His Gln Asp
            290                 295                 300

GAA AAG GCC ATC AAC ATC ACC GTG GTT GAG AGC GGC TAC GTG CGG CTC         1140
Glu Lys Ala Ile Asn Ile Thr Val Val Glu Ser Gly Tyr Val Arg Leu
        305                 310                 315

CTG GGA GAG GTG GGC ACA CTA CAA TTT GCT GAG CTG CAT CGG AGC CGG         1188
Leu Gly Glu Val Gly Thr Leu Gln Phe Ala Glu Leu His Arg Ser Arg
320                 325                 330

ACA CTG CAG GTA GTG TTC GAG GCC TAC CCA CCG CCC ACT GTC CTG TGG         1236
Thr Leu Gln Val Val Phe Glu Ala Tyr Pro Pro Pro Thr Val Leu Trp
335                 340                 345                 350

TTC AAA GAC AAC CGC ACC CTG GGC GAC TCC AGC GCT GGC GAA ATC GCC         1284
Phe Lys Asp Asn Arg Thr Leu Gly Asp Ser Ser Ala Gly Glu Ile Ala
                355                 360                 365

CTG TCC ACG CGC AAC GTG TCG GAG ACC CGG TAT GTG TCA GAG CTG ACA         1332
Leu Ser Thr Arg Asn Val Ser Glu Thr Arg Tyr Val Ser Glu Leu Thr
            370                 375                 380
```

```
CTG GTT CGC GTG AAG GTG GCA GAG GCT GGC CAC TAC ACC ATG CGG GCC         1380
Leu Val Arg Val Lys Val Ala Glu Ala Gly His Tyr Thr Met Arg Ala
        385             390             395

TTC CAT GAG GAT GCT GAG GTC CAG CTC TCC TTC CAG CTA CAG ATC AAT         1428
Phe His Glu Asp Ala Glu Val Gln Leu Ser Phe Gln Leu Gln Ile Asn
400             405             410

GTC CCT GTC CGA GTG CTG GAG CTA AGT GAG AGC CAC CCT GAC AGT GGG         1476
Val Pro Val Arg Val Leu Glu Leu Ser Glu Ser His Pro Asp Ser Gly
415             420             425             430

GAA CAG ACA GTC CGC TGT CGT GGC CGG GGC ATG CCG CAG CCG AAC ATC         1524
Glu Gln Thr Val Arg Cys Arg Gly Arg Gly Met Pro Gln Pro Asn Ile
            435             440             445

ATC TGG TCT GCC TGC AGA GAC CTC AAA AGG TGT CCA CGT GAG CTG CCG         1572
Ile Trp Ser Ala Cys Arg Asp Leu Lys Arg Cys Pro Arg Glu Leu Pro
        450             455             460

CCC ACG CTG CTG GGG AAC AGT TCC GAA GAG GAG AGC CAG CTG GAG ACT         1620
Pro Thr Leu Leu Gly Asn Ser Ser Glu Glu Glu Ser Gln Leu Glu Thr
        465             470             475

AAC GTG ACG TAC TGG GAG GAG GAG CAG GAG TTT GAG GTG GTG AGC ACA         1668
Asn Val Thr Tyr Trp Glu Glu Glu Gln Glu Phe Glu Val Val Ser Thr
480             485             490

CTG CGT CTG CAG CAC GTG GAT CGG CCA CTG TCG GTG CGC TGC ACG CTG         1716
Leu Arg Leu Gln His Val Asp Arg Pro Leu Ser Val Arg Cys Thr Leu
495             500             505             510

CGC AAC GCT GTG GGC CAG GAC ACG CAG GAG GTC ATC GTG GTG CCA CAC         1764
Arg Asn Ala Val Gly Gln Asp Thr Gln Glu Val Ile Val Val Pro His
            515             520             525

TCC TTG CCC TTT AAG GTG GTG GTG ATC TCA GCC ATC CTG GCC CTG GTG         1812
Ser Leu Pro Phe Lys Val Val Val Ile Ser Ala Ile Leu Ala Leu Val
        530             535             540

GTG CTC ACC ATC ATC TCC CTT ATC ATC CTC ATC ATG CTT TGG CAG AAG         1860
Val Leu Thr Ile Ile Ser Leu Ile Ile Leu Ile Met Leu Trp Gln Lys
        545             550             555

AAG CCA CGT TAC GAG ATC CGA TGG AAG GTG ATT GAG TCT GTG AGC TCT         1908
Lys Pro Arg Tyr Glu Ile Arg Trp Lys Val Ile Glu Ser Val Ser Ser
        560             565             570

GAC GGC CAT GAG TAC ATC TAC GTG GAC CCC ATG CAG CTG CCC TAT GAC         1956
Asp Gly His Glu Tyr Ile Tyr Val Asp Pro Met Gln Leu Pro Tyr Asp
575             580             585             590

TCC ACG TGG GAG CTG CCG CGG GAC CAG CTT GTG CTG GGA CGC ACC CTC         2004
Ser Thr Trp Glu Leu Pro Arg Asp Gln Leu Val Leu Gly Arg Thr Leu
            595             600             605

GGC TCT GGG GCC TTT GGG CAG GTG GTG GAG GCC ACA GCT CAT GGT CTG         2052
Gly Ser Gly Ala Phe Gly Gln Val Val Glu Ala Thr Ala His Gly Leu
        610             615             620

AGC CAT TCT CAG GCC ACG ATG AAA GTG GCC GTC AAG ATG CTT AAA TCC         2100
Ser His Ser Gln Ala Thr Met Lys Val Ala Val Lys Met Leu Lys Ser
        625             630             635

ACA GCC CGC AGC AGT GAG AAG CAA GCC CTT ATG TCG GAG CTG AAG ATC         2148
Thr Ala Arg Ser Ser Glu Lys Gln Ala Leu Met Ser Glu Leu Lys Ile
640             645             650

ATG AGT CAC CTT GGG CCC CAC CTG AAC GTG GTC AAC CTG TTG GGG GCC         2196
Met Ser His Leu Gly Pro His Leu Asn Val Val Asn Leu Leu Gly Ala
655             660             665             670

TGC ACC AAA GGA GGA CCC ATC TAT ATC ATC ACT GAG TAC TGC CGC TAC         2244
Cys Thr Lys Gly Gly Pro Ile Tyr Ile Ile Thr Glu Tyr Cys Arg Tyr
            675             680             685

GGA GAC CTG GTG GAC TAC CTG CAC CGC AAC AAA CAC ACC TTC CTG CAG         2292
Gly Asp Leu Val Asp Tyr Leu His Arg Asn Lys His Thr Phe Leu Gln
        690             695             700
```

| | | | | | | | | | | | | | | | | |
|---|---|---|---|---|---|---|---|---|---|---|---|---|---|---|---|---|
| CAC | CAC | TCC | GAC | AAG | CGC | CGC | CCG | CCC | AGC | GCG | GAG | CTC | TAC | AGC | AAT | 2340 |
| His | His | Ser | Asp | Lys | Arg | Arg | Pro | Pro | Ser | Ala | Glu | Leu | Tyr | Ser | Asn | |
| | | 705 | | | | 710 | | | | | 715 | | | | | |
| GCT | CTG | CCC | GTT | GGG | CTC | CCC | CTG | CCC | AGC | CAT | GTG | TCC | TTG | ACC | GGG | 2388 |
| Ala | Leu | Pro | Val | Gly | Leu | Pro | Leu | Pro | Ser | His | Val | Ser | Leu | Thr | Gly | |
| | 720 | | | | | 725 | | | | | 730 | | | | | |
| GAG | AGC | GAC | GGT | GGC | TAC | ATG | GAC | ATG | AGC | AAG | GAC | GAG | TCG | GTG | GAC | 2436 |
| Glu | Ser | Asp | Gly | Gly | Tyr | Met | Asp | Met | Ser | Lys | Asp | Glu | Ser | Val | Asp | |
| 735 | | | | | 740 | | | | | 745 | | | | | 750 | |
| TAT | GTG | CCC | ATG | CTG | GAC | ATG | AAA | GGA | GAC | GTC | AAA | TAT | GCA | GAC | ATC | 2484 |
| Tyr | Val | Pro | Met | Leu | Asp | Met | Lys | Gly | Asp | Val | Lys | Tyr | Ala | Asp | Ile | |
| | | | | 755 | | | | | 760 | | | | | 765 | | |
| GAG | TCC | TCC | AAC | TAC | ATG | GCC | CCT | TAC | GAT | AAC | TAC | GTT | CCC | TCT | GCC | 2532 |
| Glu | Ser | Ser | Asn | Tyr | Met | Ala | Pro | Tyr | Asp | Asn | Tyr | Val | Pro | Ser | Ala | |
| | | | 770 | | | | | 775 | | | | | 780 | | | |
| CCT | GAG | AGG | ACC | TGC | CGA | GCA | ACT | TTG | ATC | AAC | GAG | TCT | CCA | GTG | CTA | 2580 |
| Pro | Glu | Arg | Thr | Cys | Arg | Ala | Thr | Leu | Ile | Asn | Glu | Ser | Pro | Val | Leu | |
| | | 785 | | | | | 790 | | | | | 795 | | | | |
| AGC | TAC | ATG | GAC | CTC | GTG | GGC | TTC | AGC | TAC | CAG | GTG | GCC | AAT | GGC | ATG | 2628 |
| Ser | Tyr | Met | Asp | Leu | Val | Gly | Phe | Ser | Tyr | Gln | Val | Ala | Asn | Gly | Met | |
| | 800 | | | | | 805 | | | | | 810 | | | | | |
| GAG | TTT | CTG | GCC | TCC | AAG | AAC | TGC | GTC | CAC | AGA | GAC | CTG | GCG | GCT | AGG | 2676 |
| Glu | Phe | Leu | Ala | Ser | Lys | Asn | Cys | Val | His | Arg | Asp | Leu | Ala | Ala | Arg | |
| 815 | | | | | 820 | | | | | 825 | | | | | 830 | |
| AAC | GTG | CTC | ATC | TGT | GAA | GGC | AAG | CTG | GTC | AAG | ATC | TGT | GAC | TTT | GGC | 2724 |
| Asn | Val | Leu | Ile | Cys | Glu | Gly | Lys | Leu | Val | Lys | Ile | Cys | Asp | Phe | Gly | |
| | | | | 835 | | | | | 840 | | | | | 845 | | |
| CTG | GCT | CGA | GAC | ATC | ATG | CGG | GAC | TCG | AAT | TAC | ATC | TCC | AAA | GGC | AGC | 2772 |
| Leu | Ala | Arg | Asp | Ile | Met | Arg | Asp | Ser | Asn | Tyr | Ile | Ser | Lys | Gly | Ser | |
| | | | 850 | | | | | 855 | | | | | 860 | | | |
| ACC | TTT | TTG | CCT | TTA | AAG | TGG | ATG | GCT | CCG | GAG | AGC | ATC | TTC | AAC | AGC | 2820 |
| Thr | Phe | Leu | Pro | Leu | Lys | Trp | Met | Ala | Pro | Glu | Ser | Ile | Phe | Asn | Ser | |
| | | 865 | | | | | 870 | | | | | 875 | | | | |
| CTC | TAC | ACC | ACC | CTG | AGC | GAC | GTG | TGG | TCC | TTC | GGG | ATC | CTG | CTC | TGG | 2868 |
| Leu | Tyr | Thr | Thr | Leu | Ser | Asp | Val | Trp | Ser | Phe | Gly | Ile | Leu | Leu | Trp | |
| | 880 | | | | | 885 | | | | | 890 | | | | | |
| GAG | ATC | TTC | ACC | TTG | GGT | GGC | ACC | CCT | TAC | CCA | GAG | CTG | CCC | ATG | AAC | 2916 |
| Glu | Ile | Phe | Thr | Leu | Gly | Gly | Thr | Pro | Tyr | Pro | Glu | Leu | Pro | Met | Asn | |
| 895 | | | | | 900 | | | | | 905 | | | | | 910 | |
| GAG | CAG | TTC | TAC | AAT | GCC | ATC | AAA | CGG | GGT | TAC | CGC | ATG | GCC | CAG | CCT | 2964 |
| Glu | Gln | Phe | Tyr | Asn | Ala | Ile | Lys | Arg | Gly | Tyr | Arg | Met | Ala | Gln | Pro | |
| | | | | 915 | | | | | 920 | | | | | 925 | | |
| GCC | CAT | GCC | TCC | GAC | GAG | ATC | TAT | GAG | ATC | ATG | CAG | AAG | TGC | TGG | GAA | 3012 |
| Ala | His | Ala | Ser | Asp | Glu | Ile | Tyr | Glu | Ile | Met | Gln | Lys | Cys | Trp | Glu | |
| | | | 930 | | | | | 935 | | | | | 940 | | | |
| GAG | AAG | TTT | GAG | ATT | CGG | CCC | CCC | TTC | TCC | CAG | CTG | GTG | CTG | CTT | CTC | 3060 |
| Glu | Lys | Phe | Glu | Ile | Arg | Pro | Pro | Phe | Ser | Gln | Leu | Val | Leu | Leu | Leu | |
| | | 945 | | | | | 950 | | | | | 955 | | | | |
| GAG | AGA | CTG | TTG | GGC | GAA | GGT | TAC | AAA | AAG | AAG | TAC | CAG | CAG | GTG | GAT | 3108 |
| Glu | Arg | Leu | Leu | Gly | Glu | Gly | Tyr | Lys | Lys | Lys | Tyr | Gln | Gln | Val | Asp | |
| | 960 | | | | | 965 | | | | | 970 | | | | | |
| GAG | GAG | TTT | CTG | AGG | AGT | GAC | CAC | CCA | GCC | ATC | CTT | CGG | TCC | CAG | GCC | 3156 |
| Glu | Glu | Phe | Leu | Arg | Ser | Asp | His | Pro | Ala | Ile | Leu | Arg | Ser | Gln | Ala | |
| 975 | | | | | 980 | | | | | 985 | | | | | 990 | |
| CGC | TTG | CCT | GGG | TTC | CAT | GGC | CTC | CGA | TCT | CCC | CTG | GAC | ACC | AGC | TCC | 3204 |
| Arg | Leu | Pro | Gly | Phe | His | Gly | Leu | Arg | Ser | Pro | Leu | Asp | Thr | Ser | Ser | |
| | | | | 995 | | | | | 1000 | | | | | 1005 | | |
| GTC | CTC | TAT | ACT | GCC | GTG | CAG | CCC | AAT | GAG | GGT | GAC | AAC | GAC | TAT | ATC | 3252 |
| Val | Leu | Tyr | Thr | Ala | Val | Gln | Pro | Asn | Glu | Gly | Asp | Asn | Asp | Tyr | Ile | |
| | | | 1010 | | | | | 1015 | | | | | 1020 | | | |

```
ATC CCC CTG CCT GAC CCC AAA CCT GAG GTT GCT GAC GAG GGC CCA CTG    3300
Ile Pro Leu Pro Asp Pro Lys Pro Glu Val Ala Asp Glu Gly Pro Leu
        1025                1030                1035

GAG GGT TCC CCC AGC CTA GCC AGC TCC ACC CTG AAT GAA GTC AAC ACC    3348
Glu Gly Ser Pro Ser Leu Ala Ser Ser Thr Leu Asn Glu Val Asn Thr
    1040                1045                1050

TCC TCA ACC ATC TCC TGT GAC AGC CCC CTG GAG CCC CAG GAC GAA CCA    3396
Ser Ser Thr Ile Ser Cys Asp Ser Pro Leu Glu Pro Gln Asp Glu Pro
1055                1060                1065                1070

GAG CCA GAG CCC CAG CTT GAG CTC CAG GTG GAG CCG GAG CCG GAG CTG    3444
Glu Pro Glu Pro Gln Leu Glu Leu Gln Val Glu Pro Glu Pro Glu Leu
                1075                1080                1085

GAA CAG TTG CCG GAT TCG GGG TGC CCT GCG CCT CGG GCG GAA GCA GAG    3492
Glu Gln Leu Pro Asp Ser Gly Cys Pro Ala Pro Arg Ala Glu Ala Glu
            1090                1095                1100

GAT AGC TTC CTG TAGGGGGCTG GCCCCTACCC TGCCCTGCCT GAAGCTCCCC        3544
Asp Ser Phe Leu
            1105

CGCTGCCAGC ACCCAGCATC TCCTGGCCTG GCCTGGCCGG GCTTCCTGTC AGCCAGGCTG  3604
CCCTTATCAG CTGTCCCCTT CTGGAAGCTT TCTGCTCCTG ACGTGTTGTG CCCCAAACCC  3664
TGGGGCTGGC TTAGGAGGCA AGAAAACTGC AGGGGCCGTG ACCAGCCCTC TGCCTCCAGG  3724
GAGGCCAACT GACTCTGAGC CAGGGTTCCC CCAGGGAACT CAGTTTTCCC ATATGTAAGA  3784
TGGAAAGTT AGGCTTGATG ACCCAGAATC TAGGATTCTC TCCCTGGCTG ACAGGTGGGG   3844
AGACCGAATC CCTCCCTGGG AAGATTCTTG GAGTTACTGA GGTGGTAAAT TAACTTTTTT  3904
CTGTTCAGCC AGCTACCCCT CAAGGAATCA TAGCTCTCTC CTCGCACTTT TATCCACCCA  3964
GGAGCTAGGG AAGAGACCCT AGCCTCCCTG GCTGCTGGCT GAGCTAGGGC CTAGCCTTGA  4024
GCAGTGTTGC CTCATCCAGA AGAAAGCCAG TCTCCTCCCT ATGATGCCAG TCCCTGCGTT  4084
CCCTGGCCCG AGCTGGTCTG GGGCCATTAG GCAGCCTAAT TAATGCTGGA GGCTGAGCCA  4144
AGTACAGGAC ACCCCCAGCC TGCAGCCCTT GCCCAGGGCA CTTGGAGCAC ACGCAGCCAT  4204
AGCAAGTGCC TGTGTCCCTG TCCTTCAGGC CCATCAGTCC TGGGGCTTTT TCTTTATCAC  4264
CCTCAGTCTT AATCCATCCA CCAGAGTCTA GAAGGCCAGA CGGGCCCCGC ATCTGTGATG  4324
AGAATGTAAA TGTGCCAGTG TGGAGTGGCC ACGTGTGTGT GCCAGATATG GCCCTGGCTC  4384
TGCATTGGAC CTGCTATGAG GCTTTGGAGG AATCCCTCAC CCTCTCTGGG CCTCAGTTTC  4444
CCCTTCAAAA AATGAATAAG TCGGACTTAT TAACTCTGAG TGCCTTGCCA GCACTAACAT  4504
TCTAGAGTAT CCAGGTGGTT GCACATTTGT CCAGATGAAG CAAGGCCATA TACCCTAAAC  4564
TTCCATCCTG GGGTCAGCT GGGCTCCTGG GAGATTCCAG ATCACACATC ACACTCTGGG   4624
GACTCAGGAA CCATGCCCCT TCCCCAGGCC CCAGCAAGT CTCAAGAACA CAGCTGCACA   4684
GGCCTTGACT TAGAGTGACA GCCGGTGTCC TGGAAAGCCC CCAGCAGCTG CCCCAGGGAC  4744
ATGGGAAGAC CACGGGACCT CTTTCACTAC CCACGATGAC CTCCGGGGGT ATCCTGGGCA  4804
AAAGGGACAA AGAGGGCAAA TGAGATCACC TCCTGCAGCC CACCACTCCA GCACCTGTGC  4864
CGAGGTCTGC GTCGAAGACA GAATGGACAG TGAGGACAGT TATGTCTTGT AAAAGACAAG  4924
AAGCTTCAGA TGGGTACCCC AAGAAGGATG TGAGAGGTGG GCGCTTTGGA GGTTTGCCCC  4984
TCACCCACCA GCTGCCCCAT CCCTGAGGCA GCGCTCCATG GGGGTATGGT TTTGTCACTG  5044
CCCAGACCTA GCAGTGACAT CTCATTGTCC CCAGCCCAGT GGGCATTGGA GGTGCCAGGG  5104
GAGTCAGGGT TGTAGCCAAG ACGCCCCCGC ACGGGGAGGG TTGGGAAGGG GGTGCAGGAA  5164
GCTCAACCCC TCTGGGCACC AACCCTGCAT TGCAGGTTGG CACCTTACTT CCCTGGGATC  5224
```

```
CCAGAGTTGG TCCAAGGAGG GAGAGTGGGT TCTCAATACG GTACCAAAGA TATAATCACC      5284
TAGGTTTACA AATATTTTTA GGACTCACGT TAACTCACAT TTATACAGCA GAAATGCTAT      5344
TTTGTATGCT GTTAAGTTTT TCTATCTGTG TACTTTTTTT TAAGGGAAAG ATTTAATAT       5404
TAAACCTGGT GCTTCTCACT CAC                                              5427
```

( 2 ) INFORMATION FOR SEQ ID NO:2:

( i ) SEQUENCE CHARACTERISTICS:
        ( A ) LENGTH: 1106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Asp Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320
```

```
Glu Val Gly Thr Leu Gln Phe Ala Glu Leu His Arg Ser Arg Thr Leu
                325                 330                 335
Gln Val Val Phe Glu Ala Tyr Pro Pro Thr Val Leu Trp Phe Lys
            340                 345                 350
Asp Asn Arg Thr Leu Gly Asp Ser Ser Ala Gly Glu Ile Ala Leu Ser
            355                 360                 365
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
            405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
            435                 440                 445
Ser Ala Cys Arg Asp Leu Lys Arg Cys Pro Arg Glu Leu Pro Pro Thr
    450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
            485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Val Pro His Ser Leu
    515                 520                 525
Pro Phe Lys Val Val Val Ile Ser Ala Ile Leu Ala Leu Val Val Leu
    530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
            565                 570                 575
His Glu Tyr Ile Tyr Val Asp Pro Met Gln Leu Pro Tyr Asp Ser Thr
            580                 585                 590
Trp Glu Leu Pro Arg Asp Gln Leu Val Leu Gly Arg Thr Leu Gly Ser
        595                 600                 605
Gly Ala Phe Gly Gln Val Val Glu Ala Thr Ala His Gly Leu Ser His
    610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
            645                 650                 655
His Leu Gly Pro His Leu Asn Val Val Asn Leu Leu Gly Ala Cys Thr
            660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
            690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
            725                 730                 735
Asp Gly Gly Tyr Met Asp Met Ser Lys Asp Glu Ser Val Asp Tyr Val
```

-continued

```
                    740                         745                         750
Pro  Met  Leu  Asp  Met  Lys  Gly  Asp  Val  Lys  Tyr  Ala  Asp  Ile  Glu  Ser
               755                         760                    765

Ser  Asn  Tyr  Met  Ala  Pro  Tyr  Asp  Asn  Tyr  Val  Pro  Ser  Ala  Pro  Glu
          770                    775                         780

Arg  Thr  Cys  Arg  Ala  Thr  Leu  Ile  Asn  Glu  Ser  Pro  Val  Leu  Ser  Tyr
785                      790                         795                         800

Met  Asp  Leu  Val  Gly  Phe  Ser  Tyr  Gln  Val  Ala  Asn  Gly  Met  Glu  Phe
                    805                         810                    815

Leu  Ala  Ser  Lys  Asn  Cys  Val  His  Arg  Asp  Leu  Ala  Ala  Arg  Asn  Val
               820                         825                    830

Leu  Ile  Cys  Glu  Gly  Lys  Leu  Val  Lys  Ile  Cys  Asp  Phe  Gly  Leu  Ala
          835                         840                    845

Arg  Asp  Ile  Met  Arg  Asp  Ser  Asn  Tyr  Ile  Ser  Lys  Gly  Ser  Thr  Phe
     850                         855                    860

Leu  Pro  Leu  Lys  Trp  Met  Ala  Pro  Glu  Ser  Ile  Phe  Asn  Ser  Leu  Tyr
865                      870                         875                         880

Thr  Thr  Leu  Ser  Asp  Val  Trp  Ser  Phe  Gly  Ile  Leu  Leu  Trp  Glu  Ile
                    885                         890                         895

Phe  Thr  Leu  Gly  Gly  Thr  Pro  Tyr  Pro  Glu  Leu  Pro  Met  Asn  Glu  Gln
                    900                         905                    910

Phe  Tyr  Asn  Ala  Ile  Lys  Arg  Gly  Tyr  Arg  Met  Ala  Gln  Pro  Ala  His
               915                         920                    925

Ala  Ser  Asp  Glu  Ile  Tyr  Glu  Ile  Met  Gln  Lys  Cys  Trp  Glu  Glu  Lys
          930                         935                    940

Phe  Glu  Ile  Arg  Pro  Pro  Phe  Ser  Gln  Leu  Val  Leu  Leu  Leu  Glu  Arg
945                      950                         955                         960

Leu  Leu  Gly  Glu  Gly  Tyr  Lys  Lys  Lys  Tyr  Gln  Gln  Val  Asp  Glu  Glu
                    965                         970                    975

Phe  Leu  Arg  Ser  Asp  His  Pro  Ala  Ile  Leu  Arg  Ser  Gln  Ala  Arg  Leu
               980                         985                    990

Pro  Gly  Phe  His  Gly  Leu  Arg  Ser  Pro  Leu  Asp  Thr  Ser  Ser  Val  Leu
          995                         1000                   1005

Tyr  Thr  Ala  Val  Gln  Pro  Asn  Glu  Gly  Asp  Asn  Asp  Tyr  Ile  Ile  Pro
     1010                        1015                        1020

Leu  Pro  Asp  Pro  Lys  Pro  Glu  Val  Ala  Asp  Glu  Gly  Pro  Leu  Glu  Gly
1025                     1030                        1035                        1040

Ser  Pro  Ser  Leu  Ala  Ser  Ser  Thr  Leu  Asn  Glu  Val  Asn  Thr  Ser  Ser
                    1045                        1050                        1055

Thr  Ile  Ser  Cys  Asp  Ser  Pro  Leu  Glu  Pro  Gln  Asp  Glu  Pro  Glu  Pro
          1060                        1065                        1070

Glu  Pro  Gln  Leu  Glu  Leu  Gln  Val  Glu  Pro  Glu  Pro  Glu  Leu  Glu  Gln
     1075                        1080                        1085

Leu  Pro  Asp  Ser  Gly  Cys  Pro  Ala  Pro  Arg  Ala  Glu  Ala  Glu  Asp  Ser
     1090                        1095                   1100

Phe  Leu
1105
```

( 2 ) INFORMATION FOR SEQ ID NO:3:

( i ) SEQUENCE CHARACTERISTICS:
        ( A ) LENGTH: 4100 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: Homo Sapiens
    ( B ) STRAIN: lambda gt10

( i x ) FEATURE:
    ( A ) NAME/KEY: CDS
    ( B ) LOCATION: 129..3395

( x i ) SEQUENCE DESCRIPTION: SEQ ID NO:3:

```
TTGGAGCTAC AGGGAGAGAA ACAGAGGAGG AGACTGCAAG AGATCATTGG AGGCCGTGGG        60

CACGCTCTTT ACTCCATGTG TGGACATTC  ATTGCGGAAT AACATCGGAG GAGAAGTTTC       120

CCAGAGCT ATG GGG ACT TCC CAT CCG GCG TTC CTG GTC TTA GGC TGT CTT        170
         Met Gly Thr Ser His Pro Ala Phe Leu Val Leu Gly Cys Leu
          1               5                  10

CTC ACA GGG CTG AGC CTA ATC CTC TGC CAG CTT TCA TTA CCC TCT ATC        218
Leu Thr Gly Leu Ser Leu Ile Leu Cys Gln Leu Ser Leu Pro Ser Ile
 15              20                  25                  30

CTT CCA AAT GAA AAT GAA AAG GTT GTG CAG CTG AAT TCA TCC TTT TCT        266
Leu Pro Asn Glu Asn Glu Lys Val Val Gln Leu Asn Ser Ser Phe Ser
                 35                  40                  45

CTG AGA TGC TTT GGG GAG AGT GAA GTG AGC TGG CAG TAC CCC ATG TCT        314
Leu Arg Cys Phe Gly Glu Ser Glu Val Ser Trp Gln Tyr Pro Met Ser
             50                  55                  60

GAA GAA GAG AGC TCC GAT GTG GAA ATC AGA AAT GAA GAA AAC AAC AGC        362
Glu Glu Glu Ser Ser Asp Val Glu Ile Arg Asn Glu Glu Asn Asn Ser
         65                  70                  75

GGC CTT TTT GTG ACG GTC TTG GAA GTG AGC AGT GCC TCG GCG GCC CAC        410
Gly Leu Phe Val Thr Val Leu Glu Val Ser Ser Ala Ser Ala Ala His
     80                  85                  90

ACA GGG TTG TAC ACT TGC TAT TAC AAC CAC ACT CAG ACA GAA GAG AAT        458
Thr Gly Leu Tyr Thr Cys Tyr Tyr Asn His Thr Gln Thr Glu Glu Asn
 95                 100                 105                 110

GAG CTT GAA GGC AGG CAC ATT TAC ATC TAT GTG CCA GAC CCA GAT GTA        506
Glu Leu Glu Gly Arg His Ile Tyr Ile Tyr Val Pro Asp Pro Asp Val
                115                 120                 125

GCC TTT GTA CCT CTA GGA ATG ACG GAT TAT TTA GTC ATC GTG GAG GAT        554
Ala Phe Val Pro Leu Gly Met Thr Asp Tyr Leu Val Ile Val Glu Asp
            130                 135                 140

GAT GAT TCT GCC ATT ATA CCT TGT CGC ACA ACT GAT CCC GAG ACT CCT        602
Asp Asp Ser Ala Ile Ile Pro Cys Arg Thr Thr Asp Pro Glu Thr Pro
        145                 150                 155

GTA ACC TTA CAC AAC AGT GAG GGG GTG GTA CCT GCC TCC TAC GAC AGC        650
Val Thr Leu His Asn Ser Glu Gly Val Val Pro Ala Ser Tyr Asp Ser
    160                 165                 170

AGA CAG GGC TTT AAT GGG ACC TTC ACT GTA GGG CCC TAT ATC TGT GAG        698
Arg Gln Gly Phe Asn Gly Thr Phe Thr Val Gly Pro Tyr Ile Cys Glu
175                 180                 185                 190

GCC ACC GTC AAA GGA AAG AAG TTC CAG ACC ATC CCA TTT AAT GTT TAT        746
Ala Thr Val Lys Gly Lys Lys Phe Gln Thr Ile Pro Phe Asn Val Tyr
                195                 200                 205

GCT TTA AAA GCA ACA TCA GAG CTG GAT CTA GAA ATG GAA GCT CTT AAA        794
Ala Leu Lys Ala Thr Ser Glu Leu Asp Leu Glu Met Glu Ala Leu Lys
            210                 215                 220

ACC GTG TAT AAG TCA GGG GAA ACG ATT GTG GTC ACC TGT GCT GTT TTT        842
Thr Val Tyr Lys Ser Gly Glu Thr Ile Val Val Thr Cys Ala Val Phe
        225                 230                 235
```

```
AAC AAT GAG GTG GTT GAC CTT CAA TGG ACT TAC CCT GGA GAA GTG AAA        890
Asn Asn Glu Val Val Asp Leu Gln Trp Thr Tyr Pro Gly Glu Val Lys
240             245                 250

GGC AAA GGC ATC ACA ATG CTG GAA GAA ATC AAA GTC CCA TCC ATC AAA        938
Gly Lys Gly Ile Thr Met Leu Glu Glu Ile Lys Val Pro Ser Ile Lys
255             260                 265                 270

TTG GTG TAC ACT TTG ACG GTC CCC GAG GCC ACG GTG AAA GAC AGT GGA        986
Leu Val Tyr Thr Leu Thr Val Pro Glu Ala Thr Val Lys Asp Ser Gly
                275                 280                 285

GAT TAC GAA TGT GCT GCC CGC CAG GCT ACC AGG GAG GTC AAA GAA ATG       1034
Asp Tyr Glu Cys Ala Ala Arg Gln Ala Thr Arg Glu Val Lys Glu Met
            290                 295                 300

AAG AAA GTC ACT ATT TCT GTC CAT GAG AAA GGT TTC ATT GAA ATC AAA       1082
Lys Lys Val Thr Ile Ser Val His Glu Lys Gly Phe Ile Glu Ile Lys
        305                 310                 315

CCC ACC TTC AGC CAG TTG GAA GCT GTC AAC CTG CAT GAA GTC AAA CAT       1130
Pro Thr Phe Ser Gln Leu Glu Ala Val Asn Leu His Glu Val Lys His
320                 325                 330

TTT GTT GTA GAG GTG CGG GCC TAC CCA CCT CCC AGG ATA TCC TGG CTG       1178
Phe Val Val Glu Val Arg Ala Tyr Pro Pro Pro Arg Ile Ser Trp Leu
335                 340                 345                 350

AAA AAC AAT CTG ACT CTG ATT GAA AAT CTC ACT GAG ATC ACC ACT GAT       1226
Lys Asn Asn Leu Thr Leu Ile Glu Asn Leu Thr Glu Ile Thr Thr Asp
                355                 360                 365

GTG GAA AAG ATT CAG GAA ATA AGG TAT CGA AGC AAA TTA AAG CTG ATC       1274
Val Glu Lys Ile Gln Glu Ile Arg Tyr Arg Ser Lys Leu Lys Leu Ile
            370                 375                 380

CGT GCT AAG GAA GAA GAC AGT GGC CAT TAT ACT ATT GTA GCT CAA AAT       1322
Arg Ala Lys Glu Glu Asp Ser Gly His Tyr Thr Ile Val Ala Gln Asn
        385                 390                 395

GAA GAT GCT GTG AAG AGC TAT ACT TTT GAA CTG TTA ACT CAA GTT CCT       1370
Glu Asp Ala Val Lys Ser Tyr Thr Phe Glu Leu Leu Thr Gln Val Pro
400                 405                 410

TCA TCC ATT CTG GAC TTG GTC GAT GAT CAC CAT GGC TCA ACT GGG GGA       1418
Ser Ser Ile Leu Asp Leu Val Asp Asp His His Gly Ser Thr Gly Gly
415                 420                 425                 430

CAG ACG GTG AGG TGC ACA GCT GAA GGC ACG CCG CTT CCT GAT ATT GAG       1466
Gln Thr Val Arg Cys Thr Ala Glu Gly Thr Pro Leu Pro Asp Ile Glu
                435                 440                 445

TGG ATG ATA TGC AAA GAT ATT AAG AAA TGT AAT AAT GAA ACT TCC TGG       1514
Trp Met Ile Cys Lys Asp Ile Lys Lys Cys Asn Asn Glu Thr Ser Trp
            450                 455                 460

ACT ATT TTG GCC AAC AAT GTC TCA AAC ATC ATC ACG GAG ATC CAC TCC       1562
Thr Ile Leu Ala Asn Asn Val Ser Asn Ile Ile Thr Glu Ile His Ser
        465                 470                 475

CGA GAC AGG AGT ACC GTG GAG GGC CGT GTG ACT TTC GCC AAA GTG GAG       1610
Arg Asp Arg Ser Thr Val Glu Gly Arg Val Thr Phe Ala Lys Val Glu
480                 485                 490

GAG ACC ATC GCC GTG CGA TGC CTG GCT AAG AAT CTC CTT GGA GCT GAG       1658
Glu Thr Ile Ala Val Arg Cys Leu Ala Lys Asn Leu Leu Gly Ala Glu
495                 500                 505                 510

AAC CGA GAG CTG AAG CTG GTG GCT CCC ACC CTG CGT TCT GAA CTC ACG       1706
Asn Arg Glu Leu Lys Leu Val Ala Pro Thr Leu Arg Ser Glu Leu Thr
                515                 520                 525

GTG GCT GCT GCA GTC CTG GTG CTG TTG GTG ATT GTG ATC ATC TCA CTT       1754
Val Ala Ala Ala Val Leu Val Leu Leu Val Ile Val Ile Ile Ser Leu
            530                 535                 540

ATT GTC CTG GTT GTC ATT TGG AAA CAG AAA CCG AGG TAT GAA ATT CGC       1802
Ile Val Leu Val Val Ile Trp Lys Gln Lys Pro Arg Tyr Glu Ile Arg
        545                 550                 555
```

| | | | | | | | | | | | | | | | | |
|---|---|---|---|---|---|---|---|---|---|---|---|---|---|---|---|---|
| TGG | AGG | GTC | ATT | GAA | TCA | ATC | AGC | CCA | GAT | GGA | CAT | GAA | TAT | ATT | TAT | 1850 |
| Trp | Arg 560 | Val | Ile | Glu | Ser 565 | Ile | Ser | Pro | Asp | Gly 570 | His | Glu | Tyr | Ile | Tyr | |
| GTG | GAC | CCG | ATG | CAG | CTG | CCT | TAT | GAC | TCA | AGA | TGG | GAG | TTT | CCA | AGA | 1898 |
| Val 575 | Asp | Pro | Met | Gln | Leu 580 | Pro | Tyr | Asp | Ser | Arg 585 | Trp | Glu | Phe | Pro | Arg 590 | |
| GAT | GGA | CTA | GTG | CTT | GGT | CGG | GTC | TTG | GGG | TCT | GGA | GCG | TTT | GGG | AAG | 1946 |
| Asp | Gly | Leu | Val | Leu 595 | Gly | Arg | Val | Leu | Gly 600 | Ser | Gly | Ala | Phe | Gly 605 | Lys | |
| GTG | GTT | GAA | GGA | ACA | GCC | TAT | GGA | TTA | AGC | CGG | TCC | CAA | CCT | GTC | ATG | 1994 |
| Val | Val | Glu | Gly 610 | Thr | Ala | Tyr | Gly | Leu 615 | Ser | Arg | Ser | Gln | Pro 620 | Val | Met | |
| AAA | GTT | GCA | GTG | AAG | ATG | CTA | AAA | CCC | ACG | GCC | AGA | TCC | AGT | GAA | AAA | 2042 |
| Lys | Val | Ala 625 | Val | Lys | Met | Leu | Lys 630 | Pro | Thr | Ala | Arg | Ser 635 | Ser | Glu | Lys | |
| CAA | GCT | CTC | ATG | TCT | GAA | CTG | AAG | ATA | ATG | ACT | CAC | CTG | GGG | CCA | CAT | 2090 |
| Gln | Ala 640 | Leu | Met | Ser | Glu | Leu 645 | Lys | Ile | Met | Thr | His 650 | Leu | Gly | Pro | His | |
| TTG | AAC | ATT | GTA | AAC | TTG | CTG | GGA | GCC | TGC | ACC | AAG | TCA | GGC | CCC | ATT | 2138 |
| Leu 655 | Asn | Ile | Val | Asn | Leu 660 | Leu | Gly | Ala | Cys | Thr 665 | Lys | Ser | Gly | Pro | Ile 670 | |
| TAC | ATC | ATC | ACA | GAG | TAT | TGC | TTC | TAT | GGA | GAT | TTG | GTC | AAC | TAT | TTG | 2186 |
| Tyr | Ile | Ile | Thr | Glu 675 | Tyr | Cys | Phe | Tyr | Gly 680 | Asp | Leu | Val | Asn | Tyr 685 | Leu | |
| CAT | AAG | AAT | AGG | GAT | AGC | TTC | CTG | AGC | CAC | CAC | CCA | GAG | AAG | CCA | AAG | 2234 |
| His | Lys | Asn | Arg 690 | Asp | Ser | Phe | Leu | Ser 695 | His | His | Pro | Glu | Lys 700 | Pro | Lys | |
| AAA | GAG | CTG | GAT | ATC | TTT | GGA | TTG | AAC | CCT | GCT | GAT | GAA | AGC | ACA | CGG | 2282 |
| Lys | Glu | Leu 705 | Asp | Ile | Phe | Gly | Leu 710 | Asn | Pro | Ala | Asp | Glu 715 | Ser | Thr | Arg | |
| AGC | TAT | GTT | ATT | TTA | TCT | TTT | GAA | AAC | AAT | GGT | GAC | TAC | ATG | GAC | ATG | 2330 |
| Ser | Tyr 720 | Val | Ile | Leu | Ser | Phe 725 | Glu | Asn | Asn | Gly | Asp 730 | Tyr | Met | Asp | Met | |
| AAG | CAG | GCT | GAT | ACT | ACA | CAG | TAT | GTC | CCC | ATG | CTA | GAA | AGG | AAA | GAG | 2378 |
| Lys 735 | Gln | Ala | Asp | Thr 740 | Thr | Gln | Tyr | Val | Pro 745 | Met | Leu | Glu | Arg | Lys 750 | Glu | |
| GTT | TCT | AAA | TAT | TCC | GAC | ATC | CAG | AGA | TCA | CTC | TAT | GAT | CGT | CCA | GCC | 2426 |
| Val | Ser | Lys | Tyr | Ser 755 | Asp | Ile | Gln | Arg | Ser 760 | Leu | Tyr | Asp | Arg | Pro 765 | Ala | |
| TCA | TAT | AAG | AAG | AAA | TCT | ATG | TTA | GAC | TCA | GAA | GTC | AAA | AAC | CTC | CTT | 2474 |
| Ser | Tyr | Lys | Lys 770 | Lys | Ser | Met | Leu | Asp 775 | Ser | Glu | Val | Lys | Asn 780 | Leu | Leu | |
| TCA | GAT | GAT | AAC | TCA | GAA | GGC | CTT | ACT | TTA | TTG | GAT | TTG | TTG | AGC | TTC | 2522 |
| Ser | Asp | Asp 785 | Asn | Ser | Glu | Gly | Leu 790 | Thr | Leu | Leu | Asp | Leu 795 | Leu | Ser | Phe | |
| ACC | TAT | CAA | GTT | GCC | CGA | GGA | ATG | GAG | TTT | TTG | GCT | TCA | AAA | AAT | TGT | 2570 |
| Thr | Tyr 800 | Gln | Val | Ala | Arg | Gly 805 | Met | Glu | Phe | Leu | Ala 810 | Ser | Lys | Asn | Cys | |
| GTC | CAC | CGT | GAT | CTG | GCT | GCT | CGC | AAC | GTT | CTC | CTG | GCA | CAA | GGA | AAA | 2618 |
| Val | His 815 | Arg | Asp | Leu | Ala 820 | Ala | Arg | Asn | Val | Leu 825 | Leu | Ala | Gln | Gly | Lys 830 | |
| ATT | GTG | AAG | ATC | TGT | GAC | TTT | GGC | CTG | GCC | AGA | GAC | ATC | ATG | CAT | GAT | 2666 |
| Ile | Val | Lys | Ile | Cys 835 | Asp | Phe | Gly | Leu | Ala 840 | Arg | Asp | Ile | Met | His 845 | Asp | |
| TCG | AAC | TAT | GTG | TCG | AAA | GGC | AGT | ACC | TTT | CTG | CCC | GTG | AAG | TGG | ATG | 2714 |
| Ser | Asn | Tyr | Val 850 | Ser | Lys | Gly | Ser | Thr 855 | Phe | Leu | Pro | Val | Lys 860 | Trp | Met | |
| GCT | CCT | GAG | AGC | ATC | TTT | GAC | AAC | CTC | TAC | ACC | ACA | CTG | AGT | GAT | GTC | 2762 |
| Ala | Pro | Glu | Ser 865 | Ile | Phe | Asp | Asn | Leu 870 | Tyr | Thr | Thr | Leu | Ser 875 | Asp | Val | |

-continued

| | | | | | | | | | | | | | | | | |
|---|---|---|---|---|---|---|---|---|---|---|---|---|---|---|---|---|
| TGG | TCT | TAT | GGC | ATT | CTG | CTC | TGG | GAG | ATC | TTT | TCC | CTT | GGT | GGC | ACC | 2810 |
| Trp | Ser | Tyr | Gly | Ile | Leu | Leu | Trp | Glu | Ile | Phe | Ser | Leu | Gly | Gly | Thr | |
| | 880 | | | | 885 | | | | | 890 | | | | | | |
| CCT | TAC | CCC | GGC | ATG | ATG | GTG | GAT | TCT | ACT | TTC | TAC | AAT | AAG | ATC | AAG | 2858 |
| Pro | Tyr | Pro | Gly | Met | Met | Val | Asp | Ser | Thr | Phe | Tyr | Asn | Lys | Ile | Lys | |
| 895 | | | | 900 | | | | | 905 | | | | | 910 | | |
| AGT | GGG | TAC | CGG | ATG | GCC | AAG | CCT | GAC | CAC | GCT | ACC | AGT | GAA | GTC | TAC | 2906 |
| Ser | Gly | Tyr | Arg | Met | Ala | Lys | Pro | Asp | His | Ala | Thr | Ser | Glu | Val | Tyr | |
| | | | | 915 | | | | 920 | | | | | 925 | | | |
| GAG | ATC | ATG | GTG | AAA | TGC | TGG | AAC | AGT | GAG | CCG | GAG | AAG | AGA | CCC | TCC | 2954 |
| Glu | Ile | Met | Val | Lys | Cys | Trp | Asn | Ser | Glu | Pro | Glu | Lys | Arg | Pro | Ser | |
| | | | 930 | | | | 935 | | | | | 940 | | | | |
| TTT | TAC | CAC | CTG | AGT | GAG | ATT | GTG | GAG | AAT | CTG | CTG | CCT | GGA | CAA | TAT | 3002 |
| Phe | Tyr | His | Leu | Ser | Glu | Ile | Val | Glu | Asn | Leu | Leu | Pro | Gly | Gln | Tyr | |
| | | 945 | | | | 950 | | | | | 955 | | | | | |
| AAA | AAG | AGT | TAT | GAA | AAA | ATT | CAC | CTG | GAC | TTC | CTG | AAG | AGT | GAC | CAT | 3050 |
| Lys | Lys | Ser | Tyr | Glu | Lys | Ile | His | Leu | Asp | Phe | Leu | Lys | Ser | Asp | His | |
| 960 | | | | | 965 | | | | | 970 | | | | | | |
| CCT | GCT | GTG | GCA | CGC | ATG | CGT | GTG | GAC | TCA | GAC | AAT | GCA | TAC | ATT | GGT | 3098 |
| Pro | Ala | Val | Ala | Arg | Met | Arg | Val | Asp | Ser | Asp | Asn | Ala | Tyr | Ile | Gly | |
| 975 | | | | | 980 | | | | | 985 | | | | | 990 | |
| GTC | ACC | TAC | AAA | AAC | GAG | GAA | GAC | AAG | CTG | AAG | GAC | TGG | GAG | GGT | GGT | 3146 |
| Val | Thr | Tyr | Lys | Asn | Glu | Glu | Asp | Lys | Leu | Lys | Asp | Trp | Glu | Gly | Gly | |
| | | | | 995 | | | | | 1000 | | | | | 1005 | | |
| CTG | GAT | GAG | CAG | AGA | CTG | AGC | GCT | GAC | AGT | GGC | TAC | ATC | ATT | CCT | CTG | 3194 |
| Leu | Asp | Glu | Gln | Arg | Leu | Ser | Ala | Asp | Ser | Gly | Tyr | Ile | Ile | Pro | Leu | |
| | | | 1010 | | | | | 1015 | | | | | 1020 | | | |
| CCT | GAC | ATT | GAC | CCT | GTC | CCT | GAG | GAG | GAG | GAC | CTG | GGC | AAG | AGG | AAC | 3242 |
| Pro | Asp | Ile | Asp | Pro | Val | Pro | Glu | Glu | Glu | Asp | Leu | Gly | Lys | Arg | Asn | |
| | | 1025 | | | | | 1030 | | | | | 1035 | | | | |
| AGA | CAC | AGC | TCG | CAG | ACC | TCT | GAA | GAG | AGT | GCC | ATT | GAG | ACG | GGT | TCC | 3290 |
| Arg | His | Ser | Ser | Gln | Thr | Ser | Glu | Glu | Ser | Ala | Ile | Glu | Thr | Gly | Ser | |
| | 1040 | | | | 1045 | | | | | 1050 | | | | | | |
| AGC | AGT | TCC | ACC | TTC | ATC | AAG | AGA | GAG | GAC | GAG | ACC | ATT | GAA | GAC | ATC | 3338 |
| Ser | Ser | Ser | Thr | Phe | Ile | Lys | Arg | Glu | Asp | Glu | Thr | Ile | Glu | Asp | Ile | |
| 1055 | | | | | 1060 | | | | | 1065 | | | | | 1070 | |
| GAC | ATG | ATG | GAC | GAC | ATC | GGC | ATA | GAC | TCT | TCA | GAC | CTG | GTG | GAA | GAC | 3386 |
| Asp | Met | Met | Asp | Asp | Ile | Gly | Ile | Asp | Ser | Ser | Asp | Leu | Val | Glu | Asp | |
| | | | 1075 | | | | | 1080 | | | | | 1085 | | | |
| AGC | TTC | CTG | TAACTGGCGG | | ATTCGAGGGG | | TTCCTTCCAC | | TTCTGGGCC | | | | | | | 3435 |
| Ser | Phe | Leu | | | | | | | | | | | | | | |

| | |
|---|---|
| ACCTCTGGAT CCCGTTCAGA AAACCACTTT ATTGCAATGC GGAGGTTGAG AGGAGGACTT | 3495 |
| GGTTGATGTT TAAAGAGAAG TTCCCAGCCA AGGGCCTCGG GGAGCCTTTC TAAATATGAA | 3555 |
| TGAATGGGAT ATTTTGAAAT GAACTTTGTC AGTGTTGCCT CTTGCAATGC CTCAGTAGCA | 3615 |
| TCTCAGTGGT GTGTGAAGTT GGAGATAGA TGGATAAGGG AATAATAGGC CACAGAAGGT | 3675 |
| GAACTTTCTG CTTCAAGGAC ATTGGTGAGA GTCCAACAGA CACAATTTAT ACTGCGACAG | 3735 |
| AACTTCAGCA TTGTAATTAT GTAAATAACT CTAACCACGG CTGTGTTTAG ATTGTATTAA | 3795 |
| CTATCTTCTT TGGACTTCTG AAGAGACCAC TCAATCCATC CATGTACTTC CCTCTTGAAA | 3855 |
| CCTGATGTCA GCTGCTGTTG AACTTTTTAA AGAAGTGCAT GAAAAACCAT TTTTGACCTT | 3915 |
| AAAAGGTACT GGTACTATAG CATTTTGCTA TCTTTTTTAG TGTTAAAGAG ATAAAGAATA | 3975 |
| ATAATTAACC AACCTTGTTT AATAGATTTG GGTCATTTAG AAGCCTGACA ACTCATTTTC | 4035 |
| ATATTGTAAT CTATGTTTAT AATACTACTA CTGTTATCAG TAATGCTAAA TGTGTAATAA | 4095 |
| TGTAA | 4100 |

( 2 ) INFORMATION FOR SEQ ID NO:4:

(i) SEQUENCE CHARACTERISTICS:
  (A) LENGTH: 1089 amino acids
  (B) TYPE: amino acid
  (D) TOPOLOGY: linear (ii) MOLECULE TYPE: protein (xi) SEQUENCE DESCRIPTION: SEQ ID NO:4:

| Met | Gly | Thr | Ser | His | Pro | Ala | Phe | Leu | Val | Leu | Gly | Cys | Leu | Leu | Thr |
|---|---|---|---|---|---|---|---|---|---|---|---|---|---|---|---|
| 1 | | | | 5 | | | | | 10 | | | | | 15 | |
| Gly | Leu | Ser | Leu | Ile | Leu | Cys | Gln | Leu | Ser | Leu | Pro | Ser | Ile | Leu | Pro |
| | | | 20 | | | | 25 | | | | | 30 | | | |
| Asn | Glu | Asn | Glu | Lys | Val | Val | Gln | Leu | Asn | Ser | Ser | Phe | Ser | Leu | Arg |
| | | 35 | | | | | 40 | | | | | 45 | | | |
| Cys | Phe | Gly | Glu | Ser | Glu | Val | Ser | Trp | Gln | Tyr | Pro | Met | Ser | Glu | Glu |
| | 50 | | | | | 55 | | | | | 60 | | | | |
| Glu | Ser | Ser | Asp | Val | Glu | Ile | Arg | Asn | Glu | Glu | Asn | Asn | Ser | Gly | Leu |
| 65 | | | | | 70 | | | | | 75 | | | | | 80 |
| Phe | Val | Thr | Val | Leu | Glu | Val | Ser | Ser | Ala | Ser | Ala | Ala | His | Thr | Gly |
| | | | | 85 | | | | | 90 | | | | | 95 | |
| Leu | Tyr | Thr | Cys | Tyr | Tyr | Asn | His | Thr | Gln | Thr | Glu | Glu | Asn | Glu | Leu |
| | | | 100 | | | | | 105 | | | | | | 110 | |
| Glu | Gly | Arg | His | Ile | Tyr | Ile | Tyr | Val | Pro | Asp | Pro | Asp | Val | Ala | Phe |
| | | | 115 | | | | 120 | | | | | 125 | | | |
| Val | Pro | Leu | Gly | Met | Thr | Asp | Tyr | Leu | Val | Ile | Val | Glu | Asp | Asp | Asp |
| | 130 | | | | | 135 | | | | | 140 | | | | |
| Ser | Ala | Ile | Ile | Pro | Cys | Arg | Thr | Thr | Asp | Pro | Glu | Thr | Pro | Val | Thr |
| 145 | | | | | 150 | | | | | 155 | | | | | 160 |
| Leu | His | Asn | Ser | Glu | Gly | Val | Val | Pro | Ala | Ser | Tyr | Asp | Ser | Arg | Gln |
| | | | | 165 | | | | | 170 | | | | | 175 | |
| Gly | Phe | Asn | Gly | Thr | Phe | Thr | Val | Gly | Pro | Tyr | Ile | Cys | Glu | Ala | Thr |
| | | | 180 | | | | | 185 | | | | | 190 | | |
| Val | Lys | Gly | Lys | Lys | Phe | Gln | Thr | Ile | Pro | Phe | Asn | Val | Tyr | Ala | Leu |
| | | 195 | | | | | 200 | | | | | 205 | | | |
| Lys | Ala | Thr | Ser | Glu | Leu | Asp | Leu | Glu | Met | Glu | Ala | Leu | Lys | Thr | Val |
| | 210 | | | | | 215 | | | | | 220 | | | | |
| Tyr | Lys | Ser | Gly | Glu | Thr | Ile | Val | Val | Thr | Cys | Ala | Val | Phe | Asn | Asn |
| 225 | | | | | 230 | | | | | 235 | | | | | 240 |
| Glu | Val | Val | Asp | Leu | Gln | Trp | Thr | Tyr | Pro | Gly | Glu | Val | Lys | Gly | Lys |
| | | | | 245 | | | | | 250 | | | | | 255 | |
| Gly | Ile | Thr | Met | Leu | Glu | Glu | Ile | Lys | Val | Pro | Ser | Ile | Lys | Leu | Val |
| | | | 260 | | | | | 265 | | | | | 270 | | |
| Tyr | Thr | Leu | Thr | Val | Pro | Glu | Ala | Thr | Val | Lys | Asp | Ser | Gly | Asp | Tyr |
| | | 275 | | | | | 280 | | | | | 285 | | | |
| Glu | Cys | Ala | Ala | Arg | Gln | Ala | Thr | Arg | Glu | Val | Lys | Glu | Met | Lys | Lys |
| | 290 | | | | | 295 | | | | | 300 | | | | |
| Val | Thr | Ile | Ser | Val | His | Glu | Lys | Gly | Phe | Ile | Glu | Ile | Lys | Pro | Thr |
| 305 | | | | | 310 | | | | | 315 | | | | | 320 |
| Phe | Ser | Gln | Leu | Glu | Ala | Val | Asn | Leu | His | Glu | Val | Lys | His | Phe | Val |
| | | | | 325 | | | | | 330 | | | | | 335 | |
| Val | Glu | Val | Arg | Ala | Tyr | Pro | Pro | Pro | Arg | Ile | Ser | Trp | Leu | Lys | Asn |
| | | | 340 | | | | | 345 | | | | | 350 | | |
| Asn | Leu | Thr | Leu | Ile | Glu | Asn | Leu | Thr | Glu | Ile | Thr | Thr | Asp | Val | Glu |
| | | 355 | | | | | 360 | | | | | 365 | | | |
| Lys | Ile | Gln | Glu | Ile | Arg | Tyr | Arg | Ser | Lys | Leu | Lys | Leu | Ile | Arg | Ala |

|     |     |     |     |     | 370 |     |     |     | 375 |     |     |     |     | 380 |     |     |     |     |     |
| --- | --- | --- | --- | --- | --- | --- | --- | --- | --- | --- | --- | --- | --- | --- | --- | --- | --- | --- | --- |
| Lys 385 | Glu | Glu | Asp | Ser | Gly 390 | His | Tyr | Thr | Ile | Val 395 | Ala | Gln | Asn | Glu | Asp 400 |
| Ala | Val | Lys | Ser | Tyr 405 | Thr | Phe | Glu | Leu | Leu 410 | Thr | Gln | Val | Pro | Ser 415 | Ser |
| Ile | Leu | Asp | Leu 420 | Val | Asp | Asp | His | His 425 | Gly | Ser | Thr | Gly 430 | Gln | Thr |
| Val | Arg | Cys 435 | Thr | Ala | Glu | Gly | Thr 440 | Pro | Leu | Pro | Asp | Ile 445 | Glu | Trp | Met |
| Ile | Cys 450 | Lys | Asp | Ile | Lys | Lys 455 | Cys | Asn | Asn | Glu | Thr 460 | Ser | Trp | Thr | Ile |
| Leu 465 | Ala | Asn | Asn | Val | Ser 470 | Asn | Ile | Ile | Thr | Glu 475 | Ile | His | Ser | Arg | Asp 480 |
| Arg | Ser | Thr | Val | Glu 485 | Gly | Arg | Val | Thr | Phe 490 | Ala | Lys | Val | Glu | Glu 495 | Thr |
| Ile | Ala | Val | Arg 500 | Cys | Leu | Ala | Lys | Asn 505 | Leu | Leu | Gly | Ala | Glu 510 | Asn | Arg |
| Glu | Leu | Lys 515 | Leu | Val | Ala | Pro | Thr 520 | Leu | Arg | Ser | Glu | Leu 525 | Thr | Val | Ala |
| Ala | Ala 530 | Val | Leu | Val | Leu | Leu 535 | Val | Ile | Val | Ile | Ile 540 | Ser | Leu | Ile | Val |
| Leu 545 | Val | Val | Ile | Trp | Lys 550 | Gln | Lys | Pro | Arg | Tyr 555 | Glu | Ile | Arg | Trp | Arg 560 |
| Val | Ile | Glu | Ser | Ile 565 | Ser | Pro | Asp | Gly | His 570 | Glu | Tyr | Ile | Tyr | Val 575 | Asp |
| Pro | Met | Gln | Leu 580 | Pro | Tyr | Asp | Ser | Arg 585 | Trp | Glu | Phe | Pro | Arg 590 | Asp | Gly |
| Leu | Val | Leu 595 | Gly | Arg | Val | Leu | Gly 600 | Ser | Gly | Ala | Phe | Gly 605 | Lys | Val | Val |
| Glu | Gly 610 | Thr | Ala | Tyr | Gly | Leu 615 | Ser | Arg | Ser | Gln | Pro 620 | Val | Met | Lys | Val |
| Ala 625 | Val | Lys | Met | Leu | Lys 630 | Pro | Thr | Ala | Arg | Ser 635 | Ser | Glu | Lys | Gln | Ala 640 |
| Leu | Met | Ser | Glu | Leu 645 | Lys | Ile | Met | Thr | His 650 | Leu | Gly | Pro | His | Leu 655 | Asn |
| Ile | Val | Asn | Leu 660 | Leu | Gly | Ala | Cys | Thr 665 | Lys | Ser | Gly | Pro | Ile 670 | Tyr | Ile |
| Ile | Thr | Glu 675 | Tyr | Cys | Phe | Tyr | Gly 680 | Asp | Leu | Val | Asn | Tyr 685 | Leu | His | Lys |
| Asn | Arg 690 | Asp | Ser | Phe | Leu | Ser 695 | His | His | Pro | Glu | Lys 700 | Pro | Lys | Lys | Glu |
| Leu | Asp 705 | Ile | Phe | Gly | Leu 710 | Asn | Pro | Ala | Asp | Glu 715 | Ser | Thr | Arg | Ser | Tyr 720 |
| Val | Ile | Leu | Ser | Phe 725 | Glu | Asn | Asn | Gly | Asp 730 | Tyr | Met | Asp | Met | Lys 735 | Gln |
| Ala | Asp | Thr | Thr 740 | Gln | Tyr | Val | Pro | Met 745 | Leu | Glu | Arg | Lys | Glu 750 | Val | Ser |
| Lys | Tyr | Ser 755 | Asp | Ile | Gln | Arg | Ser 760 | Leu | Tyr | Asp | Arg | Pro 765 | Ala | Ser | Tyr |
| Lys | Lys | Lys 770 | Ser | Met | Leu | Asp | Ser 775 | Glu | Val | Lys | Asn 780 | Leu | Leu | Ser | Asp |
| Asp 785 | Asn | Ser | Glu | Gly | Leu 790 | Thr | Leu | Leu | Asp | Leu 795 | Leu | Ser | Phe | Thr | Tyr 800 |

| | | | | | | | | | | | | | | |
|---|---|---|---|---|---|---|---|---|---|---|---|---|---|---|
| Gln | Val | Ala | Arg | Gly<br>805 | Met | Glu | Phe | Leu | Ala<br>810 | Ser | Lys | Asn | Cys | Val His<br>815 |
| Arg | Asp | Leu | Ala<br>820 | Ala | Arg | Asn | Val | Leu<br>825 | Leu | Ala | Gln | Gly | Lys<br>830 | Ile Val |
| Lys | Ile | Cys<br>835 | Asp | Phe | Gly | Leu | Ala<br>840 | Arg | Asp | Ile | Met | His<br>845 | Asp | Ser Asn |
| Tyr | Val<br>850 | Ser | Lys | Gly | Ser<br>855 | Thr | Phe | Leu | Pro | Val<br>860 | Lys | Trp | Met | Ala Pro |
| Glu<br>865 | Ser | Ile | Phe | Asp | Asn<br>870 | Leu | Tyr | Thr | Thr<br>875 | Leu | Ser | Asp | Val | Trp Ser<br>880 |
| Tyr | Gly | Ile | Leu | Leu<br>885 | Trp | Glu | Ile | Phe | Ser<br>890 | Leu | Gly | Gly | Thr | Pro Tyr<br>895 |
| Pro | Gly | Met | Met<br>900 | Val | Asp | Ser | Thr | Phe<br>905 | Tyr | Asn | Lys | Ile | Lys<br>910 | Ser Gly |
| Tyr | Arg | Met<br>915 | Ala | Lys | Pro | Asp | His<br>920 | Ala | Thr | Ser | Glu | Val<br>925 | Tyr | Glu Ile |
| Met | Val<br>930 | Lys | Cys | Trp | Asn<br>935 | Ser | Glu | Pro | Glu | Lys<br>940 | Arg | Pro | Ser | Phe Tyr |
| His<br>945 | Leu | Ser | Glu | Ile | Val<br>950 | Glu | Asn | Leu | Leu | Pro<br>955 | Gly | Gln | Tyr | Lys Lys<br>960 |
| Ser | Tyr | Glu | Lys | Ile<br>965 | His | Leu | Asp | Phe | Leu<br>970 | Lys | Ser | Asp | His | Pro Ala<br>975 |
| Val | Ala | Arg | Met<br>980 | Arg | Val | Asp | Ser | Asp<br>985 | Asn | Ala | Tyr | Ile | Gly<br>990 | Val Thr |
| Tyr | Lys | Asn<br>995 | Glu | Glu | Asp | Lys | Leu<br>1000 | Lys | Asp | Trp | Glu | Gly<br>1005 | Gly | Leu Asp |
| Glu | Gln<br>1010 | Arg | Leu | Ser | Ala | Asp<br>1015 | Ser | Gly | Tyr | Ile | Ile<br>1020 | Pro | Leu | Pro Asp |
| Ile | Asp<br>1025 | Pro | Val | Pro | Glu<br>1030 | Glu | Glu | Asp | Leu | Gly<br>1035 | Lys | Arg | Asn | Arg His<br>1040 |
| Ser | Ser | Gln | Thr | Ser<br>1045 | Glu | Glu | Ser | Ala | Ile<br>1050 | Glu | Thr | Gly | Ser | Ser Ser<br>1055 |
| Ser | Thr | Phe | Ile<br>1060 | Lys | Arg | Glu | Asp | Glu<br>1065 | Thr | Ile | Glu | Asp | Ile<br>1070 | Asp Met |
| Met | Asp | Asp<br>1075 | Ile | Gly | Ile | Asp | Ser<br>1080 | Ser | Asp | Leu | Val | Glu<br>1085 | Asp | Ser Phe |
| Leu | | | | | | | | | | | | | | |

( 2 ) INFORMATION FOR SEQ ID NO:5:

( i ) SEQUENCE CHARACTERISTICS:
    ( A ) LENGTH: 6375 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: Homo Sapiens
    ( B ) STRAIN: lambda gt10

( i x ) FEATURE:
    ( A ) NAME/KEY: CDS
    ( B ) LOCATION: 129..3395
    ( D ) OTHER INFORMATION: /note="nucleotide number 1 of this
    sequence is identical to the nucleotide number 1

-continued of the previous 4100 long sequence"

( x i ) SEQUENCE DESCRIPTION: SEQ ID NO:5:

| | | | | | | |
|---|---|---|---|---|---|---|
| TTGGAGCTAC | AGGGAGAGAA | ACAGAGGAGG | AGACTGCAAG | AGATCATTGG | AGGCCGTGGG | 60 |
| CACGCTCTTT | ACTCCATGTG | TGGGACATTC | ATTGCGGAAT | AACATCGGAG | GAGAAGTTTC | 120 |
| CCAGAGCTAT | GGGGACTTCC | CATCCGGCGT | TCCTGGTCTT | AGGCTGTCTT | CTCACAGGGC | 180 |
| TGAGCCTAAT | CCTCTGCCAG | CTTTCATTAC | CCTCTATCCT | TCCAAATGAA | AATGAAAAGG | 240 |
| TTGTGCAGCT | GAATTCATCC | TTTTCTCTGA | GATGCTTTGG | GGAGAGTGAA | GTGAGCTGGC | 300 |
| AGTACCCCAT | GTCTGAAGAA | GAGAGCTCCG | ATGTGGAAAT | CAGAAATGAA | GAAAACAACA | 360 |
| GCGGCCTTTT | TGTGACGGTC | TTGGAAGTGA | GCAGTGCCTC | GGCGGCCCAC | ACAGGGTTGT | 420 |
| ACACTTGCTA | TTACAACCAC | ACTCAGACAG | AAGAGAATGA | GCTTGAAGGC | AGGCACATTT | 480 |
| ACATCTATGT | GCCAGACCCA | GATGTAGCCT | TTGTACCTCT | AGGAATGACG | GATTATTTAG | 540 |
| TCATCGTGGA | GGATGATGAT | TCTGCCATTA | TACCTTGTCG | CACAACTGAT | CCCGAGACTC | 600 |
| CTGTAACCTT | ACACAACAGT | GAGGGGGTGG | TACCTGCCTC | CTACGACAGC | AGACAGGGCT | 660 |
| TTAATGGGAC | CTTCACTGTA | GGGCCCTATA | TCTGTGAGGC | CACCGTCAAA | GGAAAGAAGT | 720 |
| TCCAGACCAT | CCCATTTAAT | GTTTATGCTT | TAAAAGCAAC | ATCAGAGCTG | GATCTAGAAA | 780 |
| TGGAAGCTCT | TAAAACCGTG | TATAAGTCAG | GGGAAACGAT | TGTGGTCACC | TGTGCTGTTT | 840 |
| TTAACAATGA | GGTGGTTGAC | CTTCAATGGA | CTTACCCTGG | AGAAGTGAAA | GGCAAAGGCA | 900 |
| TCACAATGCT | GGAAGAAATC | AAAGTCCCAT | CCATCAAATT | GGTGTACACT | TTGACGGTCC | 960 |
| CCGAGGCCAC | GGTGAAAGAC | AGTGGAGATT | ACGAATGTGC | TGCCCGCCAG | GCTACCAGGG | 1020 |
| AGGTCAAAGA | AATGAAGAAA | GTCACTATTT | CTGTCCATGA | GAAAGGTTTC | ATTGAAATCA | 1080 |
| AACCCACCTT | CAGCCAGTTG | GAAGCTGTCA | ACCTGCATGA | AGTCAAACAT | TTTGTTGTAG | 1140 |
| AGGTGCGGGC | CTACCCACCT | CCCAGGATAT | CCTGGCTGAA | AAACAATCTG | ACTCTGATTG | 1200 |
| AAAATCTCAC | TGAGATCACC | ACTGATGTGG | AAAAGATTCA | GGAAATAAGG | TATCGAAGCA | 1260 |
| AATTAAAGCT | GATCCGTGCT | AAGGAAGAAG | ACAGTGGCCA | TTATACTATT | GTAGCTCAAA | 1320 |
| ATGAAGATGC | TGTGAAGAGC | TATACTTTTG | AACTGTTAAC | TCAAGTTCCT | TCATCCATTC | 1380 |
| TGGACTTGGT | CGATGATCAC | CATGGCTCAA | CTGGGGGACA | GACGGTGAGG | TGCACAGCTG | 1440 |
| AAGGCACGCC | GCTTCCTGAT | ATTGAGTGGA | TGATATGCAA | AGATATTAAG | AAATGTAATA | 1500 |
| ATGAAACTTC | CTGGACTATT | TTGGCCAACA | ATGTCTCAAA | CATCATCACG | GAGATCCACT | 1560 |
| CCCGAGACAG | GAGTACCGTG | GAGGGCCGTG | TGACTTTCGC | CAAAGTGGAG | GAGACCATCG | 1620 |
| CCGTGCGATG | CCTGGCTAAG | AATCTCCTTG | GAGCTGAGAA | CCGAGAGCTG | AAGCTGGTGG | 1680 |
| CTCCCACCCT | GCGTTCTGAA | CTCACGGTGG | CTGCTGCAGT | CCTGGTGCTG | TTGGTGATTG | 1740 |
| TGATCATCTC | ACTTATTGTC | CTGGTTGTCA | TTTGGAAACA | GAAACCGAGG | TATGAAATTC | 1800 |
| GCTGGAGGGT | CATTGAATCA | ATCAGCCCAG | ATGGACATGA | ATATATTTAT | GTGGACCCGA | 1860 |
| TGCAGCTGCC | TTATGACTCA | AGATGGGAGT | TTCCAAGAGA | TGGACTAGTG | CTTGGTCGGG | 1920 |
| TCTTGGGGTC | TGGAGCGTTT | GGGAAGGTGG | TTGAAGGAAC | AGCCTATGGA | TTAAGCCGGT | 1980 |
| CCCAACCTGT | CATGAAAGTT | GCAGTGAAGA | TGCTAAAACC | CACGGCCAGA | TCCAGTGAAA | 2040 |
| AACAAGCTCT | CATGTCTGAA | CTGAAGATAA | TGACTCACCT | GGGGCCACAT | TTGAACATTG | 2100 |
| TAAACTTGCT | GGGAGCCTGC | ACCAAGTCAG | GCCCCATTTA | CATCATCACA | GAGTATTGCT | 2160 |
| TCTATGGAGA | TTTGGTCAAC | TATTTGCATA | AGAATAGGGA | TAGCTTCCTG | AGCCACCACC | 2220 |
| CAGAGAAGCC | AAAGAAAGAG | CTGGATATCT | TTGGATTGAA | CCCTGCTGAT | GAAAGCACAC | 2280 |

```
GGAGCTATGT TATTTTATCT TTTGAAAACA ATGGTGACTA CATGGACATG AAGCAGGCTG      2340
ATACTACACA GTATGTCCCC ATGCTAGAAA GGAAGAGGT  TTCTAAATAT TCCGACATCC      2400
AGAGATCACT CTATGATCGT CCAGCCTCAT ATAAGAAGAA ATCTATGTTA GACTCAGAAG      2460
TCAAAAACCT CCTTTCAGAT GATAACTCAG AAGGCCTTAC TTTATTGGAT TTGTTGAGCT      2520
TCACCTATCA AGTTGCCCGA GGAATGGAGT TTTTGGCTTC AAAAAATTGT GTCCACCGTG      2580
ATCTGGCTGC TCGCAACGTT CTCCTGGCAC AAGGAAAAAT TGTGAAGATC TGTGACTTTG      2640
GCCTGGCCAG AGACATCATG CATGATTCGA ACTATGTGTC GAAAGGCAGT ACCTTTCTGC      2700
CCGTGAAGTG GATGGCTCCT GAGAGCATCT TTGACAACCT CTACACCACA CTGAGTGATG      2760
TCTGGTCTTA TGGCATTCTG CTCTGGGAGA TCTTTTCCCT TGGTGGCACC CCTTACCCCG      2820
GCATGATGGT GGATTCTACT TTCTACAATA AGATCAAGAG TGGGTACCGG ATGGCCAAGC      2880
CTGACCACGC TACCAGTGAA GTCTACGAGA TCATGGTGAA ATGCTGGAAC AGTGAGCCGG      2940
AGAAGAGACC CTCCTTTTAC CACCTGAGTG AGATTGTGGA GAATCTGCTG CCTGGACAAT      3000
ATAAAAAGAG TTATGAAAAA ATTCACCTGG ACTTCCTGAA GAGTGACCAT CCTGCTGTGG      3060
CACGCATGCG TGTGGACTCA GACAATGCAT ACATTGGTGT CACCTACAAA AACGAGGAAG      3120
ACAAGCTGAA GGACTGGGAG GGTGGTCTGG ATGAGCAGAG ACTGAGCGCT GACAGTGGCT      3180
ACATCATTCC TCTGCCTGAC ATTGACCCTG TCCCTGAGGA GGAGGACCTG GGCAAGAGGA      3240
ACAGACACAG CTCGCAGACC TCTGAAGAGA GTGCCATTGA GACGGGTTCC AGCAGTTCCA      3300
CCTTCATCAA GAGAGAGGAC GAGACCATTG AAGACATCGA CATGATGGAC GACATCGGCA      3360
TAGACTCTTC AGACCTGGTG GAAGACAGCT TCCTGTAACT GGCGGATTCG AGGGGTTCCT      3420
TCCACTTCTG GGGCCACCTC TGGATCCCGT TCAGAAAACC ACTTTATTGC AATGCGGAGG      3480
TTGAGAGGAG GACTTGGTTG ATGTTTAAAG AGAAGTTCCC AGCCAAGGGC CTCGGGGAGC      3540
CTTTCTAAAT ATGAATGAAT GGGATATTTT GAAATGAACT TTGTCAGTGT TGCCTCTTGC      3600
AATGCCTCAG TAGCATCTCA GTGGTGTGTG AAGTTTGGAG ATAGATGGAT AAGGGAATAA      3660
TAGGCCACAG AAGGTGAACT TTCTGCTTCA AGGACATTGG TGAGAGTCCA ACAGACACAA      3720
TTTATACTGC GACAGAACTT CAGCATTGTA ATTATGTAAA TAACTCTAAC CACGGCTGTG      3780
TTAGATTGT  ATTAACTATC TTCTTTGGAC TTCTGAAGAG ACCACTCAAT CCATCCATGT      3840
ACTTCCCTCT TGAAACCTGA TGTCAGCTGC TGTTGAACTT TTTAAAGAAG TGCATGAAAA      3900
ACCATTTTTG ACCTTAAAAG GTACTGGTAC TATAGCATTT TGCTATCTTT TTAGTGTTA      3960
AAGAGATAAA GAATAATAAT TAACCAACCT TGTTTAATAG ATTTGGGTCA TTTAGAAGCC      4020
TGACAACTCA TTTTCATATT GTAATCTATG TTTATAATAC TACTACTGTT ATCAGTAATG      4080
CTAAATGTGT AATAATGTAA CATGATTTCC CTCCACACAA AGCACAATTT AAAAACAATC      4140
CTTACTAAGT AGGTGATGAG TTTGACAGTT TTTGACATTT ATATTAAATA ACATGTTTCT      4200
CTATAAAGTA TGGTAATAGC TTTAGTGAAT TAAATTTAGT TGAGCATAGA GAACAAAGTA      4260
AAAGTAGTGT TGTCCAGGAA GTCAGAATTT TTAACTGTAC TGAATAGGTT CCCCAATCCA      4320
TCGTATTAAA AAACAATTAA CTGCCCTCTG AAATAATGGG ATTAGAAACA AACAAAACTC      4380
TTAAGTCCTA AAAGTTCTCA ATGTAGAGGC ATAAACCTGT GCTGAACATA ACTTCTCATG      4440
TATATTACCC AATGGAAAAT ATAATGATCA GCGCANAAAG ACTGGATTTG CAGAAGTTNT      4500
TTTTTTTTT  TCTTCTTGCC TGATGAAAGC TTTGGCGACC CCAATATATG TATTTTTTGA      4560
ATCTATGAAC CTGAAAAGGG TCACAAAGGA TGCCCAGACA TCAGCCTCCT TCTTTCACCC      4620
CTTACCCCAA AGAGAAAGAG TTTGAAACTC GAGACCATAA AGATATTCTT TAGTGGAGGC      4680
```

```
TGGAAGTGCA  TTAGCCTGAT  CCTCAGTTCT  CAAATGTGTG  TGGCAGCCAG  GTAGACTAGT    4740

ACCTGGGTTT  CCATCCTTGA  GATTCTGAAG  TATGAAGTCT  GAGGGAAACC  AGAGTCTGTA    4800

TTTTTCTAAA  CTCCCTGGCT  GTTCTGATCG  GCCAGGTTTC  GGAAACACTG  ACTTAGGTTT    4860

CAGGAAGTTG  CCATGGGAAA  CAAATAATTT  GAACTTTGGA  ACAGGGTTCT  TAAGTTGGTG    4920

CGTCCTTCGG  ATGATAAATT  TAGGAACCGA  AGTCCAATCA  CTGTAAATTA  CGGTAGATCG    4980

ATCGTTAACG  CTGGAATTAA  ATTGAAAGGT  CAGAATCGAC  TCCGACTCTT  TCGATTTCAA    5040

ACCAAAACTG  TCCAAAAGGT  TTTCATTTCT  ACGATGAAGG  GTGACATACC  CCCTCTAACT    5100

TGAAAGGGGC  AGAGGGCAGA  AGAGCGGAGG  GTGAGGTATG  GGCGGTTCC   TTTCCGTACA    5160

TGTTTTAAT   ACGTAAGTC   ACAAGGTTCA  GAGACACATT  GGTCGAGTCA  CAAAACCACC    5220

TTTTTGTAA   AATTCAAAAT  GACTATTAAA  CTCCAATCTA  CCCTCCTACT  TAACAGTGTA    5280

GATAGGTGTG  ACAGTTTGTC  CAACCACACC  CAAGTAACCG  TAAGAAACGT  TATGACGAAT    5340

TAACGACTAT  GGTATACTTA  CTTTGTACCC  GACACTAATG  ACGTTAGTGA  CACGATAGCC    5400

GTCTACTACG  AAACCTTCTA  CGTCTTCGTT  ATTATTTCAT  GAACTGATGG  ATGACCACAT    5460

TAGAGTTACG  TTCGGGGTTG  AAAGAATAGG  TTGAAAAAGT  ATCATTCACG  CTTCTGACTC    5520

GGTCTAACCG  GTTAATTTTT  CTTTTGGACT  GATCCAAGAC  ATCTCGGTTA  ATCTGAACTT    5580

TATGCAAACA  CAAAGATCTT  AGTGTCGAGT  TCGTAAGACA  AATAGCGAGT  GAGAGGGAAC    5640

ATGTCGGAAT  AAAACAACCA  CGAAACGTAA  AACTATAACG  ACACTCGGAA  CGTACTGTAG    5700

TACTCCGGCC  TACTTTGAAG  AGTCAGGTCG  TCAAAGGTCA  GGATTGTTTA  CGAGGGTGGA    5760

CTTAAACATA  TACTGACGTA  AACACCCACA  CACACACAAA  AGTCGTTTAA  GGTCTAAACA    5820

AAGGAAAACC  GGAGGACGTT  TCAGAGGTCT  TCTTTTAAAC  GGTTAGAAAG  GATGAAAGAT    5880

AAAAATACTA  CTGTTAGTTT  CGGCCGGACT  CTTTGTGATA  AACACTGAAA  AATTTGCTAA    5940

TCACTACAGG  AATTTTACAC  CAGACGGTTA  GACATGTTTT  ACCAGGATAA  AAACACTTCT    6000

CCCTGTATTC  TATTTTACTA  CAATATGTAG  TTATACATAT  ATACATAAAG  ATATATCTGA    6060

ACCTCTTATG  ACGGTTTTGT  AAATACTGTT  CGACATAGTG  ACGGAAGCAA  ATATAAAAAA    6120

ATTGACACTA  TTAGGGGTGT  CCGTGTAATT  GACAACGTGA  AAACTTACAG  GTTTTAAATA    6180

TAAAATCTTT  ATTATTTTTC  TTTCTATGAA  TGTACAAGGG  TTTTGTTACC  ACACCACTTA    6240

CACACTCTTT  TTGATTGAAC  TATCCCAGAT  GGTTATGTTT  TACATAATGC  TTACGGGGAC    6300

AAGTACAAAA  ACAAAATTTT  GCACATTTAC  TTCTAGAAAT  ATAAAGTTAT  TTACTATATA    6360

TTAAATTTCC  TTAAG                                                         6375
```

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

```
CCACACTCCT  TGCCCTTTAA  GTAGCTTCCT  GTAGGGGGCT  G                          41
```

( 2 ) INFORMATION FOR SEQ ID NO:7:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo Sapiens ( x i ) SEQUENCE DESCRIPTION: SEQ ID NO:7:

TCCTTCGACC TACAGATCAA TTAGCTTCCT GTAGGGGCT G        41

( 2 ) INFORMATION FOR SEQ ID NO:8:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo Sapiens ( x i ) SEQUENCE DESCRIPTION: SEQ ID NO:8:

ATCACCGTGG TTGAGAGCGG CTAGCTTCCT GTAGGGGCT G        41

( 2 ) INFORMATION FOR SEQ ID NO:9:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo Sapiens ( x i ) SEQUENCE DESCRIPTION: SEQ ID NO:9:

TACAGACTCC AGGTGTCATC CTAGCTTCCT GTAGGGGCT G        41

( 2 ) INFORMATION FOR SEQ ID NO:10:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo Sapiens ( x i ) SEQUENCE DESCRIPTION: SEQ ID NO:10:

CTCTACATCT TTGTGCCAGA TCCCTAGCTT CCTGTAGGGG GCTG    44

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo Sapiens ( x i ) SEQUENCE DESCRIPTION: SEQ ID NO:11:

CAGATCTCTC AGGGCCTGGT CACCGTGGGC TTCCTCCCTA ATCAT    45

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo Sapiens ( x i ) SEQUENCE DESCRIPTION: SEQ ID NO:12:

CAGATCTCTC AGGGCCTGGT CATCAACGTC TCTGTGAACG CAGTGCAG    48

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo Sapiens ( x i ) SEQUENCE DESCRIPTION: SEQ ID NO:13:

CAGATCTCTC AGGGCCTGGT CTACGTGCGG CTCCTGGGAG AGCTG    45

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo Sapiens ( x i ) SEQUENCE DESCRIPTION: SEQ ID NO:14:

CAGATCTCTC AGGGCCTGGT CGTCCGAGTG CTGGAGCTAA GT     42

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:15:

GCTCCCACCC TGCGTTCTGA ATAACTGGCG GATTCGAGGG G     41

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:16:

GAACTGTTAA CTCAAGTTCC TTAACTGGCG GATTCGAGGG G     41

( 2 ) INFORMATION FOR SEQ ID NO:17:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:17:

ATTTCTGTCC ATGAGAAAGG TTAACTGGCG GATTCGAGGG G    41

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:18:

TATGCTTTAA AAGCAACATC ATAACTGGCG GATTCGAGGG G    41

( 2 ) INFORMATION FOR SEQ ID NO:19:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:19:

ATTTACATCT ATGTGCCAGA CCCATAACTG GCGGATTCGA GGGG    44

( 2 ) INFORMATION FOR SEQ ID NO:20:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Homo Sapiens
        ( B ) STRAIN: lambda gt10

( x i ) SEQUENCE DESCRIPTION: SEQ ID NO:20:

AGCCTAATCC TCTGCCAGCT TGATGTAGCC TTTGTACCTC TAGGA    45

( 2 ) INFORMATION FOR SEQ ID NO:21:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
                ( A ) ORGANISM: Homo Sapiens
                ( B ) STRAIN: lambda gt10

( x i ) SEQUENCE DESCRIPTION: SEQ ID NO:21:

AGCCTAATCC TCTGCCAGCT TGAGCTGGAT CTAGAAATGG AAGCTCTT 48

( 2 ) INFORMATION FOR SEQ ID NO:22:

( i ) SEQUENCE CHARACTERISTICS:
                ( A ) LENGTH: 45 base pairs
                ( B ) TYPE: nucleic acid
                ( C ) STRANDEDNESS: single
                ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
                ( A ) ORGANISM: Homo Sapiens
                ( B ) STRAIN: lambda gt10

( x i ) SEQUENCE DESCRIPTION: SEQ ID NO:22:

AGCCTAATCC TCTGCCAGCT TTTCATTGAA ATCAAACCCA CCTTC 45

( 2 ) INFORMATION FOR SEQ ID NO:23:

( i ) SEQUENCE CHARACTERISTICS:
                ( A ) LENGTH: 42 base pairs
                ( B ) TYPE: nucleic acid
                ( C ) STRANDEDNESS: single
                ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
                ( A ) ORGANISM: Homo Sapiens
                ( B ) STRAIN: lambda gt10

( x i ) SEQUENCE DESCRIPTION: SEQ ID NO:23:

AGCCTAATCC TCTGCCAGCT TTCATCCATT CTGGACTTGG TC 42